(12) United States Patent
Madathil et al.

(10) Patent No.: US 9,957,214 B2
(45) Date of Patent: May 1, 2018

(54) MULTIFUNCTIONAL RADICAL QUENCHERS

(71) Applicant: ARIZONA BOARD OF REGENTS ON BEHALF OF ARIZONA STATE UNIVERSITY, Scottsdale, AZ (US)

(72) Inventors: Manikandadas Mathilakathu Madathil, Tempe, AZ (US); Omar Khdour, Phoenix, AZ (US); Sidney Hecht, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days. days.

(21) Appl. No.: 14/434,725

(22) PCT Filed: Oct. 10, 2013

(86) PCT No.: PCT/US2013/064359
§ 371 (c)(1),
(2) Date: Apr. 9, 2015

(87) PCT Pub. No.: WO2014/059158
PCT Pub. Date: Apr. 17, 2014

(65) Prior Publication Data
US 2015/0274628 A1    Oct. 1, 2015

Related U.S. Application Data

(60) Provisional application No. 61/712,170, filed on Oct. 10, 2012.

(51) Int. Cl.
| | |
|---|---|
| *C07C 46/02* | (2006.01) |
| *C07C 49/753* | (2006.01) |
| *C07C 225/06* | (2006.01) |
| *C07C 225/20* | (2006.01) |
| *C07D 225/06* | (2006.01) |
| *A61K 9/00* | (2006.01) |
| *A61K 9/08* | (2006.01) |
| *A61K 9/20* | (2006.01) |
| *A61K 9/48* | (2006.01) |
| *C07C 229/10* | (2006.01) |

(52) U.S. Cl.
CPC ............ *C07C 49/753* (2013.01); *C07C 46/02* (2013.01); *C07C 225/20* (2013.01); *C07C 229/10* (2013.01); *C07D 225/06* (2013.01); *A61K 9/008* (2013.01); *A61K 9/0019* (2013.01); *A61K 9/08* (2013.01); *A61K 9/2018* (2013.01); *A61K 9/2054* (2013.01); *A61K 9/4858* (2013.01)

(58) Field of Classification Search
CPC ....... C07C 46/02; C07C 50/28; C07C 225/20; C07C 229/10; C07C 49/753; C07C 225/06; C07C 225/10; C07D 225/06; A61K 31/0019; A61K 31/08; A61K 31/008; A61K 31/2018; A61K 31/2054; A61K 31/4858
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,104,874 A | 4/1992 | Ikeda et al. |
| 5,220,042 A * | 6/1993 | Iwaki .................... C07C 43/315 549/551 |
| 2015/0274628 A1 | 10/2015 | Madathil et al. |

FOREIGN PATENT DOCUMENTS

| | | |
|---|---|---|
| JP | 61197515 A | 9/1986 |
| WO | 2001005384 A2 | 1/2001 |
| WO | 2002000683 A2 | 1/2002 |
| WO | 2007134328 A2 | 11/2007 |
| WO | 2010138820 A2 | 12/2010 |
| WO | 2011019419 A1 | 2/2011 |

(Continued)

OTHER PUBLICATIONS

Mossa et. al., Phytochemistry, 1999, Pergamon, vol. 50, pp. 1063-1068.*
Luly et. al., Journal of the American Chemical Society, 1983, American Chemical Society, vol. 195, pp. 2859-2866.*
Joshi et. al., Journal of the Chemical Society, Perkin Transactions 1: Organic and Bio-Organic Chemistry, 1975, Royal Society of Chemistry, vol. 4, pp. 327-332.*
Ramasarma et. al., "Studies on the Electron Transport System", The Journal of Biological Chemistry, 1960, American Chemical Society, vol. 235(11), pp. 3309-3314.*

(Continued)

*Primary Examiner* — Sarah Pihonak
(74) *Attorney, Agent, or Firm* — Viksnins Harris Padys Malen LLP

(57) ABSTRACT

The invention provides a compound of formula (I): [insert formula (I)] wherein X, Y, and $R^1$-$R^4$ have any of the values defined in the specification, and salts thereof, as well as compositions comprising the compounds or salts. The compounds are useful for treating diseases associated with impaired mitochondrial function in an animal.

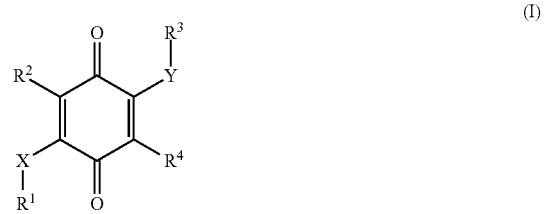

(I)

8 Claims, 10 Drawing Sheets

(56) References Cited

FOREIGN PATENT DOCUMENTS

| WO | 2011103536 A1 | 8/2011 |
|---|---|---|
| WO | 2012022467 A2 | 2/2012 |

OTHER PUBLICATIONS

European Search Report, for European Application No. 13846151. 2, 8 pages, May 19, 2016.
Mahendran, et al., "Synthesi s and 1-15 Evaluation of Analgesic and Anti-inflammatory Activities of Most Active Free Radical Scavenging Derivatives of Embelin-A Structure-Activity Relationship", Chemical and Pharmaceutical Bulletin, vol. 59(8), 913-919 (2011).
Schill, et al., "Makrocyclische Lactame als Madelle fur das Ansamycin Geldanamycin", Justus Liebigs Annalen Der Chemie, vol. 1977(2), 288-296 (1997). [English Abstract].
Ahn, et al., "Design of a Flexible Cell-Based Assay for the Evaluation of Heat Shock Protein 70 Expression Modulators", Assay Drug Dev. Technol., Jun. 2011, 9(3):236-246.
Bencze, et al., "Human frataxin: iron and ferrochelatase binding surface", J. C. S. Chem. Commun., May 2007, 14(18):1798-1800.
Boduszek, et al., "A New Method for the Preparation of Pyridine-4-phosphonic Acids", Synthesis, 1979, year 1979, Issue 6, 452-453.
Bradley, et al., "Clinical, biochemical and molecular genetic correlations in Friedreich's ataxia", Hum. Mol. Genet., 2000, 9(2):275-282.
Bulteau, et al., "Frataxin Acts as an Iron Chaperone Protein to Modulate Mitochondrial Aconitase Activity", Science, Jul. 2004, 305(5681):242-245.
Campuzano, et al., "Frataxin is Reduced in Friedreich Ataxia Patients and is Associated with Mitochondrial Membranes", Hum. Mol. Genet., 1997, 6(11):1771-1780.
Campuzano, et al., "Friedreich's ataxia: autosomal recessive disease caused by an intronic GAA triplet repeat expansion", Science, Mar. 1996, 271(5254):1423-7.
Dimauro, et al., "Mitochondrial DNA mutations in human disease", Am. J. Med Genet., 2001, 106(1):18-26.
Drummen, et al., "C11-BODIPY(581/591), an oxidation-sensitive fluorescent lipid peroxidation probe: (micro) spectroscopic characterization and validation of methodology", Free Radic. Biol. Med., Aug. 2002, 33(4):473-490.
Encinas, et al., "Sequential treatment of SH-SY5Y cells with retinoic acid and brain-derived neurotrophic factor gives rise to fully differentiated, neurotrophic factor-dependent, human neuron-like cells", J. Neurochem., Sep. 2000, 75 (3):991-1003.
Gonzalez-Cabo, et al., "Frataxin interacts functionally with mitochondrial electron transport chain proteins", Hum. Mol. Genet., Aug. 2005, 14(15):2091-2098.
Griffith, et al., "Potent and specific inhibition of glutathione synthesis by buthionine sulfoximine (S-n-butyl homocysteine sulfoximine)", J. Biol. Chem., Aug. 1979, 254(16):7558-7560.
Hamada, et al., "Synthesis and inhibitory action of novel acetogenin mimics with bovine heart mitochondrial complex I ", Biochemistry, Mar. 2004, 43(12):3651-3658.
Huezo, et al., "Microtiter Cell-Based Assay for Detection of Agents that Alter Cellular Levels of Her2 and EGFR", Chem. Biol., Jul. 2003, 10(7):629-634.
Itoh, et al., "The substitution of 5-halo-1,2,3-triazines with electrolytically generated superoxide", Tetrahedron, 1991, 47(25):4317-4324.
James, et al., "Interactions of Mitochondria-targeted and Untargeted Ubiquinones with the Mitochondrial Respiratory chain and Reactive Oxygen Species: Implications for the use of exogenous ubiquinones as therapies and experimental tools", J. Biol. Chem., Jun. 2005, 280(22):21295-21312.
Jauslin, et al., "A cellular model for Friedreich Ataxia reveals small-molecule glutathione peroxidase mimetics as novel treatment strategy", Hum. Mol. Genet., Nov. 2002, 11(24):3055-3063.
Kayed, et al., "Common structure of soluble amyloid oligomers implies common mechanism of pathogenesis", Science, Apr. 2003, 300(5618):486-489.
Khdour, et al., "An acetate prodrug of a pyridinol-based vitamin E analogue", Pharm. Res, Nov. 2011, 28(11):2896-2909.
Kuypers, et al., "Parinaric acid as a sensitive fluorescent probe for the determination of lipid peroxidation., Biochimica et Biophysica Acta", Sep. 1987, 921(2):266-274.
Lamarche, et al., "The cardiomyopathy of Friedreich's ataxia: morphological observations in 3 cases", Can. J. Neurosci., 1980, 7(4):389-396.
Lambert, et al., "Diffusible, nonfibrillar ligands derived from A$\beta$1-42 are potent central nervous system neurotoxins", Proc. Nat. Acad. Sci. USA., May 1998, 95(11):6448-6453.
Lebel, et al., "Evaluation of the probe 2',7'-dichlorofluorescin as an indicator of reactive oxygen species formation and oxidative stress", Chem. Res. Toxicol., 1992, 5(2):227-231.
Leonard, et al., "Mitochondrial respiratory chain disorders I: mitochondrial DNA defects", Lancet, 2000, 355 (9200):299-304.
Lin, et al., "A nitrogen-containing 3-alkyl-1,4-benzoquinone and a gomphilactone derivative from Embelia ribes", J. Nat. Prod., Nov. 2006, 69(11):1629-1632.
Matsuno-Yagi, et al., "Studies on the mechanism of oxidative phosphorylation: Catalytic site cooperativity in ATP synthesis", J. Biol. Chem., 1985, 260(27):14424-14427.
McErlean, et al., "First Synthesis of N-(3-Carboxylpropyl)-5-amino-2-hydroxy-3- tridecyl-1,4-benzoquinone, an Unusual Quinone Isolated from Embelia ribes", Journal of Organic Chemistry, Dec. 2007, 72(26):10298-10301.
Ogawa, et al., "Hydroxybenzoquinones from Myrsinaceae Plants. III. The Structures of 2-Hydroxy-5-methoxy-3-pentadecenylbenzoquinone and Ardisiaquinones A, B and C from Ardisia spp", Chemical and Pharmaceutical Bulletin, Dec. 1967, 16(9):1709-1720.
Ogawa, "Hydroxybenzoquinones from myrsinaceae plants-II.: Distribution among myrsinaceae plants in Japan., Phytochemistry", May 1968, 7(5):773-782.
Pap, et al., "Ratio-fluorescence microscopy of lipid oxidation in living cells using C11-BODIPY581/591", FEBS Letters, Jun. 1999, 453(3):278-282.
Park, et al., "Yeast frataxin sequentially chaperones and stores iron by coupling protein assembly with iron oxidation", J. Biol. Chem., Aug. 2003, 278(33):31340-51.
Patent Cooperation Treaty, International Searching Authority, Search Report and Written Opinion for PCT/US2013/64359, 9 pages, Feb. 10, 2014.
Poigny, et al., "Total synthesis of maesanin and analogues", Tetrahedron, Dec. 1998, 54(49):14791-14802.
Quinzii, et al., "Respiratory chain dysfunction and oxidative stress correlate with severity of primary CoQ10 deficiency", FASEB J., Jun. 2008, 22(6):1874-1885.
Robinson, "Nonviability of cells with oxidative defects in galactose medium: A screening test for affected patient fibroblasts", Biochem. Med. Metab. Biol., Oct. 1992, 48(2):122-126.
Smith, et al., "Preparation, properties, and conditions for assay of mitochondria: Slaughterhouse material, small-scale", Methods Enzymol., 1967, 10:81-86.
Stine, et al., "In vitro characterization of conditions for amyloid-beta peptide oligomerization and fibrillogenesis", Chem., Mar. 2003, 278(13):11612-11622.
Tikkanen, "Mutagenicity of natural naphthoquinones and benzoquinones in the Salmonella/microsome test", Mutat. Res., Oct. 1983, 124(1):25-34.
Trounce, et al., "Assessment of mitochondrial oxidative phosphorylation in patient muscle biopsies, lymphoblasts, and transmitochondrial cell lines", Methods Enzymol., 1996, 264:484-509.
Wijtmans, et al., "Synthesis and Reactivity of Some 6-Substituted-2,4-dimethyl-3-pyridinols, a Novel Class of Chain-Breaking Antioxidants", J. Org. Chem. Dec. 2004, 69(26):9215-9223.
Wilson, "Frataxin and frataxin deficiency in Friedreich's ataxia", J. Neurol. Sci., Mar. 2003, 207(1-2):103-105.
Wilson et al., "Respiratory deficiency due to loss of mitochondrial DNA in yeast lacking the frataxin homologue", Nature Genetics, Aug. 1997, 16(4):352-357.

(56) References Cited

OTHER PUBLICATIONS

Wu, et al., "Autoxidation of phosphatidylcholine liposomes", Lipids, Jun. 1982, 17(6):403-413.
Yamada, et al., "Immunochemical detection of a lipofuscin-like fluorophore derived from malondialdehyde and lysine", J. Lipid Res., Aug. 2001, 42(8):1187-1196.
Yin, et al., "Biochemical basis of lipofuscin, ceroid, and age pigment-like fluorophores", Free Rad. Biol. Med., 1996, 21(6):871-888.
Yoon, et al., "Frataxin-mediated Iron Delivery to Ferrochelatase in the Final Step of Heme Biosynthesis", J. Biol. Chem., Jun. 2004, 279(25):25943-25946.
Yoon, et al., "Iron-sulfur cluster biosynthesis. Characterization of frataxin as an iron donor for assembly of [2Fe—2S] clusters in ISU-type proteins", J. Am. Chem. Soc., May 2003, 125(20):6078-6084.
Yoshihira, et al., "Hydroxybenzoquinones from Myrsinaceae Plants. IV. Further Confirmation of the Structures of Ardisiaquinones and Some Observations on Alkylaminobenzoquinone Derivatives", Chemical and Pharmaceutical Bulletin, 1968, 16(12):2383-2389.
CAS, RN 108022-57-7, STN Entry Date, May 9, 1987.
Nishikawa, et al., "Growth Inhibition of Hepatoma Cells Induced by Vitamin K and Its Analogs", The Journal of Biological Chemistry, vol. 270, No. 47, p. 28304-28310 (1995).
Xing, et al., "Sigmatropic Reactions of the Aziridinyl Semiquinone Species. Why Aziridinyl Benzoquinones Are Metabolically More Stable than Aziridinyl Indoloquinones", Biochemistry 39, 10770-10780 (2000).

\* cited by examiner

A

B

MULTIFUNCTIONAL RADICAL QUENCHERS

PRIORITY OF INVENTION

This application claims priority to U.S. Provisional Application No. 61/712,170, filed 10 Oct. 2012. The entire content of this provisional application is hereby incorporated herein by reference.

FIELD OF THE INVENTION

The present disclosure provides biologically active compounds multifunctional radical quenchers of formula (I) and pharmaceutically acceptable salts thereof, compositions comprising these compounds, and methods of using these compounds in a variety of applications, such as treatment or suppression of diseases associated with impaired mitochondrial function resulting in diminished ATP production and/or oxidative stress and/or lipid peroxidation.

BACKGROUND OF THE INVENTION

Mitochondria are intracellular organelles responsible for a number of metabolic transformations and regulatory functions. They produce much of the ATP employed by eukaryotic cells. They are also the major source of free radicals and reactive oxygen species that cause oxidative stress. Consequently, mitochondrial defects are damaging, particularly to neural and muscle tissues which have high energy level demands. Thus, energetic defects have been implicated in forms of movement disorders, cardiomyopathy, myopathy, blindness, and deafness (DiMauro et al. (2001) *Am. J. Med. Genet.* 106, 18-26; Leonard et al. (2000) *Lancet.* 355, 299-304). There are a number of mitochondrial diseases resulting from both nuclear and mitochondrial genetic defects, and the underlying biochemistries of these diseases tend to be rather similar. They include increased lactate production, diminished respiration and ATP production, and reflect the consequences of oxidative stress.

SUMMARY OF THE INVENTION

The invention provides novel compounds that are useful for the treatment or suppression of diseases associated with impaired mitochondrial function resulting in diminished ATP production and/or oxidative stress and/or lipid peroxidation.

Accordingly the invention provides a compound of the invention which is a compound of formula I:

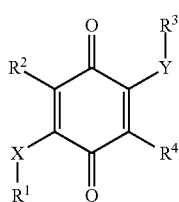

(I)

wherein:
X is $NR_a$, S, O, or $—C(=O)N(R_a)—$;
$R^1$ is H or a $C_1$-$C_{20}$ straight or branched, saturated or unsaturated carbon chain, wherein one or more carbon atoms can optionally be replaced with —O—, —NH—, a divalent phenyl group or a divalent $C_3$-$C_6$ cycloalkyl group; wherein $R^1$ can be optionally substituted with one or more groups independently selected from halo, aryl, and oxo (=O);

$R^2$ is H, cyano, nitro, halo, aryloxy, $—NR_bR_c$, $—C(=O)NR_bR_c$, $—C=(O)OR_d$, or a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$ cycloalkyl group; wherein $R^2$ can be optionally substituted with one or more groups independently selected from halo, oxo (=O), carboxy, $C_1$-$C_3$ alkyl, $C_1$-$C_3$ alkoxy, nitro, $—SO_3H$, or tetrazolyl;

Y is absent, and $R^3$ is H, cyano, nitro, or halo; or Y is absent, $NR_a$, S, or O, and $R^3$ is H, aryl, or a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$ cycloalkyl group; wherein $R^3$ can be further optionally substituted with one or more groups independently selected from halo, oxo (=O), carboxy, $C_1$-$C_3$ alkyl, $C_1$-$C_3$ alkoxy, nitro, $—SO_3H$, or tetrazolyl;

$R^4$ is H or a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$ cycloalkyl group; wherein $R^4$ can be further optionally substituted with one or more groups independently selected from halo, oxo (=O), carboxy, $C_1$-$C_3$ alkyl, $C_1$-$C_3$ alkoxy, nitro, $—SO_3H$, or tetrazolyl; or $R^1$ and $R^4$ taken together form a $C_3$-$C_{20}$ straight or branched, saturated or unsaturated carbon chain that can be optionally substituted with one or more groups independently selected from halo and oxo (=O); and each $R_a$ is independently H, $C_1$-$C_{20}$ alkyl, $C_2$-$C_{20}$ alkenyl, $C_2$-$C_{20}$ alkynyl, $C_1$-$C_{20}$ alkanoyl, aryl, or aryl$C_1$-$C_{20}$ alkyl; wherein any $C_1$-$C_{20}$ alkyl, $C_2$-$C_{20}$ alkenyl, $C_2$-$C_{20}$ alkynyl, $C_1$-$C_{20}$ alkanoyl, aryl, and aryl$C_1$-$C_{20}$ alkyl is optionally substituted with one or more halo or $C_1$-$C_3$ alkoxy;

each $R_b$ and $R_c$ is independently $C_1$-$C_{20}$ alkyl, $C_2$-$C_{20}$ alkenyl, $C_2$-$C_{20}$ alkynyl, or aryl, wherein any $C_1$-$C_{20}$ alkyl, $C_2$-$C_{20}$ alkenyl, $C_2$-$C_{20}$ alkynyl, and aryl of $R_b$ and $R_c$ is optionally substituted with one or more halo; or $R_b$ and $R_c$ together with the nitrogen to which they are attached form a morpholino, piperazino, pyrrolidino or piperidino;

each $R_d$ is independently H, $C_1$-$C_{20}$ alkyl, $C_2$-$C_{20}$ alkenyl, $C_2$-$C_{20}$ alkynyl, or aryl, wherein any $C_1$-$C_{20}$ alkyl, $C_2$-$C_{20}$ alkenyl, $C_2$-$C_{20}$ alkynyl, and aryl is optionally substituted with one or more halo;

or a salt thereof.

The invention also provides a pharmaceutical composition comprising a compound of formula I or a pharmaceutically acceptable salt thereof, and a pharmaceutically acceptable carrier.

The invention also provides a method for treating or preventing a disease associated with impaired mitochondrial function in an animal comprising administering a compound of formula I or a pharmaceutically acceptable salt thereof to the animal.

The invention also provides a method for treating or preventing Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome, comprising administering a compound of formula I or a pharmaceutically acceptable salt thereof to the animal.

The invention also provides a method for treating or preventing obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, or Leigh syndrome, comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of a disease associated with impaired mitochondrial function.

The invention also provides a compound of formula I or a pharmaceutically acceptable salt thereof for the prophylactic or therapeutic treatment of Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome.

The invention also provides a compound of formula I or a pharmaceutically acceptable salt thereof for the prophylactic or therapeutic treatment of obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, or Leigh syndrome.

The invention also provides the use of a compound of formula I or a pharmaceutically acceptable salt thereof to prepare a medicament for treating a disease associated with impaired mitochondrial function in an animal.

The invention also provides the use of a compound of formula I or a pharmaceutically acceptable salt thereof to prepare a medicament for treating Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome in an animal.

The invention also provides the use of a compound of formula I or a pharmaceutically acceptable salt thereof to prepare a medicament for treating obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, or Leigh syndrome in an animal.

The invention also provides processes and intermediates disclosed herein that are useful for preparing a compound of formula I or a salt thereof.

Some of the compounds of the invention increase ATP concentration in $CoQ_{10}$ deficient cells. In addition, the compounds of the invention inhibit lipid peroxidation and prevent reactive oxygen species (ROS) production in cells depleted of the antioxidant glutathione (GSH) using the chemical diethyl maleate. Moreover, these compounds prevented ROS dependent cell death after the cells were depleted of GSH. The antioxidant potential of the compounds described above is significantly increased compared to that of a-tocopherol and idebenone; therefore, these compounds have the potential of improved efficacy in clinical applications compared to a-tocopherol and idebenone.

DETAILED DESCRIPTION

Figure 1:
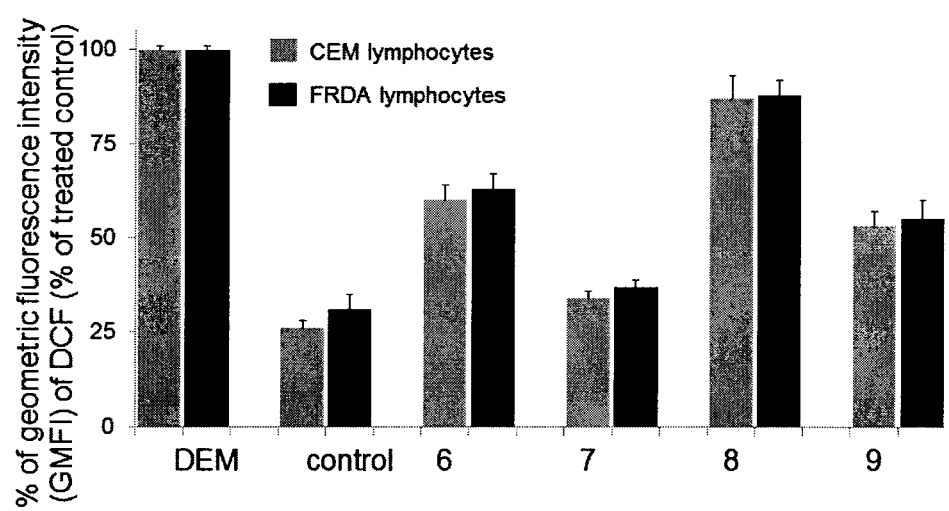
FIG. 1. Flow cytometric analysis of CEM leukemia lymphocytes (gray bars) and FRDA lymphocytes (black bars) stained with dichlorodihydrofluorescein diacetate (DCFH-DA) for 20 min, following pretreatment with the test compounds at 5 µM concentration for 16 h, and subsequent treatment with diethyl maleate (DEM) for 60 or 80 min to induce the production of ROS in CEM and FRDA lymphocytes, respectively. Data shown represent the mean±SEM of two different experiments run as duplicates.
Figure 2:
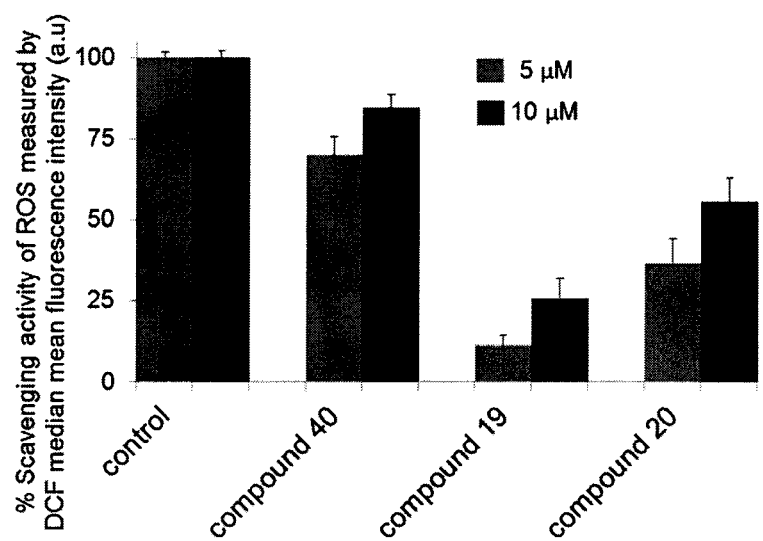
FIG. 2. Representative flow cytometric analysis of ROS production in FRDA lymphocytes. Following pretreatment with the indicated compounds (5 and 10 µM) for 16 h, the cells were treated with 5 mM diethyl maleate (DEM) for 80 min to deplete glutathione. The cells were washed in phosphate-buffered saline and suspended in phosphate-buffered saline containing 20 mM glucose. Cells were loaded with 10 µM dichlorodihydrofluorescein diacetate (DCFH-DA) for 20 min, and the green fluorescence (DCF) was measured by flow cytometry (C6 Accuri, BD Biosciences, San Jose, Calif.), using a 488 nm excitation laser and the FL1-H channel 530±15 nm emission filter. The figure shows a representative example of three independent experiments. A total of 10,000 events was recorded for each sample and analyzed (C6 Accuri software, BD Biosciences). The bar graph represents ROS % scavenging activity. Data are expressed as the mean±SEM (n=3).

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "animal" as used herein includes mammals, such as humans.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thioxo groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-onyl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin-3(4H)-on-5-yl, 2H-benzo[b][1,4]oxazin3(4H)-on-6-yl, 2H-benzo[b][1,4]oxazin-3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "saturated" as used herein means the referenced chemical structure does not contain any multiple carbon-carbon bonds. For example, a saturated cycloalkyl group as defined herein includes cyclohexyl, cyclopropyl, and the like.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

The term, "divalent" when used for example with respect to a phenyl ring or a cycloalkyl group means the phenyl ring or cycloalkyl group is attached to the remainder of the molecule through two positions. Examples of divalent phenyl include the following groups:

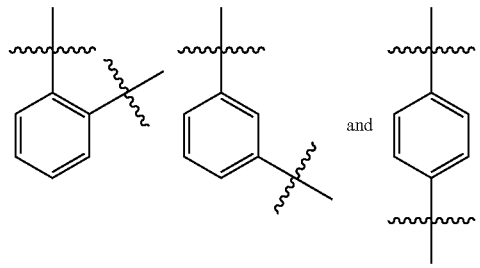 [SMILES: *c1ccccc1* ; *c1cccc(*)c1 ; *c1ccc(*)cc1]

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents A specific value for X is $NR_a$ or —C(=O)N($R_a$)—.

A specific value for X is $NR_a$.

A specific value for $R_a$ is H or methyl.

A specific value for X is S or O.

A specific value for $R^1$ is a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^1$ can be optionally substituted with one or more groups independently selected from halo, aryl, and oxo (=O).

A specific value for $R^1$ is a $C_1$-$C_{20}$ straight or branched, saturated or unsaturated carbon chain, wherein one or more carbon atoms can optionally be replaced with —O—, —NH—, or a divalent phenyl group; wherein $R^1$ can be optionally substituted with one or more groups independently selected from halo, aryl, and oxo (=O);

A specific value for $R^1$ is a $C_1$-$C_{20}$ straight or branched, saturated or unsaturated carbon chain, wherein one or more carbon atoms can optionally be replaced with —O— or —NH—; wherein $R^1$ can be optionally substituted with one or more groups independently selected from halo, aryl, and oxo (=O).

A specific value for $R^1$ is a $C_1$-$C_{20}$ straight or branched, saturated or unsaturated carbon chain, wherein one or more carbon atoms can optionally be replaced with —O—; wherein $R^1$ can be optionally substituted with one or more groups independently selected from halo, aryl, and oxo (=O).

A specific value for $R^1$ is H, $C_1$-$C_{20}$alkyl, $C_2$-$C_{20}$alkenyl, $C_2$-$C_{20}$alkynyl, or $C_1$-$C_{20}$alkanoyl.

A specific value for $R^1$ is H, $C_1$-$C_6$alkyl, $C_2$-$C_6$alkenyl, $C_2$-$C_6$alkynyl, or $C_1$-$C_6$alkanoyl.

A specific value for $R^1$ is 3-tert-butoxycarbonylpropyl, 3-carboxypropyl, 3-(benzyloxycarbonyl)propyl, 3-(butoxycarbonyl)propyl, 3-(hexyloxycarbonyl)propyl, hexyl, methyl, or 5-hexen-1-yl.

A specific value for $R^1$ and $R^4$ taken together is a $C_3$-$C_{20}$ straight or branched, saturated or unsaturated carbon chain that can be optionally substituted with one or more groups independently selected from halo and oxo (=O).

A specific value for $R^1$ and $R^4$ taken together is a $C_{20}$ saturated or unsaturated carbon chain that can be optionally substituted with one or more groups independently selected from halo and oxo (=O).

A specific value for $R^1$ and $R^4$ taken together is —(CH$_2$)$_4$CH=CH(CH$_2$)$_9$—, or —(CH$_2$)$_{15}$—.

A specific value for $R^2$ is H, cyano, nitro, halo, aryloxy, —O$C_1$-$C_{20}$alkyl, —O$C_2$-$C_{20}$alkenyl, —O$C_2$-$C_{20}$alkynyl, —N$R_b$$R_c$, —C(=O)N$R_b$$R_c$, or —C(=O)O$R_d$.

A specific value for $R^2$ is H, cyano, nitro, halo, aryloxy, —O$C_1$-$C_{20}$alkyl, —O$C_2$-$C_6$alkenyl, —O$C_2$-$C_6$alkynyl, —N$R_b$$R_c$, —C(=O)N$R_b$$R_c$, or —C(=O)O$R_d$.

A specific group of compounds are compounds wherein Y is absent, and $R^3$ is H, cyano, nitro, or halo.

A specific group of compounds are compounds wherein Y is $NR_a$, S, or O, and $R^3$ is H.

A specific group of compounds are compounds wherein Y is $NR_a$, S, or O, and $R^3$ is a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^3$ can be further optionally substituted with one or more groups independently selected from halo, oxo (=O), carboxy, $C_1$-$C_3$alkyl, $C_1$-$C_3$alkoxy, nitro, —SO$_3$H, or tetrazolyl.

A specific group of compounds are compounds wherein Y is $NR_a$, S, or O, and $R^3$ is a $C_1$-$C_{20}$ straight or branched, saturated or unsaturated carbon chain that can be optionally substituted with one or more groups independently selected from halo, oxo (=O), carboxy, $C_1$-$C_3$alkyl, $C_1$-$C_3$alkoxy, nitro, —SO$_3$H, or tetrazolyl.

A specific group of compounds are compounds wherein Y and $R^3$ taken together are H, cyano, nitro, halo, aryloxy, —O$C_1$-$C_{20}$alkyl, —N$R_a$($C_1$-$C_{20}$alkyl), —N$R_a$(aryl), —$C_1$-$C_{20}$alkyl, —$C_2$-$C_{20}$alkenyl, or —$C_2$-$C_{20}$alkynyl.

A specific group of compounds are compounds wherein Y and $R^3$ taken together are hydroxy or methoxy.

A specific value for $R^4$ is a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^4$ can be further optionally substituted with one or more groups independently selected from halo, oxo (=O), carboxy, $C_1$-$C_3$alkyl, $C_1$-$C_3$alkoxy, nitro, —SO$_3$H, or tetrazolyl.

A specific value for $R^4$ is a $C_1$-$C_{20}$ straight or branched, saturated or unsaturated carbon chain, that can be further optionally substituted with one or more groups independently selected from halo, oxo (=O), carboxy, $C_1$-$C_3$alkyl, $C_1$-$C_3$alkoxy, nitro, —SO$_3$H, or tetrazolyl.

A specific value for $R^4$ is a $C_1$-$C_{20}$ straight or branched, saturated or unsaturated carbon chain.

A specific value for $R^4$ is a $C_1$-$C_{20}$alkyl, $C_2$-$C_{20}$alkenyl, or $C_2$-$C_{20}$alkynyl.

A specific value for $R^4$ is tridecyl or 10-undecen-1-yl.

A specific compound is a compound of formula Ia:

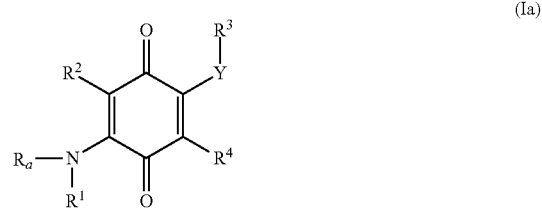

(Ia)

wherein:

$R^1$ is H, $C_1$-$C_{20}$alkyl, $C_2$-$C_{20}$alkenyl, $C_2$-$C_{20}$alkynyl, or $C_1$-$C_{20}$alkanoyl;

$R^2$ is H, cyano, nitro, halo, aryloxy, —O$C_1$-$C_{20}$alkyl, —O$C_2$-$C_{20}$alkenyl, —O$C_2$-$C_{20}$alkynyl, —N$R_b$$R_c$, —C(=O)N$R_b$$R_c$, or —C(=O)O$R_d$;

Y and $R^3$ taken together are H, cyano, nitro, halo, aryloxy, —O$C_1$-$C_{20}$alkyl, —N$R_a$($C_1$-$C_{20}$alkyl), —N$R_a$(aryl), —$C_1$-$C_{20}$alkyl, —$C_2$-$C_{20}$alkenyl, or —$C_2$-$C_{20}$alkynyl.

$R^4$ is a $C_1$-$C_{20}$alkyl, $C_2$-$C_{20}$alkenyl, or $C_2$-$C_{20}$alkynyl; and $R_a$ is H, $C_1$-$C_{20}$alkyl, $C_2$-$C_{20}$alkenyl, $C_2$-$C_{20}$alkynyl, or $C_1$-$C_{20}$alkanoyl;

or a salt thereof.

A specific compound is a compound of formula Ia:

(Ia)

wherein:
R$^1$ is H, C$_1$-C$_6$alkyl, C$_2$-C$_6$alkenyl, C$_2$-C$_6$alkynyl, or C$_1$-C$_6$alkanoyl;
R$^2$ is H, cyano, nitro, halo, aryloxy, —OC$_1$-C$_6$alkyl, —OC$_2$-C$_6$alkenyl, —OC$_2$-C$_6$alkynyl, —NR$_b$R$_c$, —C(=O)NR$_b$R$_c$, or —C(=O)OR$_d$;
Y and R$^3$ taken together are H, cyano, nitro, halo, aryloxy, —OC$_1$-C$_6$alkyl, —NR$_a$(C$_1$-C$_6$alkyl), —NR$_a$(aryl), —C$_1$-C$_{20}$alkyl, —C$_2$-C$_{20}$alkenyl, or —C$_2$-C$_{20}$alkynyl.
R$^4$ is a C$_1$-C$_{20}$alkyl, C$_2$-C$_{20}$alkenyl, or C$_2$-C$_{20}$alkynyl; and
R$_a$ is H, C$_1$-C$_6$alkyl, C$_2$-C$_6$alkenyl, C$_2$-C$_6$alkynyl, or C$_1$-C$_6$alkanoyl;
or a salt thereof.

A specific compound is a compound of formula Ib:

(Ib)

wherein:
R$^2$ is H, cyano, nitro, halo, aryloxy, —OC$_1$-C$_{20}$alkyl, —OC$_2$-C$_{20}$alkenyl, —OC$_2$-C$_{20}$alkynyl, —NR$_b$R$_c$, —C(=O)NR$_b$R$_c$, or —C(=O)OR$_d$;
Y and R$^3$ taken together are H, cyano, nitro, halo, aryloxy, —OC$_1$-C$_{20}$alkyl, —NR$_a$(C$_1$-C$_{20}$alkyl), —NR$_a$(aryl), —C$_1$-C$_{20}$alkyl, —C$_2$-C$_{20}$alkenyl, or —C$_2$-C$_{20}$alkynyl.
R$^4$ is a C$_1$-C$_{20}$alkyl, C$_2$-C$_{20}$alkenyl, or C$_2$-C$_{20}$alkynyl;
R$_a$ is H, C$_1$-C$_{20}$alkyl, C$_2$-C$_{20}$alkenyl, C$_2$-C$_{20}$alkynyl, or C$_1$-C$_{20}$alkanoyl;
R$_x$ is C$_1$-C$_{20}$alkyl, C$_2$-C$_{20}$alkenyl, C$_2$-C$_{20}$alkynyl, aryl, —OC$_1$-C$_{20}$alkyl, —OC$_2$-C$_{20}$alkenyl, —OC$_2$-C$_{20}$alkynyl, aryloxy, —N(H)C$_1$-C$_{20}$alkyl, —N(H)C$_2$-C$_{20}$alkenyl, —N(H)C$_2$-C$_{20}$alkynyl, or —N(H)aryl;
or a salt thereof.

A specific compound is a compound of formula Ib:

(Ib)

wherein:
R$^2$ is H, cyano, nitro, halo, aryloxy, —OC$_1$-C$_6$alkyl, —OC$_2$-C$_6$alkenyl, —OC$_2$-C$_6$alkynyl, —NR$_b$R$_c$, —C(=O)NR$_b$R$_c$, or —C(=O)OR$_d$;
Y and R$^3$ taken together are H, cyano, nitro, halo, aryloxy, —OC$_1$-C$_6$alkyl, —NR$_a$(C$_1$-C$_6$alkyl), —NR$_a$(aryl), —C$_1$-C$_{20}$alkyl, —C$_2$-C$_{20}$alkenyl, or —C$_2$-C$_{20}$alkynyl.
R$^4$ is a C$_1$-C$_{20}$alkyl, C$_2$-C$_{20}$alkenyl, or C$_2$-C$_{20}$alkynyl;
R$_a$ is H, C$_1$-C$_6$alkyl, C$_2$-C$_6$alkenyl, C$_2$-C$_6$alkynyl, or C$_1$-C$_6$alkanoyl;
R$_x$ is C$_1$-C$_6$alkyl, C$_2$-C$_6$alkenyl, C$_2$-C$_6$alkynyl, aryl, —OC$_1$-C$_6$alkyl, —OC$_2$-C$_6$alkenyl, —OC$_2$-C$_6$alkynyl, aryloxy, —N(H)C$_1$-C$_6$alkyl, —N(H)C$_2$-C$_6$alkenyl, —N(H)C$_2$-C$_6$alkynyl, or —N(H)aryl;
or a salt thereof.

A specific value for C$_1$-C$_{20}$alkyl is for C$_1$-C$_6$alkyl.
A specific value for C$_2$-C$_{20}$alkenyl is C$_2$-C$_6$alkenyl.
A specific value for C$_2$-C$_{20}$alkynyl is C$_2$-C$_6$alkynyl.
A specific value for, C$_1$-C$_{20}$alkanoyl is C$_1$-C$_6$alkanoyl.
A specific value for R$^1$ is H, C$_1$-C$_6$alkyl, C$_2$-C$_6$alkenyl, C$_2$-C$_6$alkynyl, or C$_1$-C$_6$alkanoyl.
A specific compound of formula I is a compound wherein X—R$^1$ taken together are not —N(CH$_3$)$_2$.
A specific compound of formula I is a compound wherein Y—R$^3$ taken together are not OH.
A specific compound of formula I is a compound wherein R$^4$ is not a C$_{12}$-C$_{14}$ straight, saturated carbon chain.
A specific compound of formula I is a compound wherein R$^4$ is a C$_1$-C$_{20}$ straight or branched, saturated or unsaturated carbon chain, wherein one or more carbon atoms is replaced with —O—, —NH—, a divalent phenyl group, or a divalent C$_3$-C$_6$cycloalkyl group; wherein R$^4$ can be further optionally substituted with one or more groups independently selected from halo, oxo (=O), carboxy, C$_1$-C$_3$alkyl, C$_1$-C$_3$alkoxy, nitro, —SO$_3$H, or tetrazolyl.
A specific compound of formula I is a compound wherein R$^4$ is a C$_1$-C$_{20}$ straight or branched, unsaturated carbon chain, wherein one or more carbon atoms can optionally be replaced with —O—, —NH—, a divalent phenyl group, or a divalent C$_3$-C$_6$cycloalkyl group; wherein R$^4$ can be further optionally substituted with one or more groups independently selected from halo, oxo (=O), carboxy, C$_1$-C$_3$alkyl, C$_1$-C$_3$alkoxy, nitro, —SO$_3$H, or tetrazolyl.
A specific compound of formula I is a compound wherein R$^4$ is a C$_1$-C$_{10}$ straight or branched, saturated or unsaturated carbon chain, wherein one or more carbon atoms can optionally be replaced with —O—, —NH—, a divalent phenyl group, or a divalent C$_3$-C$_6$cycloalkyl group; wherein R$^4$ can be further optionally substituted with one or more groups independently selected from halo, oxo (=O), carboxy, C$_1$-C$_3$alkyl, C$_1$-C$_3$alkoxy, nitro, —SO$_3$H, or tetrazolyl.
A specific compound of formula I is a compound wherein R$^4$ is a C$_{15}$-C$_{20}$ straight or branched, saturated or unsaturated carbon chain, wherein one or more carbon atoms can optionally be replaced with —O—, —NH—, a divalent phenyl group, or a divalent C$_3$-C$_6$cycloalkyl group; wherein R$^4$ can be further optionally substituted with one or more groups independently selected from halo, oxo (=O), carboxy, C$_1$-C$_3$alkyl, C$_1$-C$_3$alkoxy, nitro, —SO$_3$H, or tetrazolyl.
A specific compound of formula I is a compound wherein:
X is NR$_a$, S, O, or —C(=O)N(R$_a$)—;
R$^1$ is H or a C$_1$-C$_{20}$ straight or branched, saturated or unsaturated carbon chain, wherein one or more carbon atoms can optionally be replaced with —O—, —NH—, a divalent phenyl group or a divalent C$_3$-C$_6$cycloalkyl group; wherein R$^1$ can be optionally substituted with one or more groups independently selected from halo, aryl, and oxo (=O);

$R^2$ is cyano, nitro, halo, aryloxy, —$NR_bR_c$, —$C(=O)NR_bR_c$, —$C(=O)OR_d$, or a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^2$ can be optionally substituted with one or more groups independently selected from halo, oxo (=O), carboxy, $C_1$-$C_3$alkyl, $C_1$-$C_3$alkoxy, nitro, —$SO_3H$, or tetrazolyl;

Y is absent, and $R^3$ is cyano, nitro, or halo; or Y is absent, $NR_a$, S, or O, and $R^3$ is a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$ cycloalkyl group; wherein $R^3$ can be further optionally substituted with one or more groups independently selected from halo, oxo (=O), carboxy, $C_1$-$C_3$alkyl, $C_1$-$C_3$alkoxy, nitro, —$SO_3H$, or tetrazolyl; and $R^4$ is a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^4$ can be further optionally substituted with one or more groups independently selected from halo, oxo (=O), carboxy, $C_1$-$C_3$alkyl, $C_1$-$C_3$alkoxy, nitro, —$SO_3H$, or tetrazolyl; or $R^1$ and $R^4$ taken together form a $C_3$-$C_{20}$ straight or branched, saturated or unsaturated carbon chain that can be optionally substituted with one or more groups independently selected from halo and oxo (=O).

A specific value for $R^1$ and X taken together is N-(3-tert-butoxycarbonylprop-1-yl)amino, N-(3-carboxyprop-1-yl)amino, N-(3-(benzyloxycarbonyl)prop-1-yl)amino, N-(3-(butoxycarbonyl)prop-1-yl)amino, N-(3-(hexyloxycarbonyl)prop-1-yl)amino, 1-hexylamino, dimethylamino, N-(3-tert-butoxycarbonylprop-1-yl)-N-methylamino, methoxy, N-(5-hexen-1-yl)amino, N-(3-(hexyloxycarbonyl)prop-1-yl)-N-methylamino, or N-(3-(propoxycarbonyl)prop-1-yl)amino.

A specific value for Y and $R^3$ taken together is hydroxyl, methoxy, 3-(tert-butoxycarbonyl)prop-1-yloxy, N-(3-(butoxycarbonyl)prop-1-yl)amino, N-(3-(hexyloxycarbonyl)prop-1-yl)amino, 3-(butoxycarbonyl)prop-1-yloxy, or 3-(hexyloxycarbonyl)prop-1-yloxy.

A specific value for $R^4$ is tridecyl, hexadecyl, or 10-undecen-1-yl.

A specific compound is selected from:

5

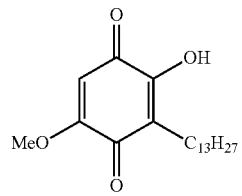

6

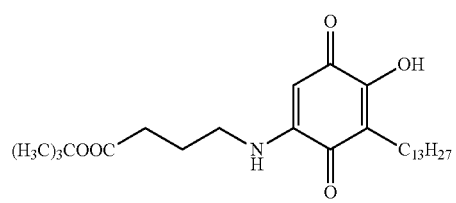

-continued

7

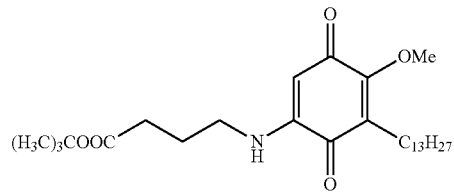

8

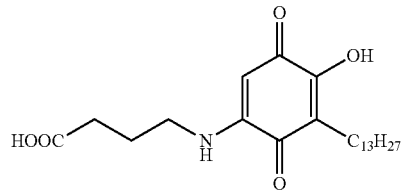

9

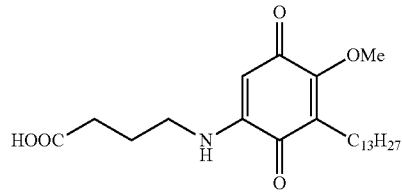

11

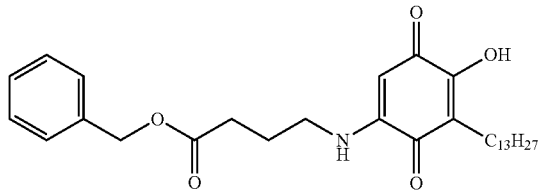

13

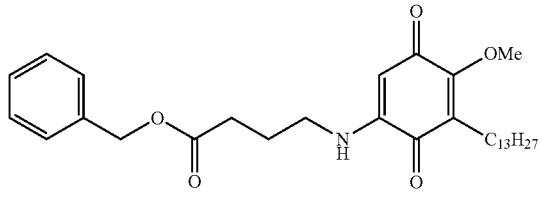

14

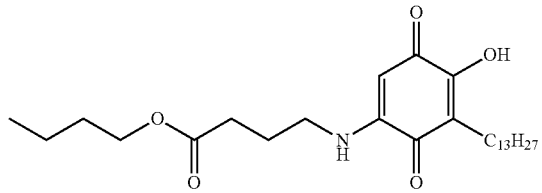

15

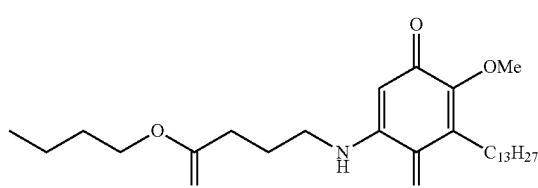

-continued
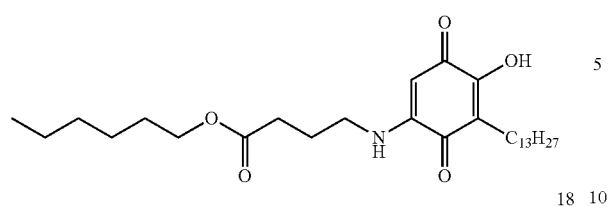
17
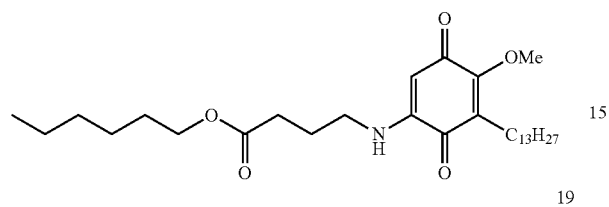
18
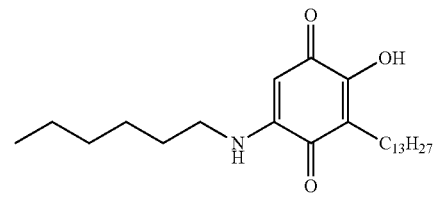
19
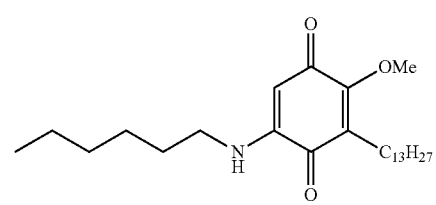
20
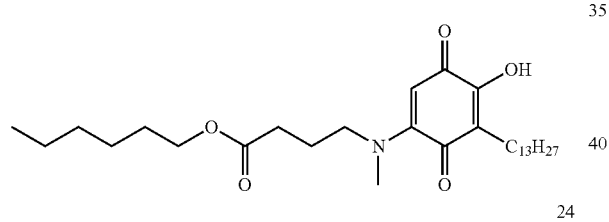
23
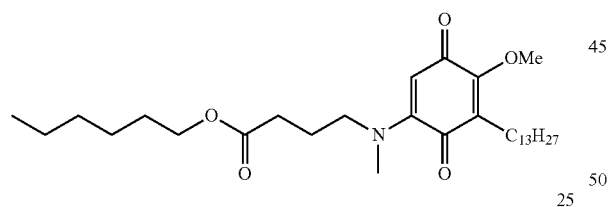
24
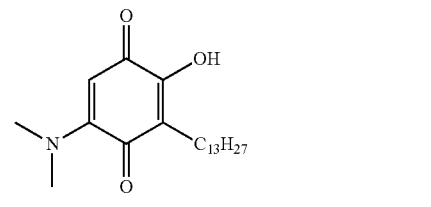
25
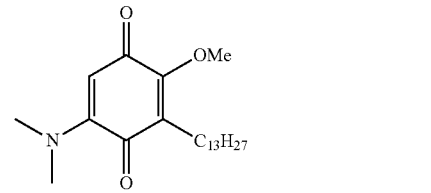
26
-continued
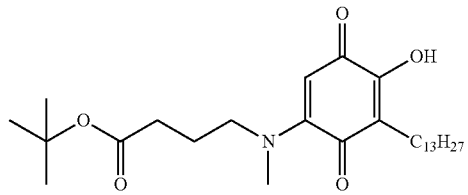
29
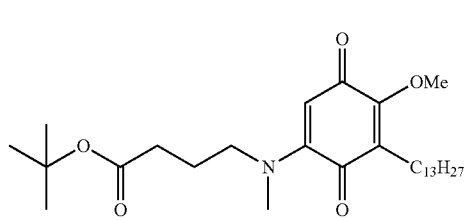
30
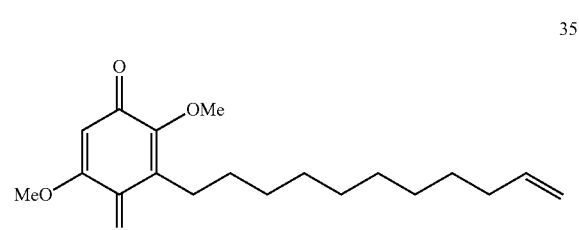
35
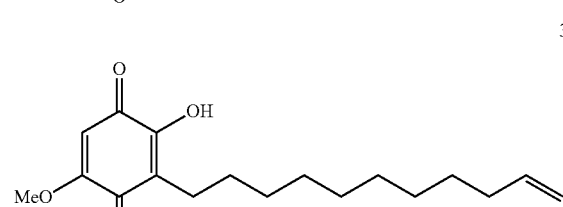
36
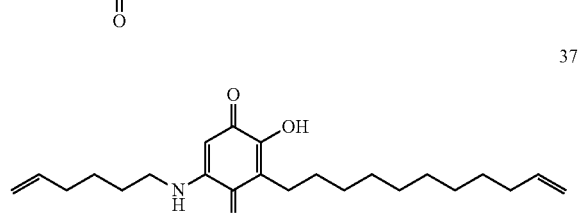
37
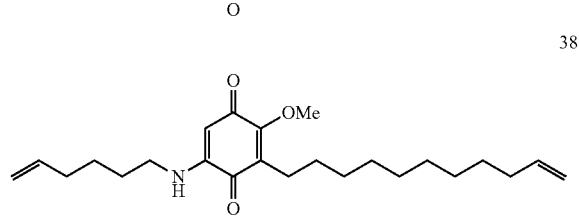
38
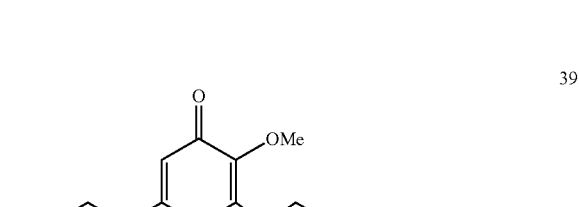
39
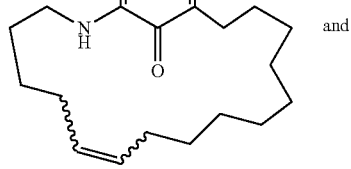
and -continued
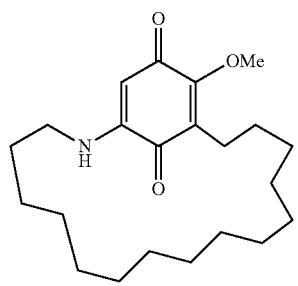
and salts thereof.
A specific compound is selected from:
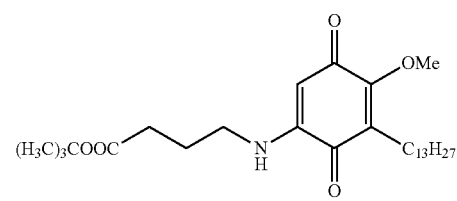
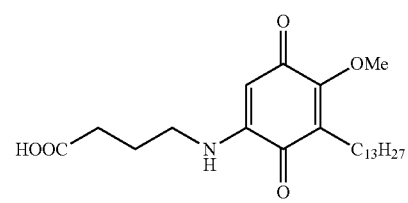
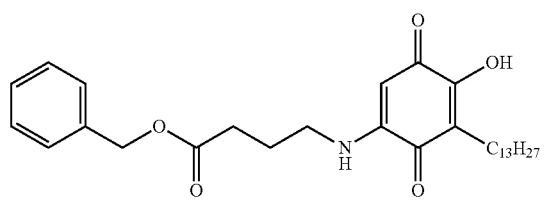
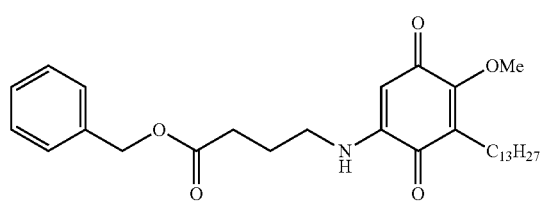
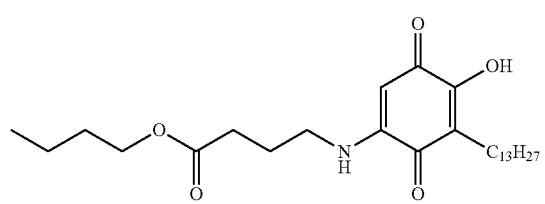
-continued
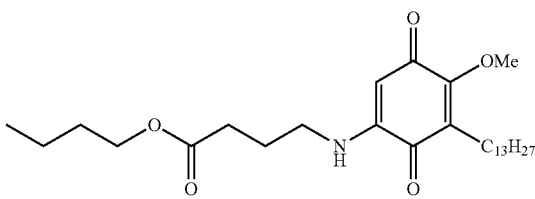
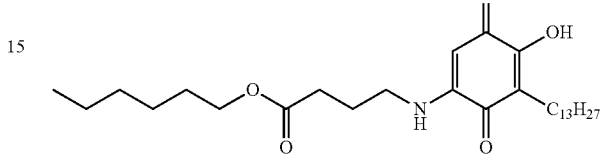
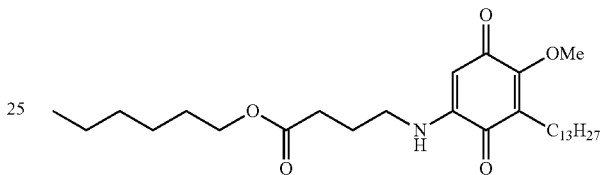
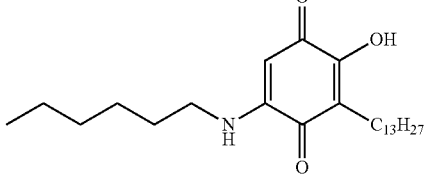
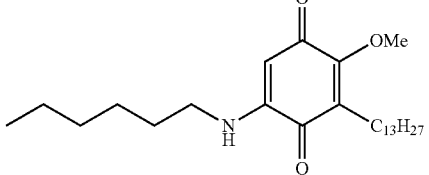
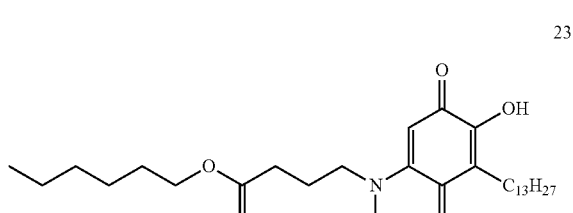
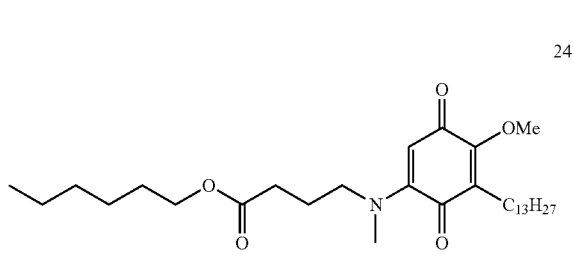

-continued
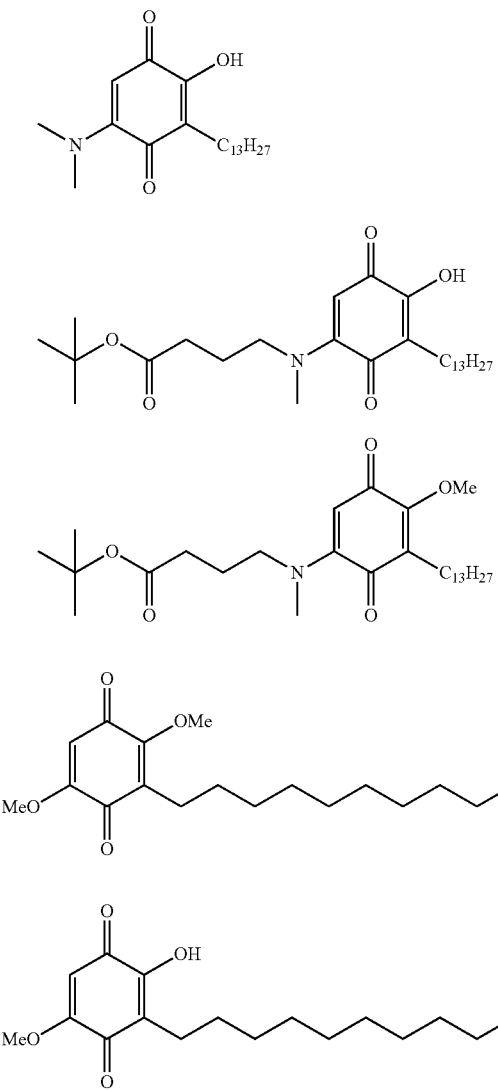
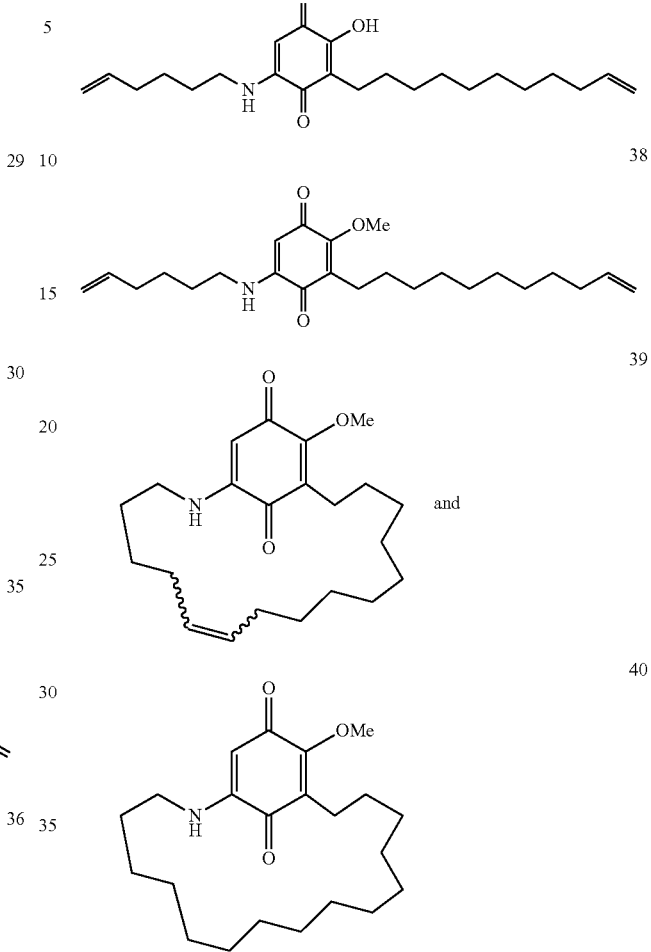
and salts thereof.
A specific compound is selected from:
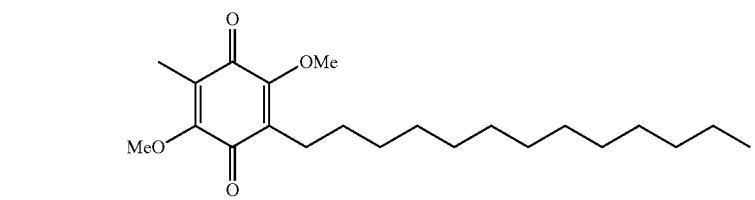
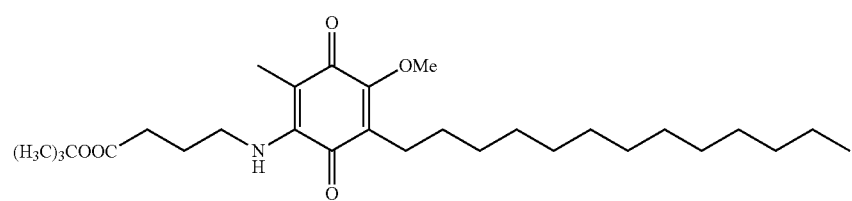

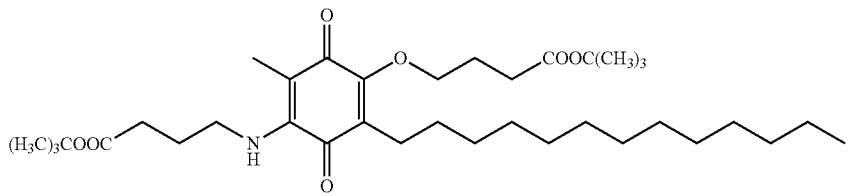
44
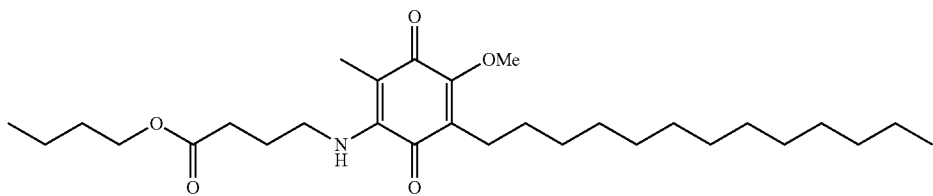
46
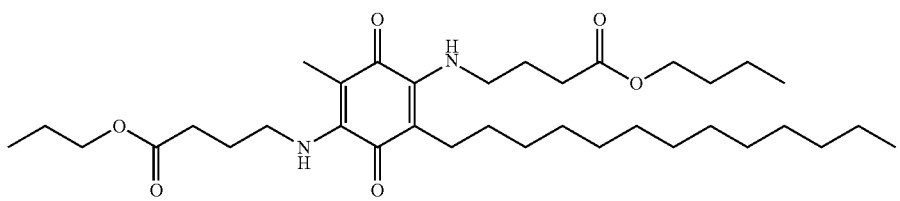
47
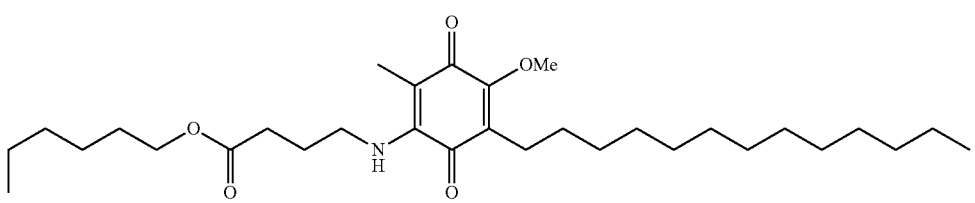
49
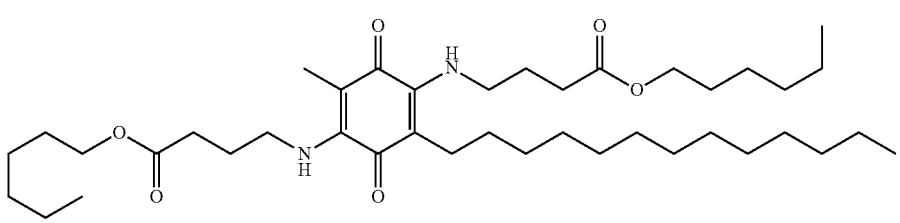
50
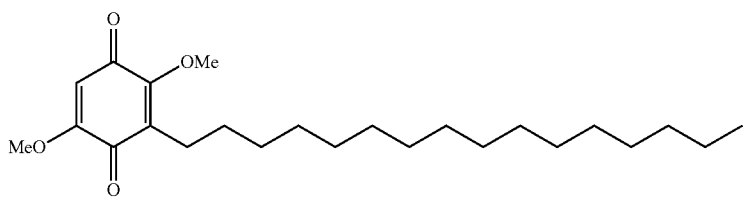
52
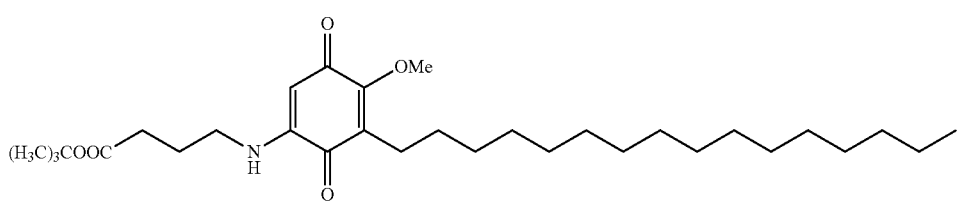
53
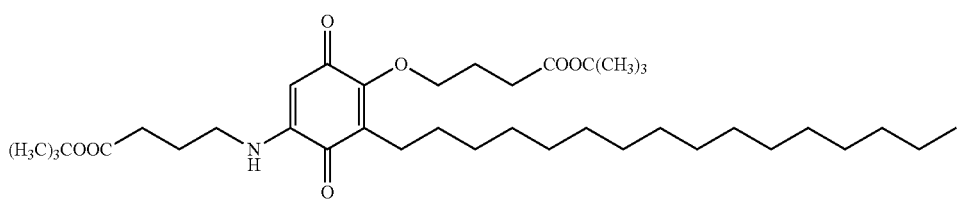
54

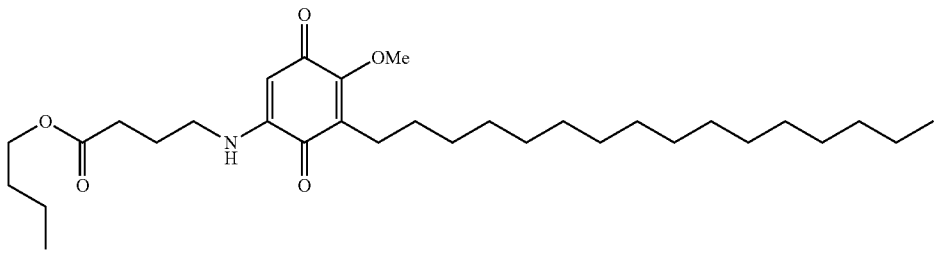
55
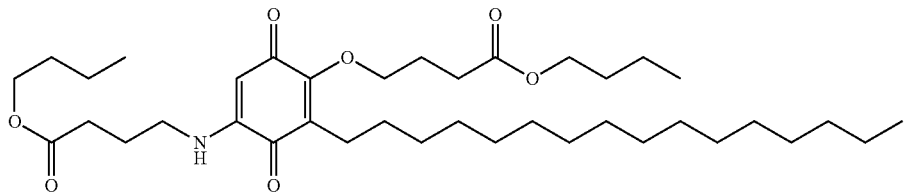
56
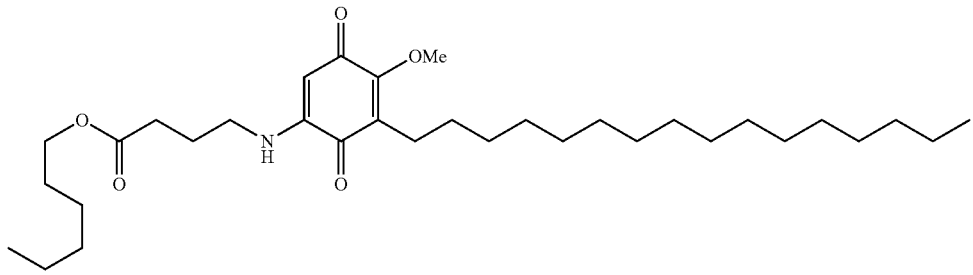
57
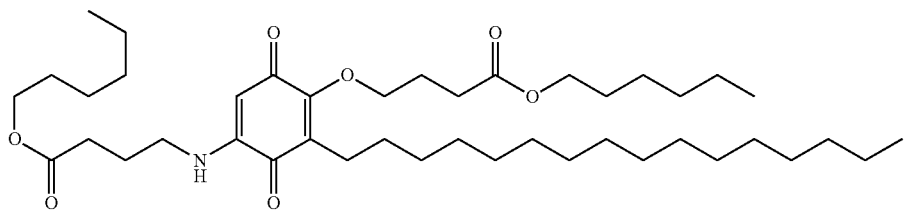
58
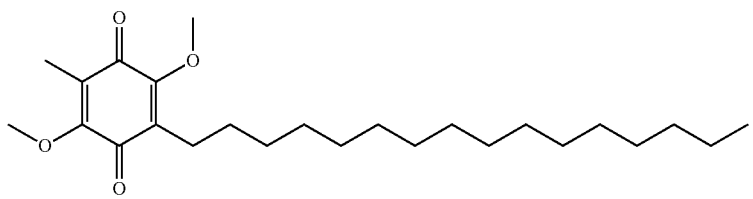
60
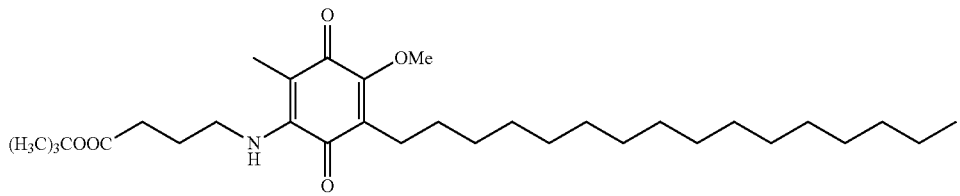
61
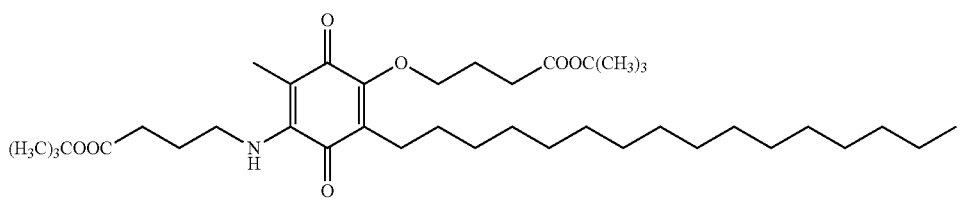
62

-continued

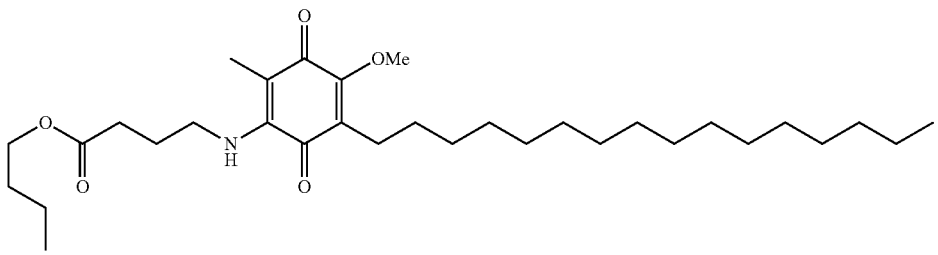
63

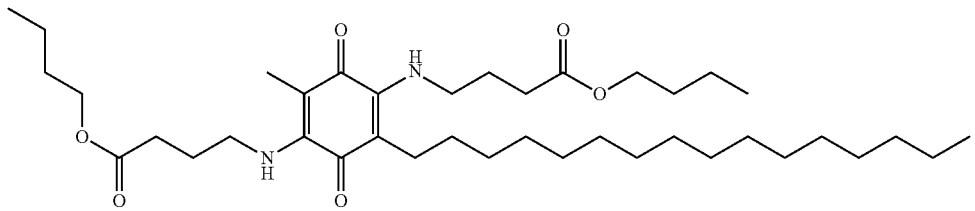
64

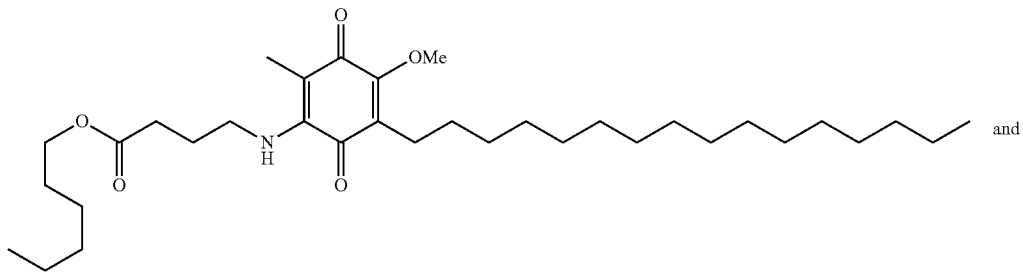
65 and

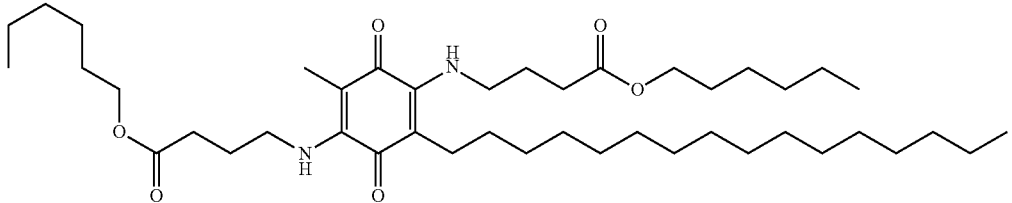
66 and salts thereof.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Therapeutic Applications

Compounds of the invention are useful, for example, for treating or suppressing diseases associated with impaired mitochondrial function resulting in diminished ATP production and/or oxidative stress and/or lipid peroxidation in a subject in need of treatment. The present disclosure provides methods of treating conditions including but not limited to Friedreich's ataxia, Leber's Hereditary Optic Neuropathy, Kearns-Sayre Syndrome, Mitochondrial Encephalomyopathy with Lactic Acidosis and Stroke-Like Episodes, and Leigh syndrome in an animal.

The compounds are also useful for treating conditions including but not limited to obesity, atherosclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, in an animal.

Friedreich's Ataxia

Friedreich's ataxia is a severe neurodegenerative and cardiodegenerative condition. It is characterized by progressive ataxia of the limbs, muscle weakness, dysarthria, skeletal deformities and cardiomyopathy. While the biochemical basis of the disease is still under investigation, it is strongly associated with insufficient frataxin (Wilson et al. (1997) *Nat. Genet.* 16, 352-357; Wilson et al. (2003) *J. Neurol. Sci.* 207, 103-105). In the majority of patients the insufficiency of frataxin is a consequence of an intronic GAA triplet repeat expansion in the gene for frataxin, which results in a significant decrease in its mRNA levels, and ultimately in protein levels as well (Campuzano et al. (1996) *Science* 271, 1423-1427; Campuzano et al. (1997) *Hum. Mol. Genet.* 6, 1771-1780). Frataxin acts as an iron chaperone during heme biosynthesis (Bencze et al. (2007) *J.C.S. Chem. Commun.* 1798-1800) and has been shown to be capable of stimulating the in vitro assembly of heme and Fe—S clusters (Park et al. (2003) *J. Biol. Chem.* 278, 31340-31351; Yoon et al. (2003) *J. Am Chem. Soc.* 125, 6078-6084; Yoon et al. (2004) *J. Biol. Chem.* 279, 25943-25946). Frataxin can interact physically with mitochondrial electron transport chain proteins, as well as with mitochondrial aconitase (which contains an Fe—S cluster) (Bulteau et al. (2004) *Science* 305, 242-245; Gonzalez-Cabo et al. (2005) *Hum. Mol. Genet.* 14, 2091-2098). Therefore, frataxin deficiency results in disruption of cellular iron homeostasis, with a progressive iron accumulation in the mitochondrion, and a deficiency in heme and Fe—S clusters.

It is believed that a deficiency in frataxin leads to compromised mitochondrial respiratory chain function through a failure to assemble one or more Fe-utilizing proteins; one or more Fe—S clusters in the mitochondrial respiratory complexes are likely to represent a critical locus. In fact, diminished function of these complexes has been noted in Friedreich's ataxia patients (Bradley et al. (2000) *Hum. Mol. Genet.* 9, 275-282). The loss of mitochondrial respiratory chain function can lead to diminished ATP production, while the accumulation of Fe in the mitochondria makes the organelle highly susceptible to oxidative damage by reactive oxygen species, whose concentration increases concomitant with the decrease in respiratory chain function. There is compelling evidence that while oxidative damage is not the primary lesion in Friedreich's ataxia, oxidative stress helps to drive disease progression. Therefore, strategies to overcome oxidative stress should blunt disease progression and provide effective therapy.

Other Exemplary Mitochondrial Diseases

Leber hereditary optic neuropathy is associated with degeneration of retinal ganglion cells and causes progressive loss of vision resulting in various degrees of blindness. Leber hereditary optic neuropathy primarily affects men over the age of 20 and is maternally transmitted due to mutations in the mitochondrial (not nuclear) genome.

Kearns-Sayre syndrome is a rare neuromuscular disorder typically with onset usually before the age of 20. It is characterized by progressive external ophthalmoplegia (paralysis of the eye muscles) and mild skeletal muscle weakness, hearing loss, loss of coordination, heart problems, and cognitive delays. There are many other names for the Kearns-Sayre syndrome including: Chronic progressive external ophthalmoplegia CPEO with myopathy; CPEO with ragged-red fibers; KSS; Mitochondrial cytopathy, Kearns-Sayre type; Oculocraniosomatic syndrome; Ophthalmoplegia-plus syndrome; Ophthalmoplegia with myopathy; and Ophthalmoplegia with ragged-red fibers.

Mitochondrial Encephalomyopathy with Lactic Acidosis and Stroke-Like Episodes is a progressive mitochondrial disease that involves multiple organ systems including the central nervous system, cardiac muscle, skeletal muscle, and gastrointestinal system. Symptoms include muscle weakness, stroke-like events, eye muscle paralysis, and cognitive impairment. Leigh syndrome is a degenerative brain disorder usually diagnosed at a young age (e.g. before age two). Deterioration is often rapid with symptoms such as seizures, dementia, feeding and speech difficulties, respiratory dysfunction, heart problems, and muscle weakness. Prognosis is poor with death typically occurring within a few years of diagnosis.

Mitochondrial Energy Production

Energy released from the citric acid (Krebs) cycle in the mitochondrial matrix enters the mitochondrial electron transport chain as NADH (complex I) and $FADH_2$ (complex II). These are the first two of five protein complexes involved in ATP production, all of which are located in the inner mitochondrial membrane. Electrons derived from NADH (by oxidation with a NADH-specific dehydrogenase) and $FADH_2$ (by oxidation with succinate dehydrogenase) travel down the respiratory chain, releasing their energy in discrete steps by driving the active transport of protons from the mitochondrial matrix to the intermembrane space (i.e., through the inner mitochondrial membrane). The electron carriers in the respiratory chain include flavins, protein-bound iron-sulfur centers, quinones, cytochromes and copper. There are two molecules that transfer electrons between complexes: coenzyme Q (complex I→III, and complex II→III) and cytochrome c (complex III→IV). The final electron acceptor in the respiratory chain is $O_2$, which is converted to $H_2O$ in complex IV. In a functional mitochondrion, transport of two electrons through complex I results in the transport of $4H^+$ into the intermembrane space. Two more F1' transfers to the intermembrane space result from electron transport through complex III, and four more $H^+$ transfers from electron transport through complex IV. The 10 electrons transported to the intermembrane space create a proton electrochemical gradient; they can return to the mitochondrial matrix via complex V (ATP synthase), with the concomitant conversion of ADP to ATP. It is interesting that no $H^+$ is transferred to the intermembrane space as a consequence of electron transport through complex II. Therefore, $2e^-$ transfer from FADH2 (complex II→complex III→complex IV) results in the transport of only 6 protons, compared with 10 protons resulting from $2e^-$ transfer from NADH (complex I→complex III→complex IV), with correspondingly less ATP produced. Each glucose molecule metabolized by glycolysis produces 12 electrons; these are converted to 5 NADH molecules and 1 $FADH_2$ via the Krebs cycle in the mitochondrial matrix. The 5 NADH molecules employed in mitochondrial electron transport produce about 25 ATPs, while the single $FADH_2$ affords only about 3 ATP molecules. (There are another 4 molecules of ATP derived from glucose metabolism—2 during glycolysis and 2 in the Krebs cycle). While this analysis underscores the importance of complex I involvement in normal ATP production, it also tends to obscure certain metabolic realities/uncertainties that may offer important opportunities for therapeutic intervention. One metabolic reality is that complex I, while important quantitatively for ATP production in normal mitochondria, is not essential for all mitochondrial ATP production. Electrons can enter the electron transport chain at the level of coenzyme Q (either from complex II or from fatty acid oxidation), producing about 60% as much ATP as would have resulted had they entered the electron transport chain at complex I). While the flux of electrons that normally enter the individual mitochondrial complexes, ultimately passing through coenzyme Q, is probably dictated largely by the availability of electrons derived from NADH, $FADH_2$ and fatty acid oxidation, the actual intrinsic capacity of the individual pathways does not appear to have been studied carefully.

In functional mitochondria, a few experimental parameters can be measured readily, reflecting mitochondrial respiration. These include NADH and $O_2$ consumption, and ATP production. Less readily measured are the electrons that flow through the electron transport chain, thereby consuming oxygen, and producing H2O and ATP. The electrons within the mitochondria can really only be measured when they are associated with one of the mitochondrial electron carriers such as coenzyme Q. In humans, this mitochondrial coenzyme is present as coenzyme $Q_{10}$, which has a 50-carbon C-substituent that renders the molecule virtually insoluble in water (calculated octanol-water partition coefficient)>$10^{20}$ (James et al. (2005) *J Biol. Chem.* 280, 21295-21312).

In dysfunctional mitochondria, one can still carry out the same types of measurements as noted above for functioning mitochondria. If the flow of electrons through complex I is interrupted, several measured parameters should change. These include diminished consumption of NADH (measured as increased lactate through pyruvate reduction) and diminished ATP production. Since electrons will not flow as efficiently from complex I to coenzyme Q, the concentration of this reduced coenzyme will diminish. Interestingly, a new pathway for oxygen consumption is created. While oxygen is not converted as efficiently to water in complex IV (an overall four electron reduction of each oxygen molecule), much of the flow of electrons into a defective complex I is redirected to oxygen, with the production of superoxide (a one electron reduction of each oxygen). Thus, the stoichiometry of oxygen utilization is altered. The production of superoxide by mitochondria actually occurs to some extent even in normal mitochondria, but is a much more frequent event in mitochondria containing defects in the respiratory chain. Superoxide is one form of reactive oxygen species (ROS). Superoxide itself is not believed to react readily with biological molecules such lipid membranes, proteins and DNA, and actually functions as a signaling molecule for the regulation of certain cellular processes. Biologically, the main fate of superoxide ($O_2$) is a disproportionation reaction with itself to produce peroxide ($H_2O_2$) and oxygen, i.e.

$$2O_2 + 2H^+ \rightarrow H_2O_2 + O_2$$

This reaction occurs spontaneously, and can also be catalyzed by superoxide dismutase. Superoxide can also be reduced to peroxide in a monovalent process. Like superoxide, hydrogen peroxide is also not intrinsically deleterious to cellular macromolecules, and is actually essential to the function of a number of enzymes. However, in the presence of metal ions such as iron and copper, hydrogen peroxide is converted to hydroxyl radical (HO.) and hydroxide ion (OH$^-$) according to the Fenton reaction, i.e.

$$HOOH + Fe^{2+} \rightarrow Fe^{3+} + HO. + OH^-$$

Hydroxyl radicals are very highly reactive, capable of reacting with virtually any biological molecule, including DNA, proteins and lipids. Hydroxyl radicals can also diffuse through cells readily, and their ability to damage cells is limited only by the distance that they travel before they react. Hydroxyl radicals can also react with superoxide, producing singlet oxygen ($^1O_2$)+OH$^-$), another highly reactive form of ROS that damages cellular macromolecules and assemblies. One particularly deleterious and well studied reaction mediated by hydroxyl radicals is the abstraction of hydrogen atoms (H.) from membrane lipids, forming a carbon-centered radical (R.). This radical $$HO. + RH \text{ (lipid)} \rightarrow R. + H_2O$$

$$R. + O_2 \rightarrow ROO.$$

$$ROO. + RH \rightarrow ROOH + R.$$

can readily react with oxygen, forming a hydroperoxy radical (ROO.). The hydroperoxy radical is also highly reactive, and can abstract another hydrogen atom from the membrane lipid, producing another carbon-centered radical (which can undergo precisely the same chemistry), ultimately producing a chain reaction affording many oxidative lesions in the membrane lipids from a single hydroxyl radical (lipid peroxidation). It is for this reason that lipid peroxidation likely represents a major process by which cellular and mitochondrial membranes are degraded in cells containing (partially) dysfunctional mitochondria. The observed accumulation of lipofuscin in Friedreich's ataxia patients is fully consistent with the thesis that lipid peroxidation is a central process that drives disease progression (La Marche et al. (1980) *Can. J. Neurosci.* 7, 389-396; Yin, D. (1996) *Free Rad. Biol. Med.* 21, 871-888; Yamada et al. (2001) *J. Lipid Res.* 42, 1187-1196). It may be noted that while all lesions in the mitochondrial electron transport chain that affect mitochondrial dysfunction will result in elevated levels of superoxide, some types of lesions may be expected to produce more functional damage. The latter would certainly include Friedreich's ataxia, in which suboptimal levels of the protein frataxin (which is responsible for cellular iron homeostasis; Park et al. (2003) *J. Biol. Chem.* 278, 31340-31351; Yoon et al. (2003) *J. Am. Chem. Soc.* 125, 6078-6084; Yoon et al. (2004) *J. Biol. Chem.* 279, 25943-25946; Bencze et al. (2007) *J.C.S. Chem. Commun.* 1798-1800) results in an accumulation of $Fe^{2+}/Fe^{3+}$ within the mitochondria, and contributes instead to the Fenton chemistry noted above. Likewise, disorders such as amyotrophic lateral sclerosis are associated with a deficiency in the detoxifying enzyme superoxide dismutase, and will have greatly enhanced concentrations of the ROS discussed above.

One poorly studied parameter of mitochondrial electron transport is whether the process is best characterized as involving one or two electron transfers. This is important because NADH is an obligatory two-electron donor, and coenzyme Q and cytochrome c participate in two-electron redox cycles, as does $FADH_2$. Virtually all publications represent the processes in which these species participate as involving a net two electron change. However, $FADH_2$ may (and generally does) transfer its reducing equivalents as single electrons. Further, the Q cycle in complex III clearly involves single-electron transfers. Reduced cytochrome c is known to transfer electrons one at a time to cytochrome c oxidase, the enzyme responsible for the final step in respiration. Finally, the accumulation of electrons within dysfunctional mitochondria (producing reductive stress) is relieved substantially by (one-electron) reduction of oxygen to superoxide (vide supra). Thus, while the electron transport chain has the capacity to transfer two electrons by virtue of the redox cycles to most of its participants, it is not clear that it necessarily must do so to function.

Given that the reductive stress (build-up of electrons) encountered initially in mitochondrial dysfunction is a one electron process, as is lipid peroxidation, carriers of single electrons could find utility in dealing with reductive stress, e.g. molecules in which the one-electron reduced intermediate is stabilized by dipole interactions, substituent effects, resonance effects or captodative effects. Molecules designed to traffic single electrons, and which can (i) accept electrons from superoxide (ii) donate electrons to complex III and (iii) quench carbon-centered lipid radicals are especially useful. Multifunctional Radical Quenchers (MRQs) of the invention can effectively protect mitochondria, cells and organisms from oxidative stress.

The compounds and methods of the disclosure are illustrated further by the following examples, which are provided for illustrative purposes and not intended to be construed as limiting the disclosure in scope or spirit to the specific compounds and methods described in them.

EXAMPLES

All chemicals were purchased from Sigma Aldrich and Chem-Impex international. The chemicals used were all ACS reagent grade and were used without further purification, except for 1-bromotridecane which was purified by silica gel flash column chromatography prior to use. The reactions were carried out under an atmosphere of argon unless specified otherwise. Flash column chromatography was carried out using silica gel (Silicycle R10030B, 60 particle size, 230-400 mesh), applying a low pressure stream of nitrogen. Analytical thin layer chromatographic separations were carried out on glass plates coated with silica gel (60 particle size F254, SiliCycle TLG-R10011B-323). The TLC chromatograms were developed by immersing the plates in 2.5% potassium permanganate in ethanol or 2% anisaldehyde+5% sulfuric acid+1.5% glacial acetic acid in ethanol, followed by heating or visualized by UV radiation (254 nm). Melting points were recorded on a MelTemp apparatus and are uncorrected. Tetrahydrofuran was distilled from sodium/benzophenone ketyl and dichloromethane from calcium hydride. $^1$H and $^{13}$C NMR spectra were recorded on a Gemini 300 or Varian Inova 400, or on a Varian Inova 500 spectrometer, using CDCl$_3$ as solvent and internal standard, unless otherwise indicated. $^1$H NMR chemical shifts were reported relative to residual CDCl$_3$ at 7.26 ppm, or to residual DMSO-d$_6$ at 2.50 ppm, or to residual CD$_3$OD-d$_4$ at 3.31 ppm; $^{13}$C NMR shifts were reported relative to the central line of CDCl$_3$ at 77.16 ppm, or to residual DMSO-d$_6$ at 39.51 ppm, or to residual CD$_3$OD-d$_4$ at 49.0 ppm. Splitting patterns are designated as s, singlet; d, doublet; dd, double doublet; m, multiplet; q, quartet; quin, quintet. High-resolution mass spectra were obtained at the Michigan State Mass Spectrometry Facility or the Arizona State University CLAS High Resolution Mass Spectrometry Facility.

Example 1: Preparation of 2-hydroxy-5-methoxy-3-tridecylcyclohexa-2,5-diene-1,4-dione (5)

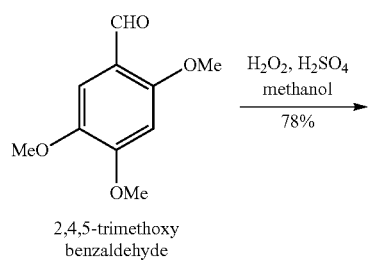

2,4,5-trimethoxy benzaldehyde

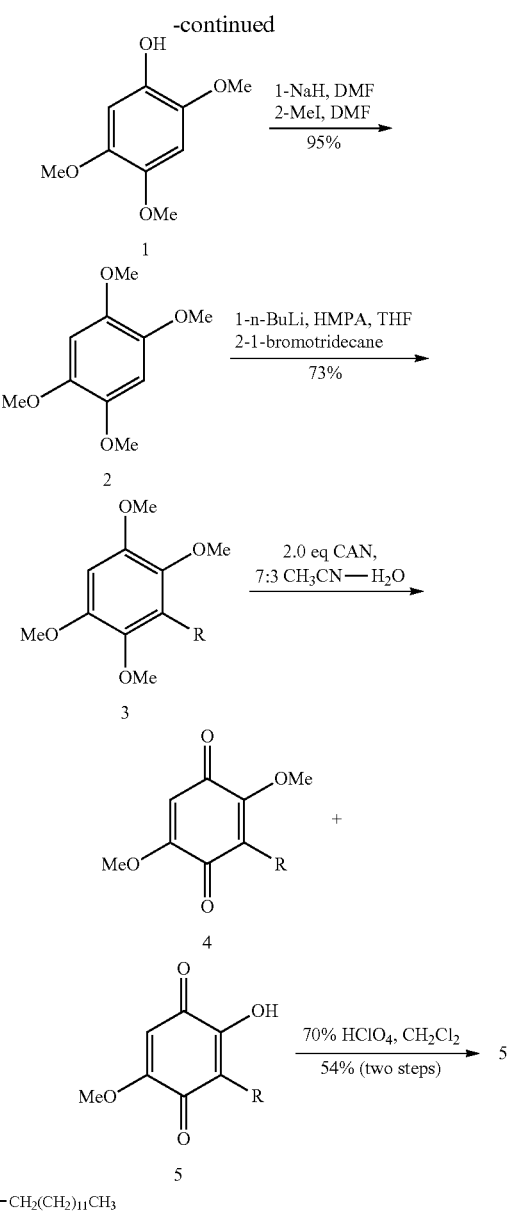

a. 2,4,5-trimethoxyphenol (1):

To a solution containing 10 g (51.0 mmol) of 2,4,5-trimethoxybenzaldehyde and 6.4 mL of H$_2$O$_2$ (35% wt solution in H$_2$O) in 102 mL of methanol was added 1.02 mL (18.4 mmol) of concentrated H$_2$SO$_4$ dropwise under an atmosphere of argon at room temperature. The reaction mixture was heated to reflux for 2 h, diluted with water and extracted with three 100 mL portions of dichloromethane. The combined organic layer was washed with brine, dried (MgSO$_4$) and concentrated under diminished pressure. The crude residue was applied to a silica gel column (12×4 cm). Step gradient elution with 1:4-1:2 ethyl acetate-hexanes afforded 1 as a yellow solid: yield 7.34 g (78%); silica gel TLC R_f 0.45 (1:1 ethyl acetate-hexanes); $^1$H NMR (CDCl$_3$) δ 3.48 (s, 6H), 3.52 (s, 3H), 6.08 (br.s, 1H), 6.33 (s, 1H), 6.36 (s, 1H); $^{13}$C NMR (CDCl$_3$) δ 56.4, 57.0, 57.2, 99.6, 100.9, 139.6, 142.1 and 143.8.

b. 1,2,4,5-tetramethoxybenzene (2)

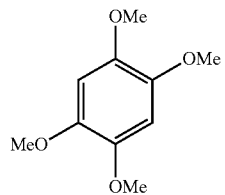 [SMILES: COc1cc(OC)c(OC)cc1OC]

To a solution of sodium hydride (1.38 g, 57.5 mmol) washed with several portions of hexane (60% oil dispersion) in dry N,N-dimethylformamide was added a solution of 7.06 g (38.3 mmol) of alcohol 1 in 62 mL of dry N,N-dimethylformamide. The mixture was stirred at 0° C. for 30 min under an argon atmosphere and 4.78 mL (76.6 mmol) of methyl iodide was added dropwise. The reaction mixture was then stirred at room temperature for 13 h and quenched upon addition of 10 mL of CH$_3$OH. The solvent was evaporated under diminished pressure to afford a crude residue. The crude residue was extracted with five 10 mL portions of dichloromethane, was washed successively with 50 mL of 3% aqueous HCl, distilled water, brine and dried (MgSO$_4$). The solvent was evaporated under diminished pressure to afford a crude residue. The crude residue was applied to a silica gel column (8×4 cm). Elution with 1:4 ethyl acetate-hexanes gave 2 as a white solid: yield 7.21 g (95%); silica gel TLC R_f 0.32 (1:2 ethyl acetate-hexanes); $^1$H NMR (CDCl$_3$) δ 3.70 (s, 12H), 6.47 (s, 2H); $^{13}$C NMR (CDCl$_3$) δ 57.1, 100.7 and 143.2.

c. 1,2,4,5-tetramethoxy-3-tridecylbenzene (3)

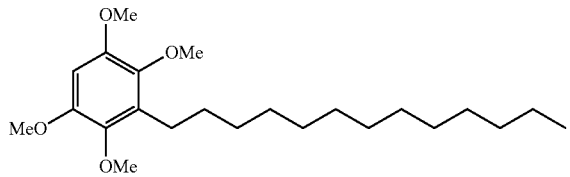 [SMILES: CCCCCCCCCCCCCc1c(OC)c(OC)cc(OC)c1OC]

To a solution containing 1.0 g (5.0 mmol) of 1,2,4,5-tetramethoxybenzene (2) and 87 µL (90 mg, 0.50 mmol) hexamethyl phosphoramide in 25 mL dry THF was added 3.4 mL (1.6 M in Hexanes, 5.5 mmol) of n-butyllithium dropwise at −40° C. over 5 min. The reaction mixture is warmed to 0° C. over 2 h, 1.4 mL (1.4 g, 5.5 mmol), of purified 1-bromotridecane added and the reaction mixture stirred at room temperature under an atmosphere of argon for 15 h. The reaction mixture was quenched with 20 mL of saturated NH$_4$Cl and extracted with five 10 mL portions of diethyl ether. The organic layer was washed with distilled water, brine and dried (MgSO$_4$). The excess solvent was concentrated under diminished pressure to afford a crude residue. The crude residue was applied to a silica gel column (6×3 cm). Elution with 1:9 ethyl acetate-hexanes afforded 3 as a colorless solid: yield 1.4 g (73%); mp 31-32° C.; 0.20 g (20%) of unreacted 1,2,4,5-tetramethoxybenzene (2) was recovered; silica gel TLC R_f 0.45 (1:1 ethyl ether-hexanes); $^1$H NMR (CDCl$_3$) δ 0.87 (3H, t, J=6.8 Hz), 1.14-1.46 (20H, m), 1.47-1.58 (2H, m), 2.61 (2H, dd, J=8.8 and 6.9 Hz), 3.76 (6H, s), 3.82 (6H, s), 6.40 (1H, s); $^{13}$C NMR (CDCl$_3$) δ 14.1, 22.7, 24.7, 29.4, 29.5, 29.6, 29.70, 29.75, 29.76, 30.0, 30.8, 32.0, 56.2, 60.4, 60.9, 96.7, 131.1, 141.1 and 148.8.

d. 2-hydroxy-5-methoxy-3-tridecylcyclohexa-2,5-diene-1,4-dione (5)

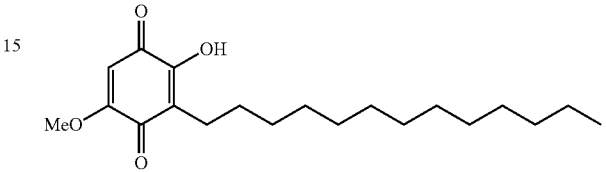

To a solution containing 0.10 g (0.26 mmol) of 1-(2,3,5,6-tetramethoxyphenyl)-tridecane (3) in 2.6 mL of acetonitrile was added 2.6 mL (0.28 g, 0.52 mmol) of 7:3 solution of cerium (IV) ammonium nitrate in acetonitrile (1.82 mL):water (0.78 mL) drop wise at −7° C. (salt-ice bath) over 30 min. The reaction was allowed to stir at room temperature for 3 h and diluted with 10 mL of diethylether. The organic layer was washed with distilled water, brine and dried (MgSO$_4$). The excess solvent was concentrated under reduced pressure to afford a crude mixture of quinones 4 and 5. To a solution of the crude mixture obtained above in 2.6 mL of dichloromethane was added 1.1 mL (13 mmol) of 70% perchloric acid dropwise at 0° C. The reaction mixture was stirred at 0° C. for 9 h, diluted with 10 mL of dichloromethane, washed with distilled water, brine and dried (MgSO$_4$). The excess solvent was concentrated under diminished pressure to afford a crude residue. The crude residue was applied to a silica gel column (7×2 cm). Elution with 1:4 ethyl acetate-hexanes gave 5 as a yellow-orange solid: yield 48 mg (54%); mp 90-92° C.; silica gel TLC R_f 0.58 (1:1 ethyl acetate-hexanes); $^1$H NMR (CDCl$_3$) δ 0.85 (3H, t, J=6.8 Hz), 1.17-1.33 (20H, m), 1.39-1.49 (2H, m), 2.41 (2H, t, J=8 Hz), 3.84 (3H, s), 5.82 (1H, s), 7.32 (1H, s); $^{13}$C NMR (CDCl$_3$) δ 14.2, 22.7, 22.8, 28.1, 29.48, 29.54, 29.68, 29.69, 29.77, 29.78, 29.79, 29.80, 32.0, 56.9, 102.3, 119.4, 151.7, 161.2, 181.8 and 183.0.

Example 2: Preparation of tert-butyl 4-(4-hydroxy-3,6-dioxo-5-tridecylcyclohexa-1,4-dienylamino)butanoate (6)

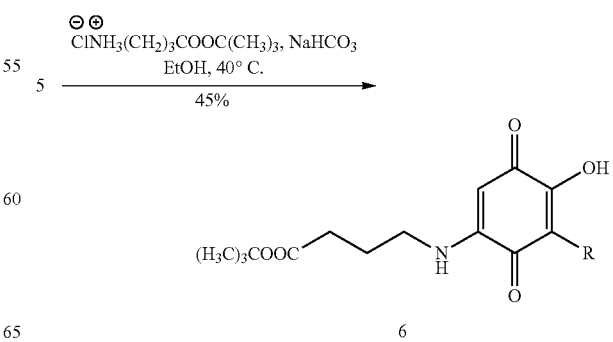

To a solution of 42 mg (0.13 mmol) of 2-hydroxy-5-methoxy-3-tridecyl-(1,4)-benzoquinone (5) and 1.0 g (13 mmol) of sodium bicarbonate in 9.7 mL of ethanol was added 39 mg (0.19 mmol) of γ-aminobutyric acid tert-butyl ester hydrochloride salt. The reaction mixture was stirred for 27 h at 45° C. under an atmosphere of argon. The reaction mixture was then diluted with 5 mL of water and extracted with seven 2 mL portions of dichloromethane. The organic layer was washed with water, brine and dried ($Na_2SO_4$). The excess solvent was concentrated under diminished pressure to afford a crude residue. The crude residue was applied to a silica gel column (5×2 cm). Elution with dichloromethane gave 6 as a dark red solid: yield 27 mg (45%); mp 96-97° C.; silica gel TLC $R_f$ 0.38 (dichloromethane); $^1$H NMR ($CDCl_3$) δ 0.86 (314, t, J=6.5 Hz), 1.20-1.32 (20H, m), 1.38-1.46 (11H, m), 1.94 (2H, quin, J=6.9 Hz), 2.31 (2H, t, J=7.0 Hz), 2.34-2.40 (2H, m), 3.21 (2H, dd, J=12.9 and 6.6 Hz), 5.35 (1H, s), 6.58 (1H, s); $^{13}$C NMR ($CDCl_3$) δ 14.3, 22.79, 22.84, 23.5, 28.23, 28.24, 29.5, 29.6, 29.73, 29.75, 29.81, 29.83, 29.84, 32.1, 32.8, 42.4, 81.2, 91.9, 115.9, 149.9, 155.1, 172.1, 179.0 and 182.6; mass spectrum (LCT electrospray), m/z 486.3181 (M+Na)$^+$ ($C_{27}H_{45}NO_5Na$ requires m/z 486.3195).

Example 3: Preparation of tert-butyl 4-(4-methoxy-3,6-dioxo-5-tridecylcyclohexa-1,4-dienylamino) butanoate (7)

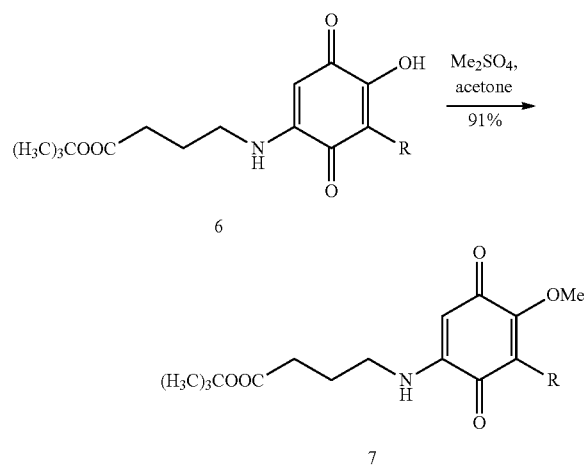

To a solution containing 22 mg (0.047 mmol) of 6 and 0.25 g (1.8 mmol) of potassium carbonate in 1.2 mL of dry acetone was added 23 μL (0.23 mmol) of dimethyl sulfate. The reaction mixture was heated to reflux overnight, cooled to room temperature and concentrated under diminished pressure. The crude mixture was redissolved in 10 mL of dichloromethane, washed with 5 mL of 1N HCl and the aq layer extracted with three 10 mL portions of dichloromethane. The combined organic layer was dried ($MgSO_4$) and concentrated under diminished pressure. The residue was purified by flash column chromatography on a silica gel column (24×2 cm). Elution with 1:5 ethyl acetate-hexane gave 7 as a bright red amorphous solid: yield 21 mg (91%); silica gel TLC $R_f$ 0.60 (1:2 ethyl acetate-hexanes); $^1$H NMR ($CDCl_3$) δ 0.87 (3H, t, J=6.8 Hz), 1.16-1.42 (22H, m), 1.45 (9H, s), 1.82-2.03 (2H, quin, J=9 Hz), 2.31 (2H, t, J=7.2 Hz), 2.35-2.39 (2H, m), 3.14 (2H, dd, J=13.0 and 6.8 Hz), 4.10 (3H, s), 5.28 (1H, s), 5.94 (1H, t, J=5.6 Hz); $^{13}$C NMR ($CDCl_3$) δ 14.3, 22.8, 23.1, 23.6, 28.20, 28.24, 28.8, 29.5, 29.6, 29.7, 29.81, 29.83, 32.1, 32.9, 42.1, 61.8, 81.1, 96.1, 127.6, 146.9, 158.5, 172.18, 172.20, 181.8 and 183.9; mass spectrum (APCI), m/z 478.3532 (M+H)$^+$ ($C_{28}H_{48}NO_5$ requires m/z 478.3532).

Example 4: Preparation of 4-(4-hydroxy-3,6-dioxo-5-tridecylcyclohexa-1,4-dienylamino)butanoic Acid (8)

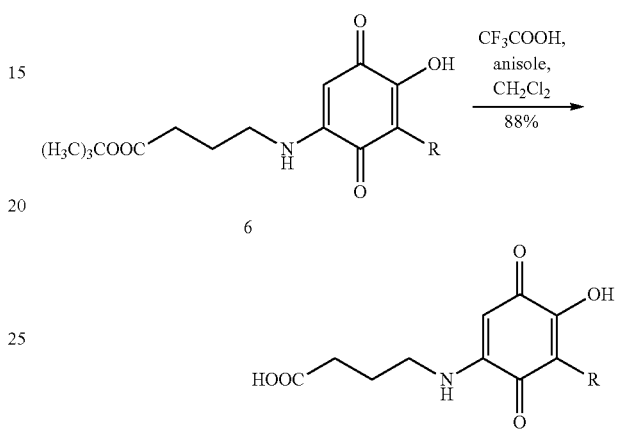

To a solution containing 28 mg (0.060 mmol) of 6 in 0.37 mL of dichloromethane was added 6.5 μL (0.060 mmol) of anisole[13] and 0.40 mL (5.4 mmol) of trifluoroacetic acid. The reaction mixture was stirred for 24 h at room temperature under an atmosphere of argon. The reaction mixture was concentrated under diminished pressure and the excess trifluoroacetic acid removed by co-evaporation with cyclohexane thrice to afford a crude residue. The crude residue is reprecipitated from methanol to give 8 as red amorphous solid: yield 21 mg (88%); mp 194-195° C.; $^1$H NMR (DMSO-$d_6$) δ 0.85 (3H, t, J=6.8 Hz), 1.15-1.42 (22H, m), 1.74 (2H, quin, J=14.4 and 7.2 Hz), 2.26 (4H, q, J=6.9 Hz), 3.14 (2H, dd, J=13.8 and 6.7 Hz), 5.32 (1H, s), 7.78 (1H, t, J=6.2 Hz), 10.49 (1H, br s), 12.2 (1H, br s); $^{13}$C NMR (DMSO-$d_6$) δ14.0, 22.1, 22.2, 22.8, 27.6, 28.8, 28.9, 29.0, 29.02, 29.06, 29.08, 29.10, 30.9, 31.3, 41.4, 91.8, 115.6, 149.3, 156.7, 174.2, 178.5 and 182.5; mass spectrum (LCT electrospray), m/z 430.2564 (M+Na)$^+$ ($C_{23}H_{37}NO_5Na$ requires m/z 430.2569).

Example 5: Preparation of 4-(4-methoxy-3,6-dioxo-5-tridecylcyclohexa-1,4-dienylamino)butanoic Acid (9)

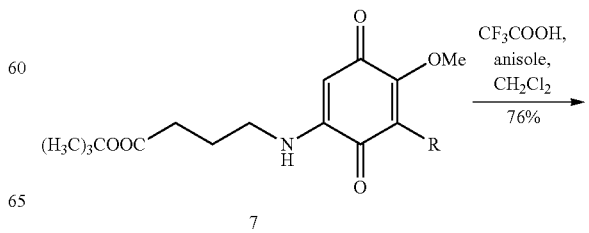

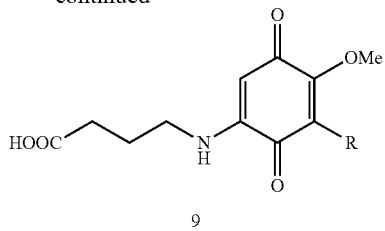

To a solution containing 9.0 mg (0.019 mmol) of 7 in 0.12 mL of dichloromethane was added 2.0 μL (0.019 mmol) of anisole, 0.13 mL (1.7 mmol) of trifluoroacetic acid and the reaction mixture was stirred for 24 h at room temperature under an atmosphere of argon. The reaction mixture was successively coevaporated with six 5 mL portions of cyclohexane and the excess solvent concentrated under diminished pressure to afford a crude residue. The crude residue was purified by flash column chromatography on a silica gel column (22×2 cm). Elution with 100:1 chloroform-methanol gave 9 as red amorphous solid: yield 6.0 mg (76%); silica gel TLC $R_f$ 0.32 (1:1 ethyl acetate-hexanes); $^1$H NMR (CDCl$_3$) δ 0.88 (3H, t, J=6.9 Hz), 1.22-1.41 (22H, m), 1.98 (2H, quin, J=6.9 Hz), 2.33-2.40 (2H, m), 2.47 (2H, t, J=6.9 Hz), 3.20 (2H, q, J=6.6 Hz), 4.11 (3H, s), 5.29 (1H, s), 5.97 (1H, s); $^{13}$C NMR (CDCl$_3$) δ 14.3, 18.5, 22.8, 23.1, 23.2, 28.8, 29.5, 29.6, 29.7, 29.81, 29.84, 31.3, 32.1, 42.0, 51.0, 58.6, 61.8, 96.2, 127.7, 146.9, 158.5, 176.6, 181.8 and 184.0; mass spectrum (APCI), m/z 422.2898 (M+H)$^+$ (C$_{24}$H$_{40}$NO$_5$ requires 422.2906).

Example 6: Preparation of benzyl 4-(4-hydroxy-3,6-dioxo-5-tridecylcyclohexa-1,4-dienylamino)butanoate (11)

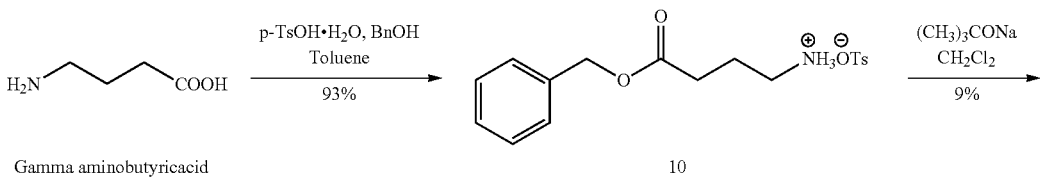

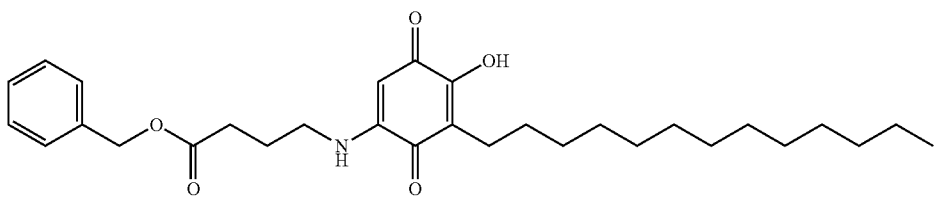

a. Tosylate Salt (10)

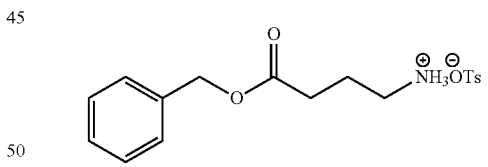

A solution of 1.00 g (9.70 mmol) of 4-aminobutanoic acid, 2.02 g (1.08 mmol) of p-toluenesulfonic acid monohydrate and 1.24 mL (1.29 g, 1.24 mmol) of benzyl alcohol in 20 mL of toluene was heated to reflux, using a Dean-Stark distilling receiver, for 24 h. The reaction mixture was cooled to room temperature and diluted with 20 mL of anhydrous diethyl ether to afford p-toluenesulfonate 10 as a crystalline, colorless solid: yield 3.30 g (93%); silica gel TLC $R_f$ 0.47 (9:1 chloroform-methanol); $^1$H NMR (CDCl$_3$) δ 1.89 (quin, 2H, J=7.3 Hz), 2.28-2.40 (m, 5H), 2.87 (dt, 2H, J=12.8 and 6.3 Hz), 5.04 (s, 2H), 7.11 (d, 2H, J=7.9 Hz), 7.27-7.37 (m, 5H) and 7.76-7.85 (m, 5H); $^{13}$C NMR (CDCl$_3$) δ 21.4, 22.6, 30.9, 39.3, 66.5, 126, 128.30, 128.35, 128.6, 129.2, 135.9, 140.9, 141.2 and 172.3.

b. Benzyl 4-(4-hydroxy-3,6-dioxo-5-tridecylcyclohexa-1,4-dienylamino)butanoate (11)

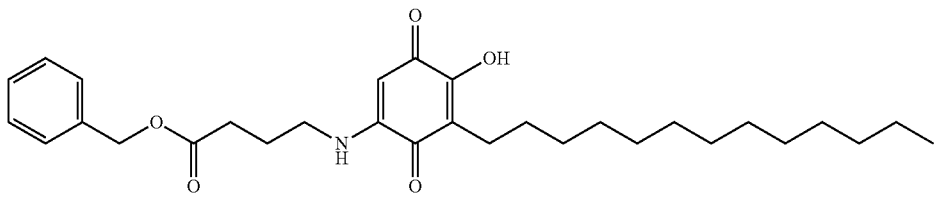

11

To a solution containing 57.0 mg (0.17 mmol) of 2-hydroxy-5-methoxy-3-tridecyl-(1,4)-benzoquinone (5) in 8 mL of dichloromethane was added a solution containing 185 mg (0.51 mmol) of p-toluenesulfonate salt 10 and 60.0 mg (97%, 0.51 mmol) of potassium tert-butoxide in 8 mL of dichloromethane dropwise over a period of 10 min. The reaction mixture was stirred at room temperature for 20 h under an argon atmosphere, then washed with 5 mL of 1 N HCl. The aqueous layer was extracted with seven 2-mL portions of dichloromethane. The combined organic layer was washed successively with water and brine and then dried (MgSO$_4$). The solvent was concentrated under diminished pressure to afford a crude residue. The residue was applied to a silica gel column (24×3 cm). Elution with diethyl ether gave compound 11 as a dark red solid: yield 11.0 mg (9%); silica gel TLC R$_f$ 0.25 (1:1 ethyl acetate-hexanes); $^1$H NMR (CDCl$_3$) δ 0.90 (t, 3H, J=6.8 Hz), 1.21-1.36 (m, 20H), 1.38-1.52 (m, 2H), 1.96-2.09 (m, 2H), 2.31-2.45 (m, 3H), 2.44-2.61 (m, 2H), 3.15-3.34 (m, 2H), 5.15 (s, 2H), 5.37 (s, 1H), 6.56 (s, 1H) and 7.13-7.46 (m, 5H); $^{13}$C NMR (CDCl$_3$) δ 14.3, 21.6, 22.8, 23.4, 28.2, 29.5, 29.6, 29.7, 29.80, 29.83, 31.6, 32.1, 42.2, 66.8, 92.0, 125.4, 128.3, 128.5, 128.6, 128.8, 129.2, 135.68, 135.72, 138.00, 138.02, 149.8, 155.1, 172.6, 179 and 182.5; mass spectrum (APCI), m/z 498.3206 (M+H)$^+$ (C$_{30}$H$_{44}$NO$_5$ requires 498.3219).

Example 7: Preparation of benzyl 4-(4-methoxy-3,6-dioxo-5-tridecylcyclohexa-1,4-dienylamino)butanoate (12)

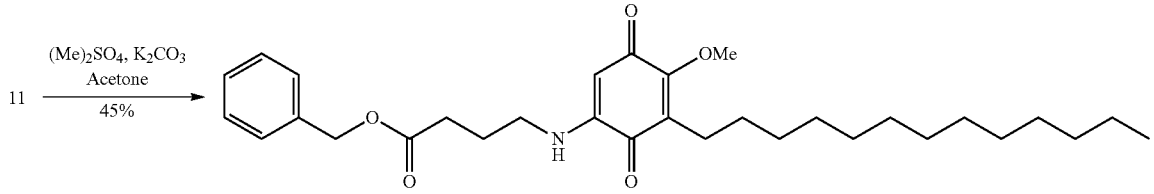

12

To a solution containing 12.0 mg (24.0 μmol of quinone 11 and 125 mg (0.91 mmol) of potassium carbonate in 0.6 mL of anh acetone was added 45.0 μL (60.0 mg, 0.48 mmol) of dimethyl sulfate. The reaction mixture was heated to reflux overnight, then allowed to cool to room temperature and concentrated under diminished pressure. The crude mixture was redissolved in 10 mL of dichloromethane and washed with 5 mL of 1 N HCl. The aqueous layer was extracted with three 10-mL portions of dichloromethane. The combined organic layer was dried (MgSO$_4$) and concentrated under diminished pressure to afford a crude residue. The residue was applied to a silica gel column (23×2 cm). Elution with 20% diethyl ether in hexane gave compound 12 as a bright red solid: yield 8 mg (45%); silica gel TLC R$_f$ 0.40 (1:1 ethyl acetate-hexanes); $^1$H NMR (CDCl$_3$) δ 0.81-0.97 (m, 3H), 1.15-1.34 (m, 20H), 1.32-1.45 (m, 2H), 1.98 (quin, 2H, J=7.0 Hz), 2.29-2.41 (m, 2H), 2.45 (t, 2H, J=7.1 Hz), 3.15 (q, 2H, J=6.7 Hz), 4.11 (s, 3H), 5.14 (s, 2H), 5.25 (s, 1H), 5.92 (t, 1H, J=5.5 Hz) and 7.19-7.44 (m, 5H); $^{13}$C NMR (CDCl$_3$) δ 14.3, 22.8, 23.1, 23.5, 28.8, 29.5, 29.6, 29.7, 29.81, 29.84, 31.7, 32.1, 42.0, 61.8, 66.8, 96.2, 127.7, 128.50, 128.55, 128.8, 135.8, 146.8, 158.5, 172.7, 181.8 and 183.9; mass spectrum (APCI), m/z 512.3379 (M+H)$^+$ (C$_{31}$H$_{46}$NO$_5$ requires 512.3376).

Example 8: Preparation of Butyl 4-(4-hydroxy-3,6-dioxo-5-tridecylcyclohexa-1,4-dienylamino)butanoate (14)

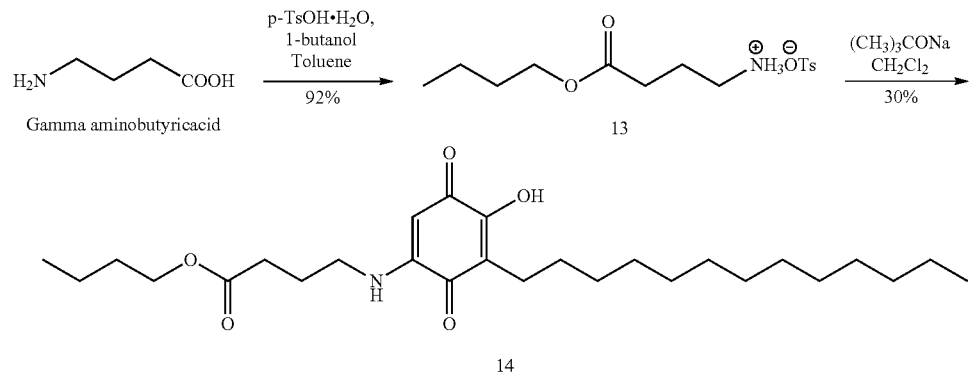

a. Tosylate Salt (13)

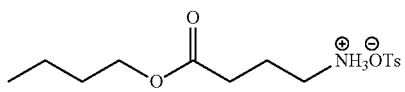

A solution of 1.00 g (9.70 mmol) of 4-aminobutanoic acid, 2.02 g (1.08 mmol) of p-toluenesulfonic acid monohydrate and 1.10 mL (891 mg, 1.24 mmol) of 1-butanol in 20 mL of toluene was heated to reflux, using a Dean-Stark distilling receiver, for 24 h. The reaction mixture was allowed to cool to room temperature and diluted with 20 mL of anh diethyl ether to afford the p-toluenesulfonate salt 13 as a crystalline, colorless solid: yield 2.96 g (92%); silica gel TLC $R_f$ 0.25 (9:1 chloroform-methanol); $^1$H NMR (CD$_3$OD) δ 0.94 (t, 3H, J=7.40 Hz), 1.33-1.46 (m, 2H), 1.55-1.67 (m, 2H), 1.92 (dt, 2H, J=20.0 and 7.30 Hz), 2.37 (s, 3H), 2.44 (t, 2H, J=7.20 Hz), 2.92-3.02 (m, 2H), 4.09 (t, 2H, J=6.60 Hz), 4.86 (s, 3H), 7.24 (d, 2H, J=10.5 Hz) and 7.71 (d, 2H, J=10.0 Hz); $^{13}$C NMR (CD$_3$OD) δ 14.0, 20.1, 21.4, 23.7, 31.6, 31.8, 40.1, 65.6, 126.8, 129.5, 141.6, 143.3 and 174.1.

b. Butyl 4-(4-hydroxy-3,6-dioxo-5-tridecylcyclohexa-1,4-dienylamino)butanoate (14)

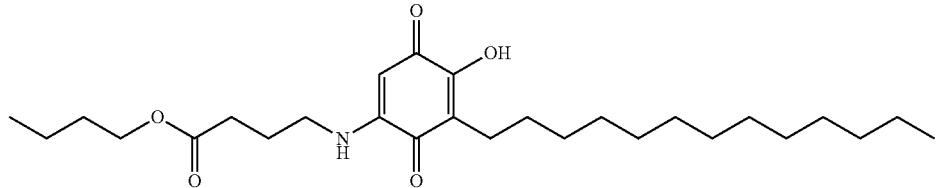 [SMILES: CCCCCCCCCCCCCC1=C(O)C(=O)C=C(NCCCC(=O)OCCCC)C1=O]

To a solution containing 82.0 mg (0.24 mmol) of 2-hydroxy-5-methoxy-3-tridecyl-(1,4)-benzoquinone (5) in 11.5 mL of dichloromethane was added a solution containing 241 mg (0.73 mmol) of p-toluenesulfonate salt 13 and 72.0 mg (97%, 0.73 mmol) of potassium tert-butoxide in 11.5 mL of dichloromethane dropwise over a period of 10 min. The reaction mixture was stirred at room temperature for 20 h under an argon atmosphere. The reaction mixture was then washed with 5 mL of 1 N HCl and the aqueous layer was extracted with seven 2-mL portions of dichloromethane. The combined organic layer was washed with water and brine and then dried (MgSO$_4$). The solvent was concentrated under diminished pressure to afford a crude residue. The residue was applied to a silica gel column (24×3 cm). Elution with diethyl ether gave compound 14 as a dark red solid: yield 34 mg (30%); silica gel TLC $R_f$ 0.16 (1:1 ethyl acetate-hexanes); $^1$H NMR (CDCl$_3$) δ 0.87 (t, 3H, J=6.80 Hz), 0.93 (t, 3H, J=7.40 Hz), 1.11-1.52 (m, 24H), 1.53-1.68 (m, 2H), 1.99 (quin, 2H, J=6.90 Hz), 2.32-2.54 (m, 4H), 3.23 (q, 2H, J=6.60 Hz), 4.10 (t, 2H, J=6.70 Hz), 5.36 (s, 1H), 6.58 (s, 1H) and 8.09 (s, 1H); $^{13}$C NMR (CDCl$_3$) δ 13.8, 14.3, 19.3, 22.79, 22.84, 23.3, 28.2, 29.5, 29.6, 29.7, 29.80, 29.82, 30.7, 31.6, 32.1, 42.3, 64.9, 91.9, 116, 149.8, 155.1, 172.9, 179 and 182.6; mass spectrum (APCI), m/z 464.3374 (M+H)$^+$ (C$_{27}$H$_{46}$NO$_5$ requires 464.3376).

Example 9: Preparation of Butyl 4-(4-methoxy-3,6-dioxo-5-tridecylcyclohexa-1,4-dienylamino)butanoate (15)

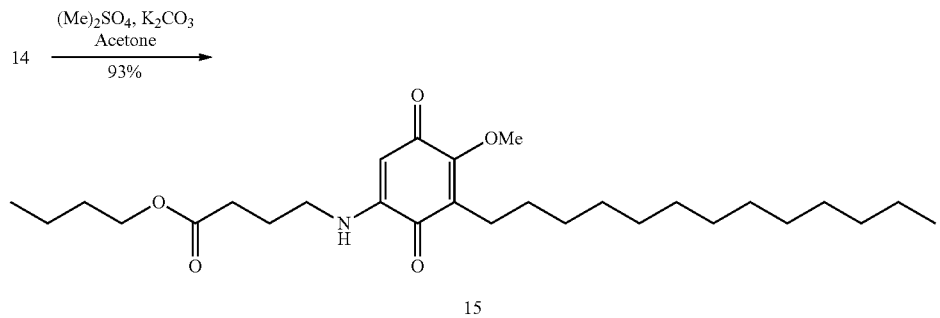

To a solution containing 8.0 mg (16 μmol) of hydroxyquinone 14 and 84 mg (0.6 mmol) of potassium carbonate in 1.0 mL of anh acetone was added dropwise 30 μL (0.3 mmol) of dimethyl sulfate. The reaction mixture was heated to reflux overnight and allowed to cool to room temperature. The crude reaction mixture was concentrated under diminished pressure and redissolved in 10 mL of dichloromethane. The organic layer was washed with 5 mL of 1 N HCl and the aqueous layer was extracted with three 10-mL portions of dichloromethane. The combined organic layer was dried (MgSO$_4$) and concentrated under diminished pressure to afford a crude residue. The residue was applied to a silica gel column (24×2 cm). Step gradient elution with 20% diethyl ether→30% diethyl ether in hexane gave compound 15 as a bright red solid: yield 7.7 mg (93%); silica gel TLC R$_f$ 0.67 (1:1 ethyl acetate-hexanes); $^1$H NMR (CDCl$_3$) δ 0.88 (t, 3H, J=6.8 Hz), 0.93 (t, 3H, J=7.4 Hz), 1.16-1.46 (m, 23H), 1.51-1.71 (m, 3H), 1.96 (quin, 2H, J=7.0 Hz), 2.31-2.49 (m, 4H), 3.16 (dd, 2H, J=13 and 6.7 Hz), 4.02-4.15 (m, 5H), 5.28 (s, 1H) and 5.95 (t, 1H, J=5.6 Hz); $^{13}$C NMR (CDCl$_3$) δ 13.9, 14.3, 19.3, 22.8, 23.1, 23.5, 28.8, 29.5, 29.6, 29.73, 29.81, 29.84, 30.8, 31.7, 32.1, 42.1, 61.8, 64.9, 96.2, 127.7, 146.9, 158.5, 173, 181.8 and 184; mass spectrum (APCI), m/z 478.3516 (M+H)$^+$ (C$_{28}$H$_{48}$NO$_5$ requires 478.3532).

Example 10: Preparation of hexyl 4-(4-hydroxy-3,6-dioxo-5-tridecylcyclohexa-1,4-dienylamino)butanoate (17)

a. Tosylate Salt (16)

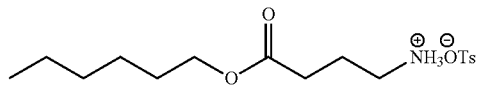

A solution of 1.00 g (9.70 mmol) of 4-aminobutanoic acid, 2.02 g (1.08 mmol) of p-toluenesulfonic acid monohydrate and 1.51 mL (1.23 g, 1.24 mmol) of 1-hexanol in 20 mL of toluene was heated to reflux, using a Dean-Stark distilling receiver, for 24 h. The reaction mixture was allowed to cool to room temperature and diluted with 20 mL of anh diethyl ether to afford p-toluenesulfonate salt 16 as a crystalline, colorless solid: yield 2.50 g (72%); silica gel TLC R$_f$ 0.22 (9:1 chloroform-methanol); $^1$H NMR (CDCl$_3$) δ 0.88 (t, 3H, J=7.20 Hz), 1.21-1.35 (m, 6H), 1.55 (quin, 2H, J=14.0 and 7.20 Hz), 1.85 (quin, 2H, J=14.8 and 7.30 Hz), 2.27 (t, 2H, J=7.30 Hz), 2.36 (s, 3H), 2.80-2.92 (m, 2H), 3.98 (t, 2H, J=6.90 Hz), 7.18 (d, 2H, J=7.90 Hz) and 7.72-7.83 (m, 5H); $^{13}$C NMR (CDCl$_3$) δ 14.2, 21.5, 22.67, 22.71, 25.7, 28.6, 31.0, 31.6, 39.4, 65.0, 126.1, 129.2, 140.9, 141.2 and 172.6.

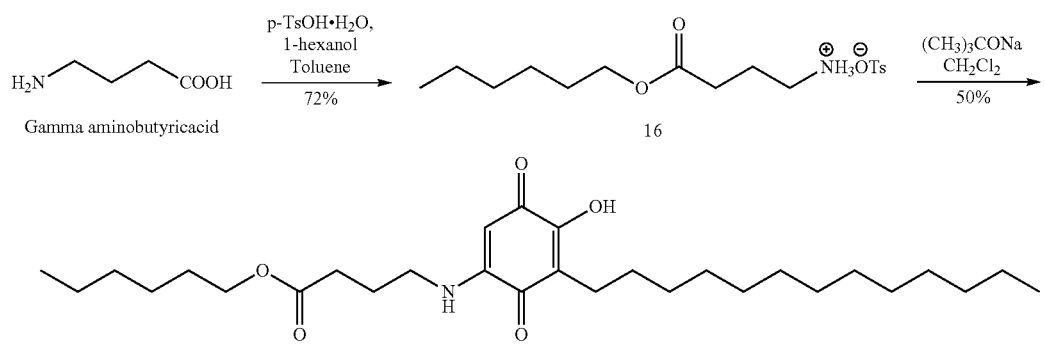

b. Hexyl 4-(4-hydroxy-3,6-dioxo-5-tridecylcyclo-hexa-1,4-dienylamino)butanoate (17)

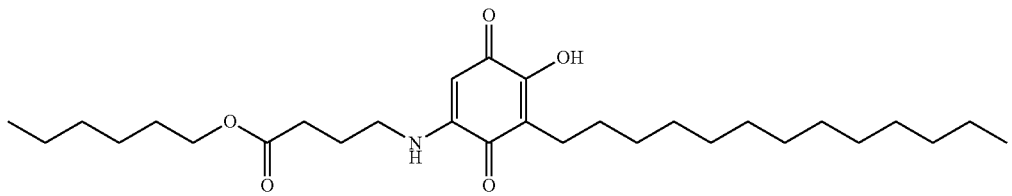 [SMILES: CCCCCCCCCCCCCC1=C(O)C(=O)C=C(NCCCC(=O)OCCCCCC)C1=O]

To a solution containing 37.0 mg (0.11 mmol) of 2-hydroxy-5-methoxy-3-tridecyl-(1,4)-benzoquinone (5) in 5.2 mL of dichloromethane was added a solution containing 119 mg (0.33 mmol) of p-toluenesulfonate salt 16 and 33.0 mg (97%, 0.33 mmol) of potassium tert-butoxide in 5.2 mL of dichloromethane dropwise. The reaction mixture was stirred at room temperature for 20 h under an argon atmosphere. The reaction mixture was then washed with 5 mL of 1 N HCl and the aqueous layer was extracted with seven 2-mL portions of dichloromethane. The combined organic layer was washed with water and brine and then dried ($Na_2SO_4$). The solvent was concentrated under diminished pressure to afford a crude residue. The residue was applied to a silica gel column (24×3 cm). Elution with diethyl ether gave compound 17 as a dark red solid: yield 27 mg (50%); silica gel TLC $R_f$ 0.40 (1:1 ethyl acetate-hexanes); $^1$H NMR ($CDCl_3$) δ 0.85-0.90 (m, 6H), 1.18-1.51 (m, 28H), 1.58-1.65 (m, 2H), 1.99 (quin, 2H, J=14.0 and 7.20 Hz), 2.35-2.43 (m, 4H), 3.23 (q, 2H, J=6.70 Hz), 4.09 (t, 2H, J=6.80 Hz), 5.36 (s, 1H), 6.58 (s, 1H) and 8.08 (s, 1H); $^{13}$C NMR ($CDCl_3$) δ 14.1, 14.3, 22.70, 22.79, 22.83, 23.3, 25.7, 28.2, 28.7, 29.5, 29.6, 29.7, 29.80, 29.82, 31.5, 31.6, 32.1, 42.3, 65.2, 91.9, 116, 149.8, 155.1, 172.9, 179 and 182.6; mass spectrum (APCI), m/z 492.3684 $(M+H)^+$ ($C_{29}H_{50}NO_5$ requires 492.3689).

Example 11: Preparation of Hexyl 4-(4-methoxy-3,6-dioxo-5-tridecylcyclohexa-1,4-dienylamino)butanoate (18)

To a solution containing 29 mg (59 μmol) of hydroxyquinone 17 and 0.3 g (2.2 mmol) of potassium carbonate in 1.5 mL of anh acetone was added dropwise 28 μL (37 mg, 0.3 mmol) of dimethyl sulfate. The reaction mixture was heated to reflux overnight, allowed to cool to room temperature and concentrated under diminished pressure to afford a crude residue. The residue was redissolved in 10 mL of dichloromethane and washed with 5 mL of 1 N HCl. The aqueous layer was then extracted with three 10-mL portions of dichloromethane. The combined organic layer was dried ($MgSO_4$) and concentrated under diminished pressure to afford a crude residue. The residue was applied to a silica gel column (23×2 cm). Step gradient elution with 20% diethyl ether→30% diethyl ether in hexane gave compound 18 as a bright red solid: yield 8 mg (27%); silica gel TLC $R_f$ 0.40 (1:1 ethyl acetate-hexanes); $^1$H NMR ($CDCl_3$) δ 0.81-0.97 (m, 6H), 1.15-1.45 (m, 28H), 1.54-1.70 (m, 2H), 1.96 (quin, 2H, J=11.2 and 5.60 Hz), 2.31-2.48 (m, 4H), 3.16 (q, 2H, J=6.60 Hz), 4.02-4.21 (m, 5H), 5.26 (s, 1H) and 5.87-6.06 (m, 1H); $^{13}$C NMR ($CDCl_3$) δ 14.1, 14.3, 15.4, 22.7, 22.8, 23.1, 23.5, 25.7, 28.7, 28.8, 29.5, 29.6, 29.7, 29.80, 29.84, 31.6, 31.8, 32.1, 42.1, 61.7, 65.2, 66.0, 96.2, 127.6, 146.9, 158.5, 173.0, 181.7 and 183.9; mass spectrum (APCI), m/z 506.3836 $(M+H)^+$ ($C_{30}H_{52}NO_5$ requires 506.3845).

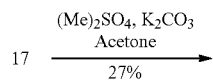

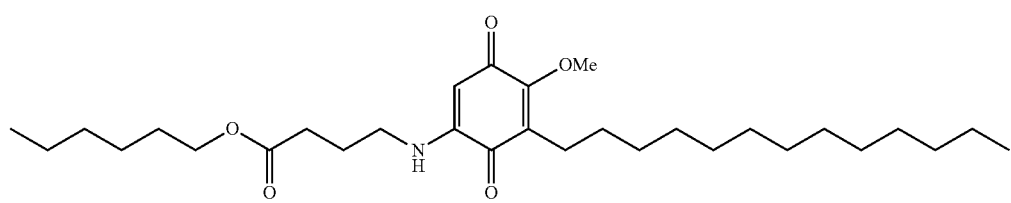

18

Example 12: Preparation of 5-(hexylamino)-2-hydroxy-3-tridecylcyclohexa-2,5-diene-1,4-dione (19)

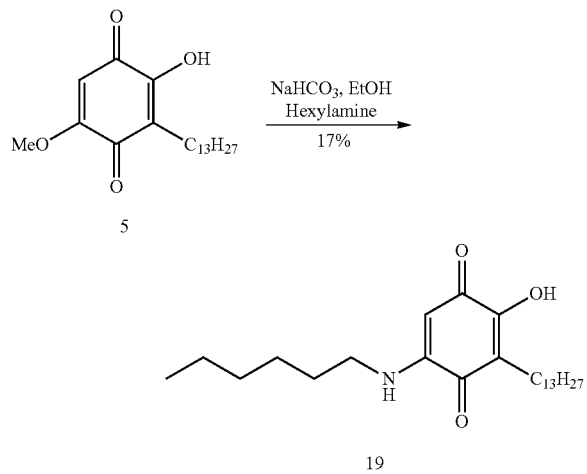

To a solution containing 49.0 mg (0.15 mmol) of 2-hydroxy-5-methoxy-3-tridecyl-(1,4)-benzoquinone (5) in 12 mL of EtOH was added 97.0 µL (74.0 mg, 0.73 mmol) of hexylamine dropwise followed by 1.20 g (14.6 mmol) of NaHCO$_3$. The reaction mixture was stirred at room temperature for 20 h under an argon atmosphere and then washed with 5 mL of 1 N HCl. The aqueous layer was extracted with seven 2-mL portions of dichloromethane. The combined organic layer was washed with water and brine and then dried (Na$_2$SO$_4$). The solvent was concentrated under diminished pressure to afford a crude residue. The residue was applied to a silica gel column (24×3 cm). Elution with 10% diethyl ether in hexane gave compound 19 as a dark red solid: yield 10.0 mg (17%); mp 70° C. (dec); silica gel TLC R$_f$ 0.53 (1:1 ethyl acetate-hexanes); $^1$H NMR (CDCl$_3$) δ 0.81-0.96 (m, 6H), 1.16-1.50 (m, 28H), 1.65 (quin, 2H, J=14.4 and 6.8 Hz), 2.30-2.43 (m, 2H), 3.15 (dd, 2H, J=12.8 and 6.4 Hz), 3.22-3.34 (br s, 1H), 5.32 (s, 1H) and 6.41 (s, 1H); $^{13}$C NMR (CDCl$_3$) δ 14.1, 14.3, 22.6, 22.79, 22.84, 26.8, 28.2, 28.3, 29.51, 29.56, 29.6, 29.7, 29.81, 29.83, 31.4, 31.5, 32.0, 32.1, 43.0, 91.6, 115.8, 149.8, 155.3, 178.8 and 182.7; IR (thin film): 3260, 1640, 1560, 1230 cm$^{-1}$; mass spectrum (APCI), m/z 406.3313 (M+H)$^+$ (C$_{25}$H$_{44}$NO$_3$ requires 406.3321).

Example 13: Preparation of 5-(hexylamino)-2-methoxy-3-tridecylcyclohexa-2,5-diene-1,4-dione (20)

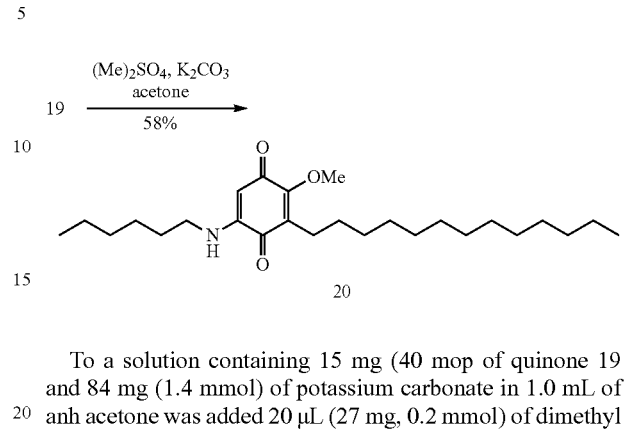

To a solution containing 15 mg (40 mop of quinone 19 and 84 mg (1.4 mmol) of potassium carbonate in 1.0 mL of anh acetone was added 20 µL (27 mg, 0.2 mmol) of dimethyl sulfate. The reaction mixture was heated to reflux for 3 h and stirred at room temperature overnight. The reaction mixture was then concentrated under diminished pressure and the crude residue was redissolved in 10 mL of dichloromethane and washed with 5 mL of 1 N HCl. The aqueous layer was extracted with three 10-mL portions of dichloromethane. The combined organic layer was dried (MgSO$_4$) and concentrated under diminished pressure to afford a crude residue. The residue was applied to a silica gel column (24×2 cm). Elution with 10% diethyl ether in hexane gave compound 20 as a bright red solid: yield 9.0 mg (58%); mp 110° C. (dec); silica gel TLC R$_f$ 0.76 (1:1 ethyl acetate-hexanes); $^1$H NMR (CDCl$_3$) δ 0.82-0.98 (m, 6H), 1.18-1.46 (m, 28H), 1.51-1.73 (m, 2H), 2.27-2.46 (m, 2H), 3.07 (dd, 2H, J=13.2 and 6.4 Hz), 4.11 (s, 3H), 5.25 (s, 1H) and 5.81 (s, 1H); $^{13}$C NMR (CDCl$_3$) δ 14.1, 14.3, 22.7, 22.8, 23.1, 26.8, 28.3, 28.8, 29.52, 29.60, 29.61, 29.72, 29.73, 29.80, 29.81, 29.83, 31.5, 32.1, 42.7, 61.8, 95.9, 127.5, 146.9, 158.7, 181.7 and 184.1; IR (thin film): 3330, 1600, 1590, 1210 cm$^{-1}$; mass spectrum (APCI), m/z 420.3470 (M+H)$^+$ (C$_{26}$H$_{46}$NO$_3$ requires 420.3478).

Example 14: Preparation of Hexyl 4-((4-hydroxy-3,6-dioxo-5-tridecylcyclohexa-1,4-dienyl)(methyl)amino)butanoate (23)

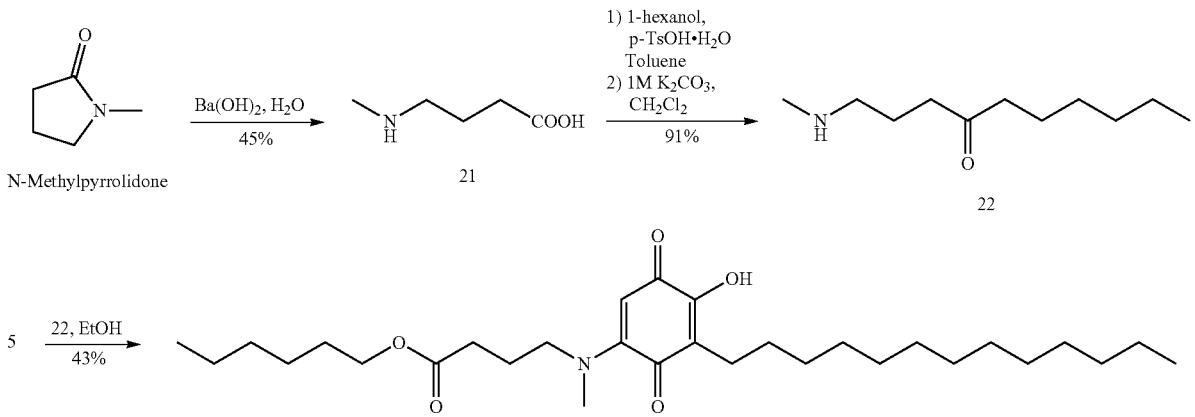

a. 4-(methylamino)butanoic Acid (21)

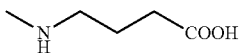

To a solution containing 9.70 g (104 mmol) of N-methyl-2-pyrrolidone in 111 mL of distilled water was added 10.9 g (63.5 mmol) of $Ba(OH)_2$. The heterogeneous mixture was heated to reflux for 5 h and then cooled to 0° C. and saturated with $CO_2$ gas (dry ice). The resulting white precipitate was collected by filtration and washed with cold water. The clear filtrate was concentrated under diminished pressure and the resulting moist residue was triturated with acetonitrile, filtered and washed with ether. The crude residue thus obtained was further dried by co-evaporating three times with toluene and triturated with methanol to yield N-methyl butyric acid (21) as a colorless solid: yield 5.45 g (45%); $^1$H NMR (DMSO-$d_6$) δ 1.09 (quin, 2H, J=13.6 and 6.80 Hz), 1.41-1.59 (m, 2H), 1.86 (d, 3H, J=0.90 Hz), 2.20 (t, 2H, J=6.90 Hz), 2.50-2.57 (m, 1H) and 4.67 (s, 1H); $^{13}$C NMR (DMSO-$d_6$) δ 14.0, 23.2, 27.0, 41.0 and 171.3.

b. 1-(methylamino)decan-4-one (22)

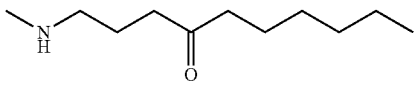

A solution containing 3.52 g (30.0 mmol) of 4-(N-methylamino)butanoic acid (21), 6.25 g (32.4 mmol) of p-toluenesulfonic acid hydrate and 4.70 mL (3.82 g, 37.2 mmol) of 1-hexanol in 62 mL of toluene was heated to reflux using a Dean-Stark distilling receiver for 12 h. The cooled reaction mixture was concentrated under diminished pressure to afford a crude residue. The residue was dissolved in 10 mL of hexane and the resulting solution cooled to −72° C. for 40 min and filtered to yield the amine 22 as its tosylate salt. The tosylate salt obtained was dissolved in 100 mL of dichloromethane and washed with 1 M $K_2CO_3$. The organic layer was dried ($MgSO_4$) and concentrated under diminished pressure to generate the free amine 22 as a colorless oil: yield 5.50 g (91%); $^1$H NMR (CDCl$_3$) δ 0.73-0.87 (m, 3H), 1.15-1.34 (m, 6H), 1.48-1.60 (m, 2H), 1.73 (quin, 2H, J=14.4 and 7.20 Hz), 2.22-2.32 (m, 2H), 2.35 (d, 3H, J=10.7 Hz), 2.52 (t, 2H, J=7.10 Hz) and 3.88-4.07 (m, 2H); $^{13}$C NMR (CDCl$_3$) δ 14.0, 22.5, 25.1, 25.6, 28.6, 31.4, 32.1, 36.3, 50.9, 64.6 and 173.6.

c. hexyl 4-((4-hydroxy-3,6-dioxo-5-tridecylcyclohexa-1,4-dienyl)(methyl)amino)-butanoate (23)

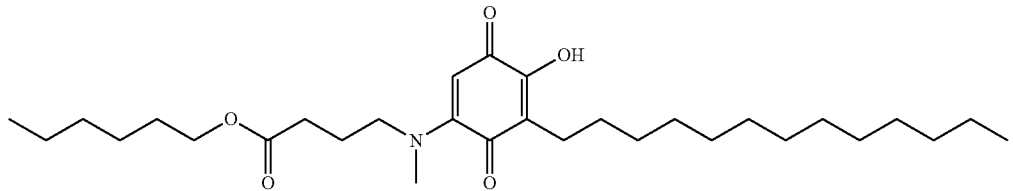 [SMILES: CCCCCCCCCCCCCC1=C(O)C(=O)C=C(N(C)CCCC(=O)OCCCCCC)C1=O]

To a solution containing 60.0 mg (0.18 mmol) of 2-hydroxy-5-methoxy-3-tridecyl-(1,4)-benzoquinone (5) in ethanol was added 360 mg (1.79 mmol) of amine 22. The reaction mixture was stirred at room temperature for 12 h and then washed with brine and dried ($MgSO_4$). The organic layer was concentrated under diminished pressure to afford the crude residue. The residue was applied to a silica gel column (24×2 cm). Elution with 60:1 dichloromethane-methanol gave compound 23 as a red solid: yield 39.0 mg (43%); silica gel TLC $R_f$ 0.32 (1:1 ethyl acetate-hexanes); $^1$H NMR (CDCl$_3$) δ 0.81-0.95 (m, 6H), 1.19-1.28 (m, 14H), 1.27-1.37 (m, 12H), 1.36-1.48 (m, 2H), 1.51-1.68 (m, 2H), 2.00 (quin, 2H, J=15 and 7.5 Hz), 2.38 (t, 4H, J=7.5 Hz), 3.14 (s, 3H), 3.63 (t, 3H, J=7.0 Hz), 4.07 (t, 2H, J=7.0 Hz) and 5.49 (s, 1H); $^{13}$C NMR (CDCl$_3$) δ 14.1, 14.3, 22.7, 22.8, 23.2, 25.6, 25.7, 28.5, 28.7, 29.5, 29.6, 29.78, 29.79, 29.81, 29.83, 29.87, 31.2, 31.6, 31.8, 32.1, 32.9, 54.4, 63.2, 65.0, 98.0, 117.5, 153.0, 172.9, 178.7 and 184.6; mass spectrum (APCI), m/z 506.3848 (M+H)$^+$ ($C_{30}H_{51}NO_5$ requires 506.3845).

Example 15: Preparation of Hexyl 4-((4-methoxy-3,6-dioxo-5-tridecylcyclohexa-1,4-dienyl)(methyl)amino)butanoate (24)

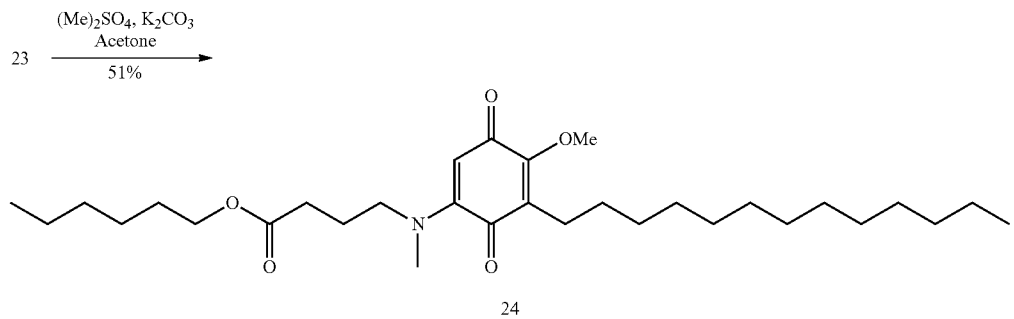

To a solution containing 19 mg (40 μmol) of hydroxyquinone 23 in anh acetone was added 0.2 g (1.4 mmol) of potassium carbonate and 20 μL (27 mg, 0.2 mmol) of dimethyl sulfate dropwise. The reaction mixture was heated to reflux for 1.5 h and cooled to room temperature and stirred at 23° C. for 12 h. The reaction mixture was concentrated under diminished pressure and redissolved in 50 mL of dichloromethane. The organic layer was washed with brine, dried ($MgSO_4$) and concentrated under diminished pressure to afford a crude red residue. The residue was applied to a silica gel column (24×2 cm). Elution with 60:1 dichloromethane-methanol gave compound 24 as a red solid: yield 10 mg (51%); silica gel TLC $R_f$ 0.61 (1:1 ethyl acetate-hexanes); $^1$H NMR ($CDCl_3$) δ 0.84-0.91 (m, 6H), 1.20-1.40 (m, 26H), 1.55-1.68 (m, 4H), 1.97 (2H, quin, J=14.5 and 7.00 Hz), 2.31-2.39 (m, 4H), 2.99 (s, 3H), 3.50-3.59 (m, 2H), 4.00-4.19 (m, 5H) and 5.40 (s, 1H); $^{13}$C NMR ($CDCl_3$) δ 22.7, 22.8, 23.3, 23.6, 25.7, 28.7, 29.1, 29.5, 29.6, 29.72, 29.76, 29.81, 29.83, 29.92, 29.98, 31.3, 31.6, 32.1, 40.6, 53.6, 61.3, 65.0, 95.8, 102.4, 129.6, 150.9, 156.6, 173.1, 181.5 and 185.7; mass spectrum (APCI), m/z 520.4002 (M+H)$^+$ ($C_{31}H_{54}NO_5$ requires 520.4002).

Example 16: Preparation of 5-(dimethylamino)-2-hydroxy-3-tridecylcyclohexa-2,5-diene-1,4-dione (25)

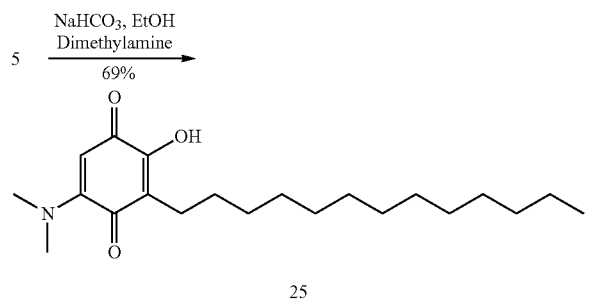

To a solution containing 38.0 mg (0.11 mmol) of 2-hydroxy-5-methoxy-3-tridecyl-(1,4)-benzoquinone (5) in 12 mL of ethanol was added 470 mg (5.65 mmol) of $NaHCO_3$ and 140 μL (126 mg, 1.12 mmol) of a 40% by wt solution of dimethylamine in water dropwise. The reaction mixture was stirred at room temperature for 20 h and then concentrated under diminished pressure to afford a crude residue. The residue was diluted with 50 mL of dichloromethane. The organic layer was washed with two 10-mL portions of 1 N HCl, dried ($MgSO_4$) and then concentrated under diminished pressure to afford a red solid. The crude residue was applied to a silica gel column (20×2 cm). Elution with 60:1 dichloromethane-methanol gave compound 25 as a red solid: yield 27 mg (69%); silica gel TLC $R_f$ 0.36 (1:1 ethyl acetate-hexanes); $^1$H NMR ($CDCl_3$) δ 0.87 (t, 3H, J=7.20 Hz), 1.20-1.35 (m, 16H), 1.36-1.48 (m, 4H), 2.34-2.47 (m, 4H), 3.23 (br s, 6H), 3.85 (s, 1H) and 5.48 (s, 1H); $^{13}$C NMR ($CDCl_3$) δ 14.3, 22.8, 23.2, 28.4, 29.51, 29.56, 29.6, 29.71, 29.78, 29.81, 29.82, 29.83, 29.85, 32.1, 43.7, 56.9, 97.6, 102.3, 117.2, 153.7 and 185.0; mass spectrum (APCI), m/z 350.2692 (M+H)$^+$ ($C_{21}H_{36}NO_3$ requires 350.2695).

Example 17: Preparation of 5-(dimethylamino)-2-methoxy-3-tridecylcyclohexa-2,5-diene-1,4-dione (26)

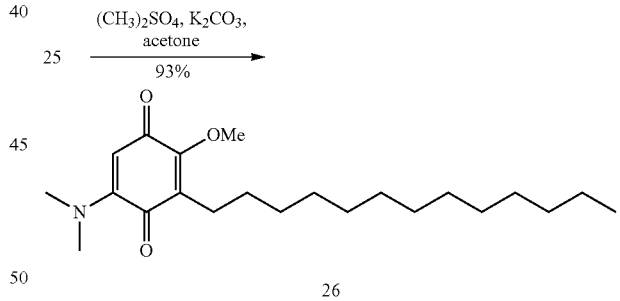

To a solution containing 26.0 mg (74.0 μmol) of hydroxyquinone 25 in 7.4 mL of anh acetone was added 388 mg (2.81 mmol) of potassium carbonate and 35.0 μL (47.0 mg, 0.37 mmol) of dimethyl sulfate dropwise. The reaction mixture was heated to reflux for 1.5 h and allowed to cool to room temperature and then stirred for another 12 h. The reaction mixture was concentrated under diminished pressure and then diluted with 50 mL of dichloromethane. The organic layer was washed with 10 mL brine and dried ($Na_2SO_4$), then concentrated under diminished pressure to afford a crude residue. The residue was applied to a silica gel column (20×2 cm). Elution with dichloromethane gave compound 26 as a red solid: yield 25 mg (93%); silica gel TLC $R_f$ 0.50 (1:1 ethyl acetate-hexanes); $^1$H NMR ($CDCl_3$) δ 0.87 (t, 3H, J=6.8 Hz), 1.20-1.32 (m, 20H), 1.33-1.45 (m, 2H), 2.29-2.44 (m, 2H), 3.12 (s, 6H), 4.06 (s, 3H) and 5.38 (s, 1H); $^{13}$C NMR (CDCl$_3$) δ 14.3, 22.8, 23.6, 29.0, 29.5, 29.6, 29.7, 29.80, 29.82, 29.83, 29.9, 32.1, 42.8, 61.3, 102.3, 129.5, 151.4, 156.8, 181.4 and 185.9; mass spectrum (APCI), m/z 364.2859 (M+H)$^+$ (C$_{22}$H$_{38}$NO$_3$ requires 364.2852).

Example 18: Preparation of tert-butyl 4-((4-hydroxy-3,6-dioxo-5-tridecylcyclohexa-1,4-dienyl)(methyl)amino)-butanoate (29)

tert-butylacetate and 130 μL (1.48 mmol) of 70% perchloric acid was added dropwise. The reaction mixture was stirred at room temperature for 18 h and quenched by the addition of 20 mL of satd aq NaHCO$_3$. The aqueous layer was extracted with three 30-mL portions of dichloromethane. The combined organic layer was washed with water and brine and then dried (MgSO$_4$). The solvent was concentrated under diminished pressure to afford a crude residue. The residue was applied to a silica gel column (20×3 cm). Elution with 1:5 ethyl acetate-hexanes afforded compound 27 as a colorless oil: yield 372 mg (29% over two steps);

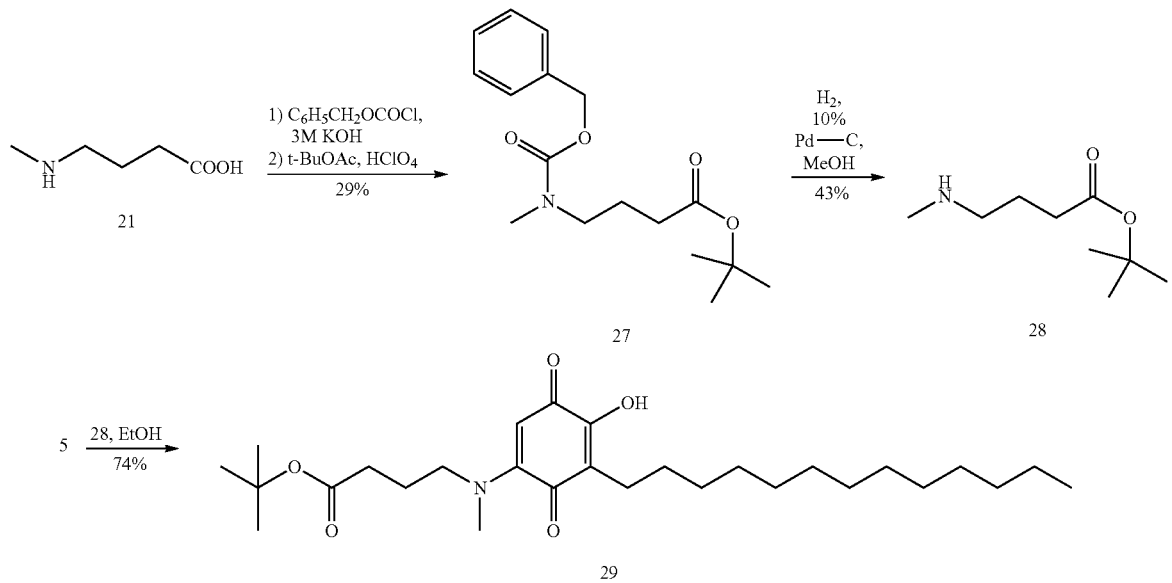

a. tert-butyl 4-((benzyloxycarbonyl)(methyl)amino)butanoate (27)

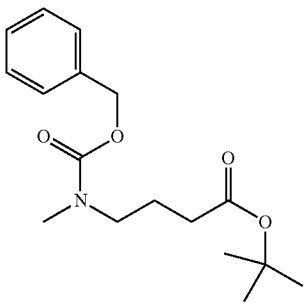 [SMILES: CN(CCCC(=O)OC(C)(C)C)C(=O)OCc1ccccc1]

silica gel TLC R$_f$ 0.52 (1:1 ethyl acetate-hexanes); $^1$H NMR (CDCl$_3$) δ 1.42 (s, 9H), 1.81 (dd, 2H, J=15.6 and 6.80 Hz), 2.15-2.26 (m, 2H), 2.91 (s, 3H), 3.20 (br s, 2H), 5.11 (s, 2H) and 7.25-7.38 (m, 5H); $^{13}$C NMR (CDCl$_3$) δ 22.8, 27.8, 32.2, 34.0, 47.9, 66.7, 79.9, 127.5, 127.6, 128.2, 136.7, 155.9 and 171.9.

b. tert-butyl 4-(methylamino)butanoate (28)

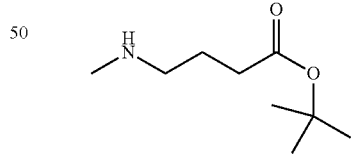

To a solution containing 900 mg (7.68 mmol) of acid 21 in 10.3 mL of 3 M aq KOH was added 1.14 mL (1.36 g, 7.68 mmol) of 95% benzyl chloroformate dropwise over a period of 10 min under an argon atmosphere. The reaction mixture was stirred at room temperature for 2 h and quenched by the addition of 7.9 mL of 5 M aq HCl solution dropwise. The aqueous layer was extracted with three 30-mL portions of ethyl acetate. The combined organic extract was washed with water and brine and then dried (MgSO$_4$). The solvent was concentrated under diminished pressure to afford a crude residue. The residue was dissolved in 8.5 mL of To a solution containing 372 mg (1.21 mmol) of ester 27 in 4.4 mL of methanol was added 40.0 mg of 10% Pd—C. Hydrogen gas was bubbled through the solution for 2 h under atmospheric pressure. The catalyst was removed by filtration through a pad of Celite and the filtrate was concentrated under diminished pressure carefully (as the product is volatile) to afford compound 28 as a colorless oil: yield 91 mg (43%); $^1$H NMR (CDCl$_3$) δ 1.40 (s, 9H), 2.01-2.11 (m, 2H), 2.31 (t, 2H, J=7.10 Hz), 2.64 (s, 3H), 2.95 (dd, 2H, J=13.0 and 5.10 Hz) and 8.48 (br s, 1H); $^{13}$C NMR (CDCl$_3$) δ 21.7, 28.2, 32.4, 33.2, 48.9, 81.0 and 171.7.

c. tert-butyl 4-((4-hydroxy-3,6-dioxo-5-tridecylcyclohexa-1,4-dienyl)(methyl)amino)-butanoate (29)

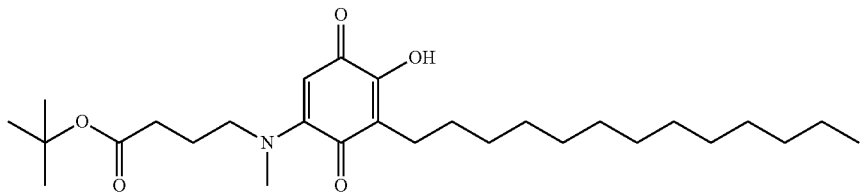 [SMILES: CCCCCCCCCCCCCC1=C(O)C(=O)C=C(N(C)CCCC(=O)OC(C)(C)C)C1=O]

To a solution containing 71.0 mg (0.21 mmol) of 2-hydroxy-5-methoxy-3-tridecyl-(1,4)-benzoquinone (5) in ethanol was added 730 mg (4.21 mmol) of the amine 28. The reaction mixture was stirred at room temperature for 12 h, concentrated under diminished pressure and diluted by the addition of 20 mL of dichloromethane. The organic layer was washed with brine and dried (MgSO$_4$), then concentrated under diminished pressure to afford the crude residue as a red solid. The residue applied to a silica gel column (20×3 cm). Elution with 9:1 hexane-ethyl acetate gave compound 29 as a red solid: yield 75 mg (74%); silica gel TLC R$_f$ 0.45 (1:1 ethyl acetate-hexanes); $^1$H NMR (CDCl$_3$) δ 0.85 (t, 3H, J=6.70 Hz), 1.18-1.31 (m, 22H), 1.43 (s, 9H), 1.94 (dt, 2H, J=14.0 and 6.90 Hz), 2.27 (t, 2H, J=7.00 Hz), 2.32-2.39 (m, 2H), 3.08 (br s, 3H), 3.59 (br s, 2H) and 5.48 (s, 1H); $^{13}$C NMR (CDCl$_3$) δ 14.2, 22.8, 23.1, 28.2, 28.4, 29.4, 29.6, 29.73, 29.75, 29.77, 29.78, 29.8, 32.0, 32.4, 41.4, 54.5, 80.8, 97.6, 117.4, 153.0, 153.3, 172.1, 178.6 and 184.8; mass spectrum (APCI), m/z 478.3533 (M+H)$^+$ (C$_{28}$H$_{48}$NO$_5$ requires 478.3532).

Example 19: Preparation of tert-butyl 4-((4-methoxy-3,6-dioxo-5-tridecylcyclohexa-1,4-dienyl)(methyl)amino)-butanoate (30)

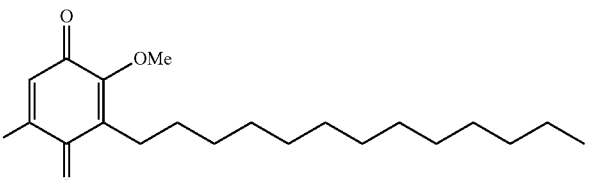

To a solution containing 43.0 mg (0.09 mmol) of hydroxyquinone 29 in 2.5 mL of anh acetone was added 473 mg (3.42 mmol) of potassium carbonate and 50.0 µL (66.0 mg, 0.45 mmol) of dimethyl sulfate dropwise. The reaction mixture was heated to reflux for 3 h and allowed to cool to room temperature, then concentrated under diminished pressure to afford a crude residue. The residue was dissolved in 50 mL of dichloromethane, washed with brine and then dried (MgSO$_4$). The organic layer was concentrated under diminished pressure to afford a crude red residue. The residue was applied to a silica gel column (20×3 cm). Elution with 60:1 dichloromethane-methanol gave compound 30 as a red solid: yield 30 mg (42%); silica gel TLC R$_f$ 0.58 (1:1 ethyl acetate-hexanes); $^1$H NMR (CDCl$_3$) δ 0.87 (t, 3H, J=6.90 Hz), 1.22-1.32 (m, 20H), 1.33-1.39 (m, 2H), 1.44 (s, 9H), 1.92 (dt, 2H, J=14.8 and 7.30 Hz), 2.26 (t, 2H, J=7.20 Hz), 2.33-2.39 (m, 2H), 2.99 (s, 3H), 3.48-3.55 (m, 2H), 4.05 (s, 3H) and 5.40 (s, 1H); $^{13}$C NMR (CDCl$_3$) δ 14.2, 22.8, 23.4, 23.6, 28.20, 28.24, 29.0, 29.5, 29.6, 29.74, 29.79, 29.81, 29.83, 30.0, 32.1, 32.5, 40.6, 53.7, 61.3, 80.7, 102.3, 129.6, 150.9, 156.6, 172.3, 181.4 and 185.7; mass spectrum (APCI), m/z 492.3695 (M+H)$^+$ (C$_{29}$H$_{50}$NO$_5$ requires 492.3689).

Example 20: Preparation of 1,2,4,5-tetramethoxy-3-(undec-10-enyl)benzene (34)

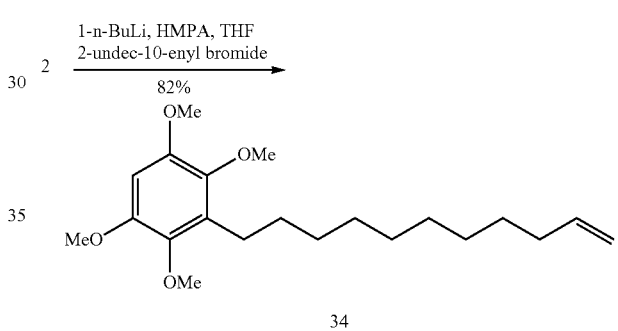

To a solution containing 630 mg (3.18 mmol) of 1,2,4,5-tetramethoxybenzene (2) and 56.0 µL (58.0 mg, 0.32 mmol) of hexamethyl phosphoramide in 16 mL of anh THF was added 1.40 mL (2.5 M in hexanes, 3.50 mmol) of n-butyl-lithium dropwise at −40° C. over a period of 1 h. The reaction mixture was allowed to warm to −10° C. over a period of 2 h and 770 µL (0.82 g, 3.50 mmol) of purified 11-bromoundec-1-ene was added. The reaction mixture was stirred at room temperature under an argon atmosphere for 15 h and quenched by the addition of 20 mL of satd aq NH$_4$Cl solution. The aqueous layer was extracted with five 10-mL portions of diethyl ether. The combined organic layer was washed with water and brine and then dried (MgSO$_4$). The solvent was concentrated under diminished pressure to afford a crude residue. The residue was applied to a silica gel column (6×3 cm). Step gradient elution with hexane→2:1 hexane-ethyl acetate afforded 34 as a colorless oil: yield 0.91 g (82%); mp 33-34° C.; silica gel TLC $R_f$ 0.83 (1:1 ethyl acetate-hexanes); $^1$H NMR (CDCl$_3$) δ 1.23-1.43 (m, 12H), 1.49-1.56 (m, 2H), 2.03 (q, 2H, J=14.4 and 6.8 Hz), 2.59-2.63 (m, 2H), 3.77 (s, 6H), 3.84 (s, 6H), 4.90-5.00 (m, 2H), 5.76-5.86 (m, 1H) and 6.41 (s, 1H); $^{13}$C NMR (CDCl$_3$) δ 24.8, 29.1, 29.3, 29.59, 29.64, 29.65, 30.1, 30.9, 33.9, 56.3, 61.0, 96.7, 114.2, 131.2, 139.4, 141.2 and 148.9; IR (thin film): 2850, 1590, 1480, 1220 cm$^{-1}$; mass spectrum (EI), m/z 350.2451 (M)$^+$ (C$_{21}$H$_{34}$O$_4$ requires 350.2457).

Example 21: Preparation of 2,5-dimethoxy-3-(undec-10-enyl)cyclohexa-2,5-diene-1,4-dione (35) and 2-hydroxy-5-methoxy-3-(undec-10-enyl)cyclohexa-2,5-diene-1,4-dione (36)

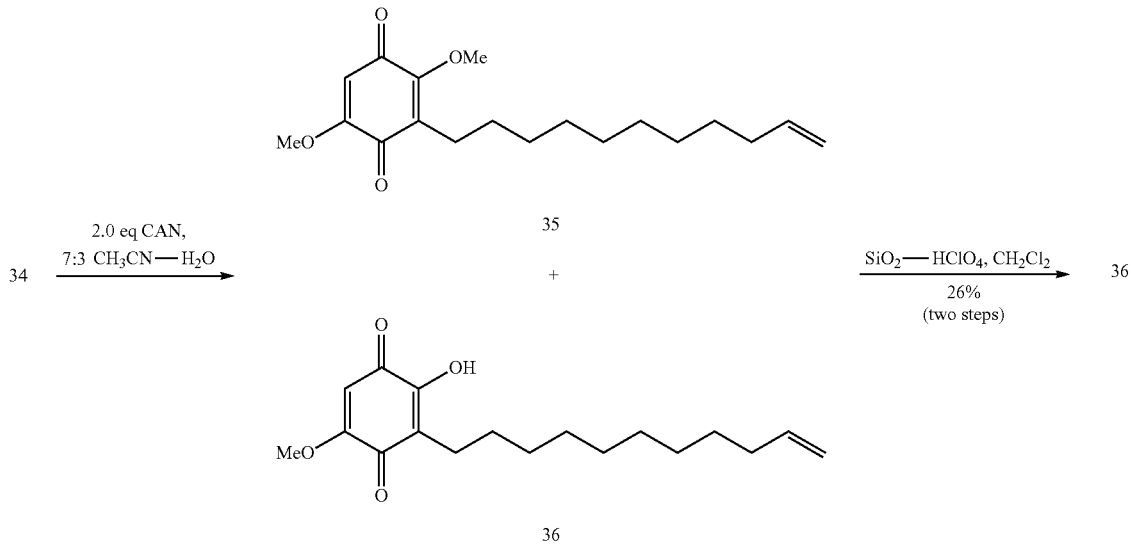

To a solution containing 3.33 g (9.50 mmol) of alkenyltetramethoxy benzene 34 in 95 mL of acetonitrile was added dropwise a solution containing 10.4 g (19.0 mmol) of cerium (IV) ammonium nitrate in 95 mL of 7:3 acetonitrile-water at −7° C. (salt-ice bath) over a period of 30 min. The reaction mixture was allowed to warm to room temperature and stirred for 3 h and was then quenched by the addition of 300 mL of ether. The organic layer was washed with distilled water and brine and then dried (MgSO$_4$). The solvent was concentrated under diminished pressure to afford a crude mixture of quinones 35 and 36. To the solution of the crude residue dissolved in 95 mL of dichloromethane was added 9.50 g (4.75 mmol) of HClO$_4$—SiO$_2$ and the reaction mixture was stirred at room temperature for 12 h. The reaction mixture was filtered and then concentrated under diminished pressure to afford a crude residue. The residue was applied to a silica gel column (23×3 cm). Elution with 9:1 hexane-ethyl acetate gave compound 36 as a yellow-orange solid: yield 745 mg (26% over two steps); mp 89-90° C.; silica gel TLC $R_f$ 0.46 (1:1 ethyl acetate-hexanes); $^1$H NMR (CDCl$_3$) δ 1.06-1.24 (m, 12H), 1.24-1.35 (m, 2H), 1.86 (q, 2H, J=14.4 and 7.6 Hz), 2.23-2.33 (m, 2H), 3.71 (s, 3H), 4.72-4.88 (m, 2H) and 5.58-5.72 (m, 2H); $^{13}$C NMR (CDCl$_3$) δ 22.6, 28.0, 28.9, 29.1, 29.40, 29.48, 29.50, 29.57, 33.8, 56.8, 102.2, 114.1, 119.3, 139.2, 151.6, 161.1, 181.7 and 182.9; IR (thin film): 3350, 1610, 1600, 1200 cm$^{-1}$; mass spectrum (APCI), m/z 306.1836 (M)$^+$ (C$_{18}$H$_{26}$O$_4$ requires 306.1831).

2,5-dimethoxy-3-(undec-10-enyl)cyclohexa-2,5-diene-1,4-dione (35)

Yellow solid; mp 30-31° C.; silica gel TLC $R_f$ 0.61 (1:1 ethyl acetate-hexanes); $^1$H NMR (CDCl$_3$) δ 1.20-1.44 (m, 14H), 1.97-2.05 (m, 2H), 2.41 (dd, 2H, J=13.4 and 6.2 Hz), 3.79 (s, 3H), 4.03 (s, 3H), 4.87-5.01 (m, 2H), 5.71 (s, 1H) and 5.74-5.84 (m, 1H); $^{13}$C NMR (CDCl$_3$) δ 23.2, 28.8, 29.0, 29.2, 29.45, 29.54, 29.56, 29.7, 33.9, 56.5, 61.4, 105.5, 114.2, 130.8, 139.3, 156.0, 158.9, 182.5 and 183.7; IR (thin film): 1650, 1600, 1320, 1210 cm$^{-1}$; mass spectrum (APCI), m/z 320.1977 (M)$^+$ (C$_{19}$H$_{28}$O$_4$ requires 320.1988).

Example 22: Preparation of 5-(hex-5-enylamino)-2-hydroxy-3-(undec-10-enyl)cyclohexa-2,5-diene-1,4-dione (37)

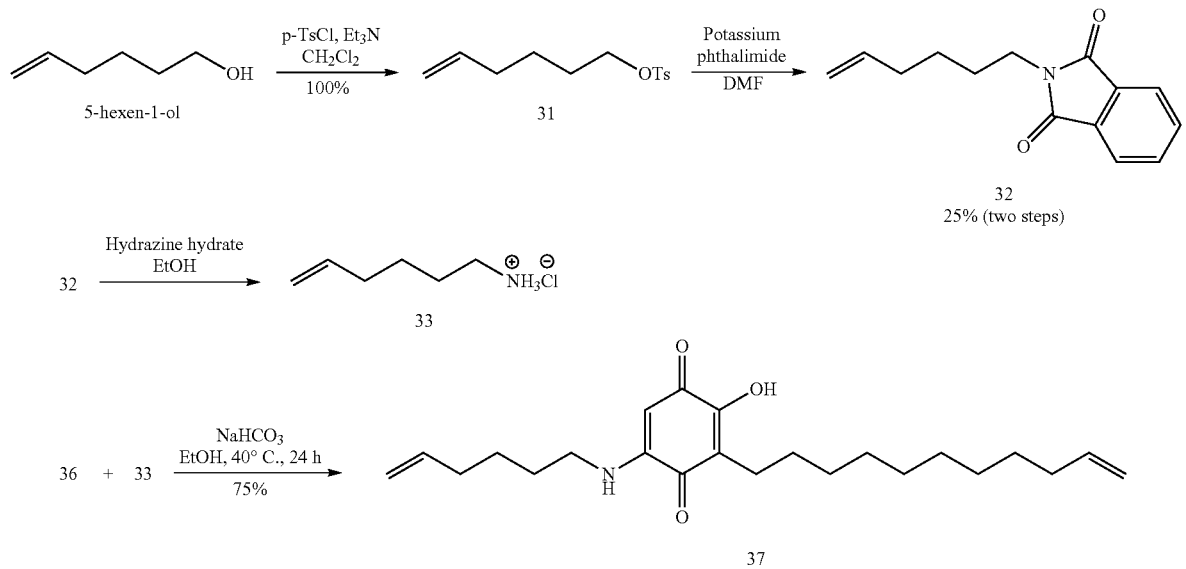

a. hex-5-enyl 4-methylbenzenesulfonate (31)

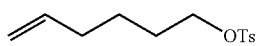 [SMILES: C=CCCCCOS(=O)(=O)c1ccc(C)cc1]

To a solution containing 2.0 g (20 mmol) of 5-hexen-1-ol and 3.1 mL (2.2 g, 5.5 mmol) of triethylamine in 60 mL of anh dichloromethane was added 4.2 g (22 mmol) of p-toluenesulfonyl chloride at 0° C. The reaction mixture was allowed to warm to room temperature and stirred for 12 h. The reaction mixture was then diluted with 100 mL of dichloromethane and washed with two 30-mL portions of 10% aq NaHCO$_3$ and brine. The organic layer was dried (MgSO$_4$) and then concentrated under diminished pressure to afford a crude residue. The residue was purified by flash column chromatography on a silica gel column (24×3 cm). Elution with 4:1 hexanes-ethyl acetate gave compound 31 as a colorless oil: yield 5.07 g (100%); silica gel TLC R$_f$ 0.65 (1:1 ethyl acetate-hexanes); $^1$H NMR (CDCl$_3$) δ 1.41 (quin, 2H, J=15.2 and 7.60 Hz), 1.60-1.71 (m, 2H), 1.97 (q, 2H, J=14.4 and 7.20 Hz), 2.45 (s, 3H), 4.03 (t, 2H, J=6.40 Hz), 4.89-4.95 (m, 2H), 5.65-5.78 (m, 1H), 7.34 (d, 2H, J=8.40 Hz) and 7.79 (d, 2H, J=8.40 Hz); $^{13}$C NMR (CDCl$_3$) δ 21.8, 24.7, 28.3, 33.0, 70.6, 115.2, 128.0, 129.9, 133.3, 138.0 and 144.8.

b. 2-(hex-5-enyl)isoindoline-1,3-dione (32)

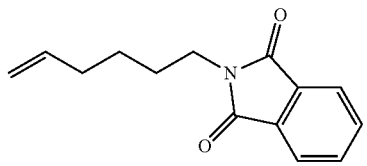 [SMILES: C=CCCCCN1C(=O)c2ccccc2C1=O]

To a solution containing 5.1 g (20 mmol) of tosylate 31 in 40 mL of DMF was added 4.4 g (24 mmol) of potassium phthalimide and the mixture heated at 60° C. for 24 h. The reaction mixture was allowed to cool to room temperature and then the solution was filtered. The filtrate was then washed with brine and extracted with three 30-mL portions of ether. The combined organic layer was washed with brine and dried (MgSO$_4$), then concentrated under diminished pressure to afford 32 as colorless oil. The crude residue was used for the next reaction.

c. N-chlorohex-5-en-1-amine Hydrochloride (33)

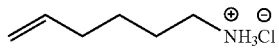

To a solution containing 3.10 g (13.3 mmol) of the crude phthalimide 32 in 16 mL of ethanol was added 400 µL (13.3 mmol) of hydrazine hydrate. The reaction mixture was heated at 60° C. for 12 h. The cooled reaction mixture was treated dropwise with 4.7 mL of conc HCl and then again heated to reflux for an additional 2 h. The cooled reaction mixture was filtered to remove a white precipitate. The filtrate was concentrated under diminished pressure to afford a crude residue. The residue was triturated successively with chloroform and ether to afford amine hydrochloride 33 as a yellow solid: yield 686 mg (25% over two steps); $^1$H NMR (CDCl$_3$) δ 1.50 (quin, 2H, J=15.2 and 7.60 Hz), 1.79 (quin, 2H, J=15.2 and 7.20 Hz), 2.09 (dd, 2H, J=14.4 and 7.20 Hz), 3.00 (br s, 2H), 4.93-5.07 (m, 2H), 5.70-5.85 (m, 1H) and 8.25 (br s, 3H); $^{13}$C NMR (CDCl$_3$) δ 25.8, 27.1, 33.1, 40.0, 115.5 and 137.7.

d. 5-(hex-5-enylamino)-2-hydroxy-3-(undec-10-enyl)cyclohexa-2,5-diene-1,4-dione (37)

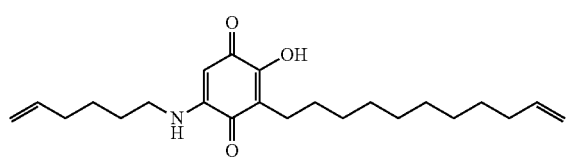

37

To a solution containing 141 mg (1.04 mmol) of amine hydrochloride 33 in 35 mL of ethanol was added 123 mg (96%, 1.04 mmol) of potassium t-butoxide and the reaction mixture was stirred at room temperature for 30 min. To the reaction mixture was added a solution of 107 mg (0.35 mmol) of hydroxyquinone 36 in 35 mL of ethanol dropwise over a period of 15 min. The reaction mixture was stirred for 12 h. The reaction mixture was concentrated under diminished pressure to afford a crude residue. The resulting residue was dissolved in 30 mL of dichloromethane and washed with 10 mL of 1 N HCl. The organic layer was dried (MgSO$_4$) and then concentrated under diminished pressure to afford a crude residue. The residue was applied to a silica gel column (24×2 cm). Elution with 50:1 dichloromethane-methanol gave compound 37 as a bright red solid: yield 126 mg (75%); mp 77-78° C.; silica gel TLC R$_f$ 0.13 (chloroform); $^1$H NMR (CDCl$_3$) δ 1.17-1.38 (m, 12H), 1.39-1.53 (m, 4H), 1.60-1.76 (m, 2H), 2.01 (dd, 2H, J=14.1 and 6.9 Hz), 2.08 (dd, 2H, J=13.6 and 6.8 Hz), 2.32-2.41 (m, 2H), 3.15 (d, 2H, J=4.5 Hz), 4.86-5.07 (m, 4H), 5.33 (s, 1H), 5.68-5.86 (m, 2H), 6.46 (s, 1H) and 8.25 (s, 1H); $^{13}$C NMR (CDCl$_3$) δ 22.7, 26.2, 27.6, 28.2, 29.02, 29.22, 29.53, 29.57, 29.62, 29.67, 33.3, 33.9, 42.8, 91.7, 114.2, 115.4, 115.8, 137.9, 139.3, 149.8, 155.4, 178.8 and 182.6; IR (thin film): 3270, 1640, 1360, 1200 cm$^{-1}$; mass spectrum (APCI), m/z 374.2694 (M+H)$^+$ (C$_{23}$H$_{36}$NO$_3$ requires 374.2695).

Example 23: Preparation of 5-(hex-5-enylamino)-2-methoxy-3-(undec-10-enyl)cyclohexa-2,5-diene-1,4-dione (38)

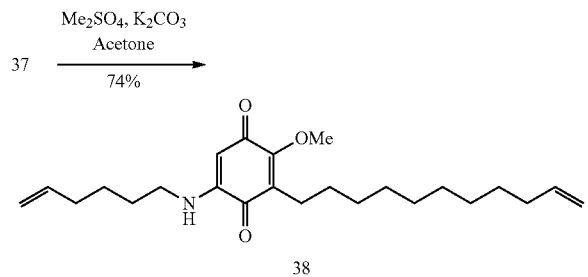

38

To a solution containing 144 mg (0.39 mmol) of quinone 37 and 2.00 g (38.0 mmol) of potassium carbonate in 9.6 mL of anh acetone was added 190 μL (253 mg, 1.93 mmol) of dimethyl sulfate. The reaction mixture was heated to reflux for 3 h and allowed to cool to room temperature with stirring overnight. The solvent was concentrated under diminished pressure to afford a crude product. The crude product was dissolved in 20 mL of dichloromethane and washed with 5 mL of 1 N HCl. The aqueous layer was extracted with three 10-mL portions of dichloromethane. The combined organic layer was dried (MgSO$_4$) and concentrated under diminished pressure to afford a crude residue. The residue was applied to a silica gel column (24×2 cm). Elution with 20% diethyl ether in hexane gave compound 38 as a bright red solid: yield 110 mg (74%); mp 45-46° C.; silica gel TLC R$_f$ 0.36 (dichloromethane); $^1$H NMR (CDCl$_3$) δ 1.18-1.39 (m, 14H), 1.45 (quin, 2H, J=15.2 and 7.6 Hz), 1.63 (quin, 2H, J=14.8 and 7.2 Hz), 1.97-2.11 (m, 4H), 2.34 (t, 2H, J=7.6 Hz), 3.08 (dd, 2H, J=13.2 and 6.0 Hz), 4.09 (s, 3H), 4.86-5.05 (m, 4H), 5.23 (s, 1H) and 5.69-5.87 (m, 3H); $^{13}$C NMR (CDCl$_3$) δ 23.0, 26.3, 27.7, 28.7, 29.0, 29.2, 29.5, 29.6, 29.7, 33.3, 33.9, 42.5, 61.7, 95.8, 114.2, 115.3, 127.4, 138.0, 139.3, 146.8, 158.5, 181.6 and 184.0; IR (thin film): 3330, 1630, 1580, 1210 cm$^{-1}$; mass spectrum (APCI), m/z 388.2858 (M+H)$^+$ (C$_{24}$H$_{38}$NO$_3$ requires 388.2852).

Example 24: Preparation of Cyclic Alkene (39)

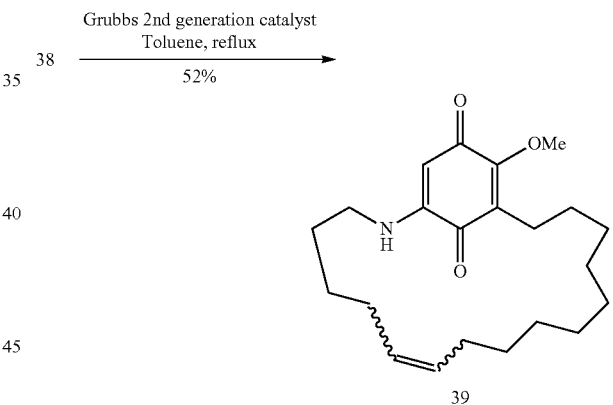

39

To a solution containing 31 mg (80 μmol) of quinone 38 in toluene was added 7.0 mg (8.0 μmol) of Grubb's 2$^{nd}$ generation catalyst. The reaction mixture was heated at 80° C. for 12 h and then allowed to cool to room temperature. The solvent was concentrated under diminished pressure to afford crude residue. The residue was applied to a silica gel column (30×3 cm). Elution with 1:9 ethyl acetate-hexane afforded compound 39 as a purple-red solid (mixture of isomers): yield 15 mg (52%); mp 82-84° C.; silica gel TLC R$_f$ 0.23 (dichloromethane); major isomer $^1$H NMR (CDCl$_3$) δ 1.08-1.35 (m, 12H), 1.35-1.53 (m, 4H), 1.57-1.70 (m, 2H), 1.92-2.04 (m, 4H), 2.42-2.52 (m, 2H), 3.08-3.21 (m, 3H), 4.08-4.14 (m, 2H), 5.24-5.31 (m, 2H), 5.31-5.43 (m, 1H) and 5.82-5.92 (m, 1H); mixture of isomers $^{13}$C NMR (CDCl$_3$) δ 22.2, 26.6, 26.85, 26.97, 26.98, 27.11, 27.15, 27.2, 27.38, 27.44, 27.7, 28.2, 28.3, 28.4, 28.5, 28.6, 28.8, 28.9, 29.1, 29.3, 29.8, 30.0, 31.6, 32.3, 42.1, 53.6, 61.7, 62.9, 95.7, 95.9, 127.5, 128.6, 129.5, 131.5, 132.3, 147.0, 158.8, 158.9, 181.6 and 184.2; IR (thin film): 3340, 1640, 1580, 1210 cm$^{-1}$; mass spectrum (APCI), m/z 360.2546 (M+H)$^+$ (C$_{22}$H$_{34}$NO$_3$ requires 360.2539).

Example 25: Preparation of Cyclic Compound (40)

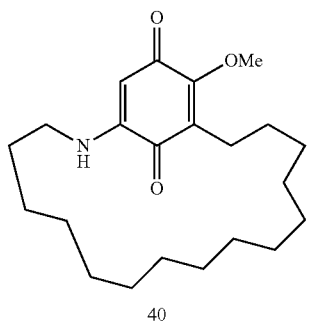

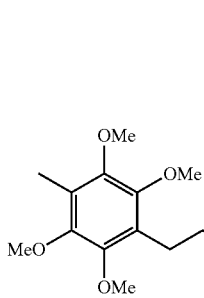

To a solution containing 15.5 mg (0.04 mmol) of quinone 39 in 5 mL of ethyl acetate was added 23 mg of 10% Pd/C and H$_2$ gas was bubbled through the solution at room temperature for 4 h. The reaction mixture was then diluted with 1 mL of methanol and stirred at room temperature overnight. The reaction mixture was purged by bubbling air and then concentrated under diminished pressure to afford a crude residue. The residue was applied to a silica gel column (20×3 cm). Step gradient elution with dichloromethane→100:1 dichloromethane-methanol afforded compound 40 as a purple-red solid: yield 6 mg (38% over two steps); mp 104-105° C.; silica gel TLC R$_f$ 0.3 (dichloromethane); $^1$H NMR (CDCl$_3$) δ 1.06-1.39 (m, 22H), 1.43-1.53 (m, 2H), 1.60-1.69 (m, 2H), 2.43-2.53 (m, 2H), 3.12-3.22 (m, 2H), 4.12 (s, 3H), 5.28 (s, 1H) and 5.89 (s, 1H); $^{13}$C NMR (CDCl$_3$) δ 22.2, 26.3, 27.4, 27.69, 27.75, 27.81, 27.87, 28.0, 28.2, 28.49, 28.53, 28.55, 28.63, 29.1, 42.2, 61.8, 95.8, 127.3, 146.9, 158.9, 181.6 and 184.1; IR (thin film): 3340, 1640, 1630, 1210 cm$^{-1}$; mass spectrum (APCI), m/z 362.2702 (M+H)$^+$ (C$_{22}$H$_{36}$NO$_3$ requires 362.2695).

Example 26: Preparation of 2,5-dimethoxy-3-methyl-6-tridecylcyclohexa-2,5-diene-1,4-dione (42)

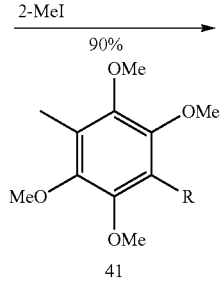

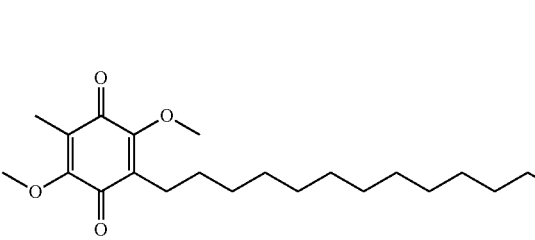

a. 1,2,4,5-tetramethoxy-3-methyl-6-tridecylbenzene (41)

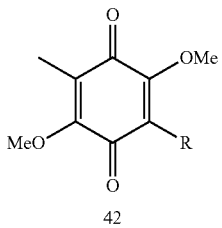

To a solution containing 1.0 g (5.0 mmol) of 1,2,4,5-tetramethoxy-3-tridecylbenzene 3 and 75 µL (0.50 mmol) tetramethylethylenediamine in 25 mL dry THF was added 2.7 mL (2.5 M in Hexanes, 7.4 mmol) of n-butyllithium dropwise at −78° C. over 5 min. The reaction mixture is warmed to 0° C. over 2 h, 0.5 mL (7.5 mmol) of purified methyliodide added and the reaction mixture stirred at room temperature under an atmosphere of argon for 15 h. The reaction mixture was quenched with 20 mL of saturated NH$_4$Cl and extracted with five 10 mL portions of diethyl ether. The organic layer was washed with distilled water, brine and dried (MgSO$_4$). The excess solvent was concentrated under diminished pressure to afford a crude residue. The crude residue was applied to a silica gel column (6×3 cm). Elution with 1:9 ethyl acetate-hexanes afforded 3 as a colorless solid: yield 0.98 g (90%); silica gel TLC R$_f$ 0.55 (1:1 ethyl ether-hexanes); unreacted 1,2,4,5-tetramethoxy-3-tridecylbenzene (3) was recovered; $^1$H NMR (CDCl$_3$) δ 0.87 (3H, t, J=6.8 Hz), 1.25-1.29 (20H, m), 1.47-1.58 (2H, m), 2.14 (3H, s) 2.61 (2H, dd, J=8.8 and 6.9 Hz), 3.74 (6H, s), 3.80 (6H, s); $^{13}$C NMR (CDCl$_3$) δ 9.02, 14.1, 22.7, 24.6, 29.3, 29.5, 29.6, 29.6, 29.7, 29.7, 30.0, 30.7, 32.0, 56.1, 60.8, 60.9, 96.7, 131.1, 141.1 and 148.8.

b. 2,5-dimethoxy-3-methyl-6-tridecylcyclohexa-2,5-diene-1,4-dione (42)

To a solution containing 0.10 g (0.27 mmol) of 1,2,4,5-tetramethoxy-3-methyl-6-tridecylbenzene 41 in 2.6 mL of acetonitrile was added 2.6 mL (0.28 g, 0.52 mmol) of 7 (1.82 mL):3 (0.78 mL) solution of cerium (IV) ammonium nitrate in acetonitrile:water dropwise at −7° C. (salt-ice bath) over 30 min. The reaction was allowed to stir at room temperature for 3 h and diluted with 10 mL of diethylether. The organic layer was washed with distilled water, brine and dried (MgSO$_4$). The excess solvent was concentrated under reduced pressure to afford a crude of quinone 42. The crude residue was applied to a silica gel column (7×2 cm). Elution with 1:4 ethyl acetate-hexanes gave 42 as a yellow-orange solid: yield 55 mg (60%); silica gel TLC R$_f$ 0.68 (1:4 ethyl acetate-hexanes); $^1$H NMR (CDCl$_3$) δ 0.82 (3H, t, J=6.8 Hz), 1.20-1.25 (20H, m), 1.32-1.41 (2H, m), 1.84 (3H, s), 2.33 (2H, t, J=8 Hz), 3.93 (6H, s); $^{13}$C NMR (CDCl$_3$) δ 9.02, 14.0, 22.7, 23.0, 24.5, 28.9, 29.3, 29.4, 29.4, 29.5, 29.6, 29.6, 29.6, 31.1, 31.8, 60.1, 126.3, 130.9, 147.4, 155.4, 184.0 and 184.5. mass spectrum (APCI+), m/z 365.2692 (M+H)$^+$ (C$_{22}$H$_{37}$O$_4$ requires m/z 478.3532).

Examples 27 and 28: Preparation of tert-butyl 4-(4-methoxy-2-methyl-3,6-dioxo-5-tridecylcyclohexa-1,4-dienylamino)butanoate (43) and 2,5-bis(tert-butyl 4-aminobutanoate)-3-methyl-6-tridecylcyclohexa-2,5-diene-1,4-dione (44)

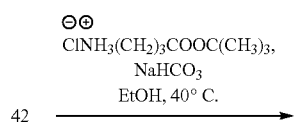

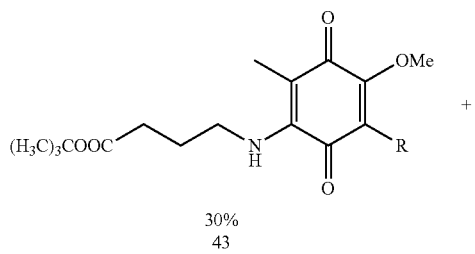

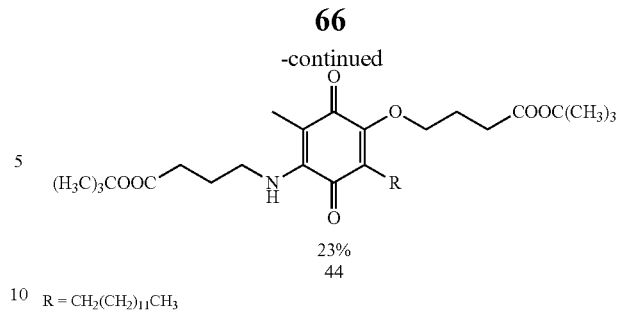

$R = CH_2(CH_2)_{11}CH_3$

To a solution of 52 mg (0.142 mmol) of 2,5-dimethoxy-3-methyl-6-tridecylcyclohexa-2,5-diene-1,4-dione 42 and 1.0 g (13 mmol) of sodium bicarbonate in 9.7 mL of ethanol was added 14 mg (0.071 mmol) of γ-aminobutyric acid tert-butyl ester hydrochloride salt. The reaction mixture was stirred for 27 h at 45° C. at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 43 and 44 as a bright red amorphous solids: yield—21 mg (43) 30%, (44) 23%; silica gel TLC R$_f$ 0.63 (43) and 0.32 (44) (1:2 ethyl acetate-hexanes); $^1$H NMR (CDCl$_3$) (43) δ 0.87 (3H, t, J=6.8 Hz), 1.25-1.36 (22H, m), 1.45 (9H, s), 1.85-1.89 (2H, quin, J=9 Hz), 2.03 (3H, s), 2.32 (2H, q, J=6.8 Hz), 2.35-2.39 (2H, m), 3.14 (2H, dd, J=13.0 and 6.8 Hz), 4.10 (3H, s), 5.94 (1H, m); $^{13}$C NMR (CDCl$_3$) (43) δ 10.3, 14.3, 22.8, 23.1, 23.6, 28.2, 28.8, 29.5, 29.6, 29.7, 29.81, 29.83, 32.1, 32.9, 42.1, 61.8, 81.1, 96.1, 127.6, 146.9, 158.5, 172.2, 181.8 and 183.9; mass spectrum (APCI), m/z 492.3692 (M+H)$^+$ (C$_{29}$H$_{50}$NO$_5$ requires m/z 492.3692).

$^1$H NMR (CDCl$_3$) (44) δ 0.87 (3H, t, J=6.8 Hz), 1.25-1.36 (22H, m), 1.43 (18H, s), 1.86-1.91 (4H, m), 2.03 (3H, s), 2.32 (4H, m), 2.42 (2H, t, 6.8), 3.47 (2H, t, J=5.6), 3.55 (2H, t, J=6), 5.94 (2H, m); $^{13}$C NMR (CDCl$_3$) (44) 10.3, 14.1, 22.7, 24.2, 25.8, 26.1, 28.1, 29.4, 29.6, 29.7, 29.7, 30.7, 31.9, 32.48, 43.8, 44.1, 80.7, 80.7, 101.44, 106.78, 146.16, 147.1, 171.9, 171.9, 180.2, 180.6; mass spectrum (APCI), m/z 619.4691 (M+H)$^+$ (C$_{36}$H$_{63}$N$_2$O$_6$ requires m/z 619.4691).

Examples 29 and 30: Preparation of Butyl 4-(4-methoxy-2-methyl-3,6-dioxo-5-tridecylcyclohexa-1,4-dienylamino)butanoate (46) and 2,5-bis(butyl 4-aminobutanoate)-3-methyl-6-tridecylcyclohexa-2,5-diene-1,4-dione (47)

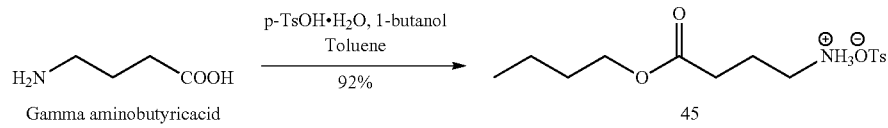

Gamma aminobutyricacid

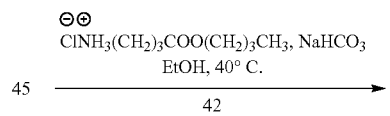

-continued

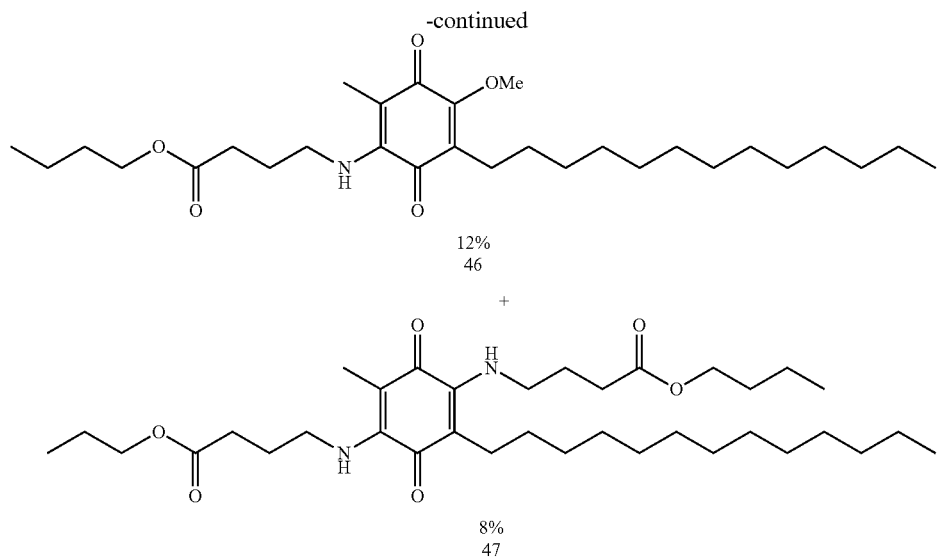

12%
46

+

8%
47 a. Tosylate Salt (45)

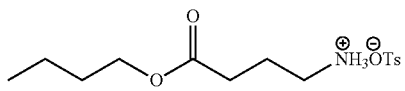

A solution of 1.00 g (9.70 mmol) of 4-aminobutanoic acid, 2.02 g (1.08 mmol) p-toluenesulfonic acid monohydrate and 1.1 mL (1.24 mmol) of 1-butanol in 20 mL of toluene was heated under reflux, using a Dean and Stark distilling receiver, for 24 h. The reaction mixture was cooled to room temperature and diluted with 20 mL of anhydrous diethyl ether to afford p-toluenesulfonate 13 as a crystalline white solid: yield 2.96 g (92%); silica gel TLC $R_f$ 0.25 (9:1 chloroform-methanol); $^1$H NMR (CD$_3$OD) δ 0.94 (t, 3H, J=7.4 Hz), 1.33-1.46 (m, 2H), 1.55-1.67 (m, 2H), 1.92 (dt, 2H, J=20.0 and 7.3 Hz), 2.37 (s, 3H), 2.44 (t, J=7.2 Hz, 2H), 2.92-3.02 (m, 2H), 4.09 (t, 2H, J=6.6 Hz), 4.86 (s, 3H), 7.24 (d, 2H, J=10.5 Hz), 7.71 (d, 2H, J=10 Hz); $^{13}$C NMR (CD$_3$OD) δ 14.0, 20.1, 21.4, 23.7, 31.6, 31.8, 40.1, 65.6, 126.8, 129.5, 141.6, 143.3 and 174.1.

b. Butyl 4-(4-methoxy-2-methyl-3,6-dioxo-5-tridecylcyclohexa-1,4-dienylamino)butanoate (46) and 2,5-bis(Butyl 4-aminobutanoate)-3-methyl-6-tridecylcyclohexa-2,5-diene-1,4-dione (47)

To a solution of 150 mg (0.412 mmol) of 2,5-dimethoxy-3-methyl-6-tridecylcyclohexa-2,5-diene-1,4-dione 42 and 1.0 g (13 mmol) of sodium bicarbonate in 9.7 mL of ethanol was added 40 mg (0.253 mmol) of γ-aminobutyric acid butyl ester hydrochloride salt. The reaction mixture was stirred for 27 h at 45° C. at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 46 and 47 as a bright red amorphous solids: yield—21 mg (46) 12%, (47) 8%; silica gel TLC $R_f$ 0.69 (46) and 0.36 (47) (1:2 ethyl acetate-hexanes); $^1$H NMR (CDCl$_3$) (46) δ 0.87 (t, 3H, J=6.8 Hz), 0.93 (t, 3H, J=7.5 Hz), 1.16-1.46 (m, 23H), 1.59-1.61 (m, 3H), 1.91 (t, 2H, J=7.5 Hz), 2.03 (3H, s), 2.32-2.40 (m, 4H), 3.51 (t, 2H, J=7.0 Hz), 4.04 (3H, s), 4.07-4.09 (m, 2H), 5.95 (t, 1H, J=5.6 Hz); $^{13}$C NMR (CDCl$_3$) (46) δ 10.0, 13.69, 14.1, 19.1, 22.7, 22.9, 26.0, 28.7, 29.4, 29.4, 29.6, 29.7, 29.7, 30.6, 31.3, 31.9, 44.4, 61.5, 64.6, 106.3, 127.1, 143.9, 157.9, 172.8, 172.8, 182.35, 184.9; mass spectrum (APCI), m/z 492.3689 (M+H)$^+$ (C$_{29}$H$_{50}$NO$_5$ requires 492.3689).

$^1$H NMR (CDCl$_3$) (47) δ 0.87 (t, 3H, J=6.8 Hz), 0.93 (t, 6H, J=7.5 Hz), 1.16-1.46 (m, 20H), 1.35-1.39 (2H, q, J=8 Hz), 1.59-1.62 (m, 6H), 1.93-1.95 (4H, m), 2.03 (3H, s), 2.38-2.41 (m, 8H), 3.51 (m, 4H), 4.07-4.10 (m, 4H), 6.58 (m, 2H); $^{13}$C NMR (CDCl$_3$) (47) 10.3, 13.6, 14.1, 19.1, 22.7, 24.2, 25.8, 26.1, 29.4, 29.6, 29.7, 29.7, 30.6, 30.7, 31.3, 31.3, 31.9, 43.8, 44.1, 64.6, 64.6, 101.6, 106.9, 146.07, 147.0, 172.6, 171.7, 180.2, 180.7; mass spectrum (APCI), m/z 619.4690 (M+H)$^+$ (C$_{36}$H$_{63}$N$_2$O$_6$ requires m/z 619.4690).

Examples 31 and 32: Preparation of Hexyl 4-(4-methoxy-2-methyl-3,6-dioxo-5-tridecylcyclohexa-1,4-dienylamino)butanoate (49) and 2,5-bis(hexyl 4-aminobutanoate)-3-methyl-6-tridecylcyclohexa-2,5-diene-1,4-dione (50)

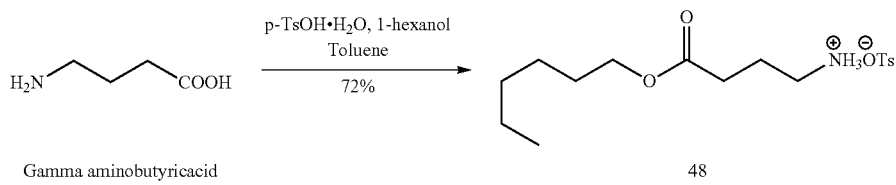

Gamma aminobutyricacid

48

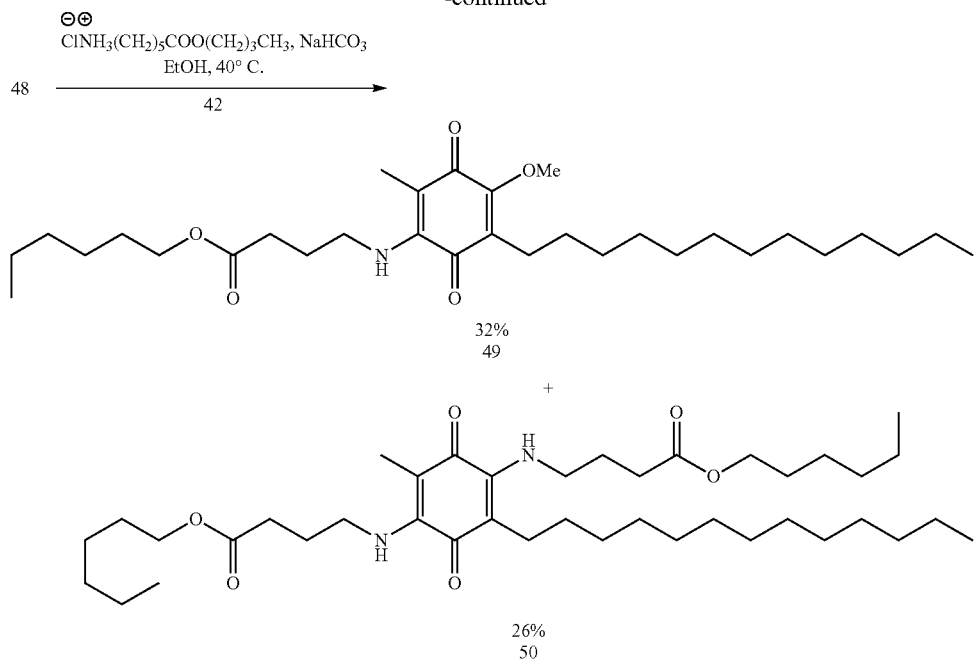

a. Tosylate Salt (48)

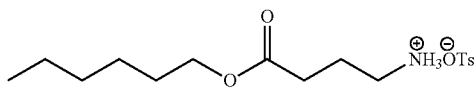

A solution of 1.00 g (9.70 mmol) of 4-aminobutanoic acid, 2.02 g (1.08 mmol) p-toluenesulfonic acid monohydrate and 1.51 mL (1.24 mmol) of 1-hexanol in 20 mL of toluene was heated under reflux, using a Dean and Stark distilling receiver, for 24 h. The reaction mixture was cooled to room temperature and diluted with 20 mL of anhydrous diethyl ether to afford p-toluenesulfonate 48 as a crystalline white solid: yield 2.50 g (72%); silica gel TLC $R_f$ 0.22 (9:1 chloroform-methanol); $^1$H NMR (CDCl$_3$) δ 0.88 (t, J=7.2 Hz, 3H), 1.21-1.35 (m, 6H), 1.55 (quin, 2H, J=14.0 and 7.2 Hz), 1.85 (quin, 2H, J=14.8 and 7.30 Hz), 2.27 (t, 2H, J=7.34 Hz), 2.36 (s, 3H), 2.80-2.92 (m, 2H), 3.98 (t, 2H, J=6.9 Hz), 7.18 (d, 2H, J=7.9 Hz), 7.72-7.83 (m, 5H); $^{13}$C NMR (CDCl$_3$) δ 14.2, 21.5, 22.67, 22.71, 25.7, 28.6, 31.0, 31.6, 39.4, 65.0, 126.1, 129.2, 140.9, 141.2 and 172.6.

b. Hexyl 4-(4-methoxy-2-methyl-3,6-dioxo-5-tridecylcyclohexa-1,4-dienylamino)butanoate (49) and 2,5-bis(Hexyl 4-aminobutanoate)-3-methyl-6-tridecylcyclohexa-2,5-diene-1,4-dione (50)

To a solution of 44 mg (0.12 mmol) of 2,5-dimethoxy-3-methyl-6-tridecylcyclohexa-2,5-diene-1,4-dione 42 and 1.0 g (13 mmol) of sodium bicarbonate in 9.7 mL of ethanol was added 5.6 mg (0.06 mmol) of γ-aminobutyric acid hexyl ester hydrochloride salt 48. The reaction mixture was stirred for 27 h at 45° C. at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 49 and 50 as a bright red amorphous solids: yield—(49) 32%, (50) 26%; silica gel TLC $R_f$ 0.75 (46) and 0.42 (47) (1:2 ethyl acetate-hexanes); $^1$H NMR (CDCl$_3$) (49) δ 0.85-0.89 (m, 6H), 1.20-1.32 (m, 28H), 1.55-1.63 (m, 2H), 1.96 (m, 2H), 2.02 (3H, s), 2.25-2.33 (t, 2H, J=8 Hz), 2.36-2.39 (t, 2H, J=9.5 Hz) 3.50 (q, 2H, J=6.5 Hz), 4.02-4.21 (m, 2H), 4.03 (3H, s), 5.87-6.06 (m, 1H); $^{13}$C NMR (CDCl$_3$) δ 10.0, 13.9, 14.1, 14.2, 21.0, 22.5, 22.7, 23.0, 25.6, 26.5, 28.7, 29.3, 29.4, 29.5, 29.7, 29.7, 31.3, 31.4, 31.9, 44.4, 60.4, 61.7, 64.9, 106.3, 127.1, 143.8, 157.8, 171.1, 172.8, 182.3 and 184.9; mass spectrum (APCI), m/z 520.4002 (M+H)$^+$ (C$_{31}$H$_{54}$NO$_5$ requires 520.4002).

$^1$H NMR (CDCl$_3$) (50) δ 0.85-0.90 (m, 12H), 1.20-1.32 (m, 28H), 1.59-1.62 (m, 4H), 1.96 (m, 4H), 2.02 (3H, s), 2.37-2.42 (m, 8H), 3.47 (t, 3H, J=9 Hz), 3.57 (t, 2H, J=9 Hz), 4.02-4.21 (m, 4H), 5.87-6.06 (m, 2H); $^{13}$C NMR (CDCl$_3$) (50) 10.3, 14.0, 14.1, 19.8, 22.5, 22.7, 24.1, 25.5, 25.728.5, 29.3, 29.6, 29.6, 29.6, 30.6, 31.3, 31.3, 31.3, 31.9, 43.8, 44.0, 53.3, 64.6, 101.5, 104.9, 106.9, 146.02, 147.0, 172.6, 172.6, 180.2, 180.6; mass spectrum (APCI), m/z 675.5308 (M+H)$^+$ (C$_{40}$H$_{71}$N$_2$O$_6$ requires m/z 675.5308).

Example 33: Preparation of 3-hexadecyl-2,5-dimethoxycyclohexa-2,5-diene-1,4-dione (52)

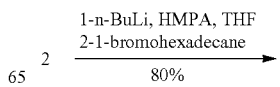

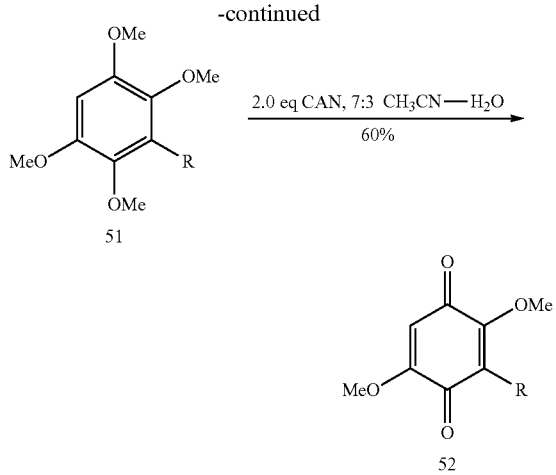

a. 3-hexadecyl-1,2,4,5-tetramethoxybenzene (51)

To a solution containing 300 mg (1.5 mmol) of 1,2,4,5-tetramethoxybenzene 2 and 29 μL (0.20 mmol) tetramethylethylenediamine in 5 mL dry THF was added 1 mL (2.5 M in Hexanes, 2.66 mmol) of n-butyllithium dropwise at −78° C. over 5 min. The reaction mixture is warmed to 0° C. over 2 h, 500 μL (1.9 mmol) of purified 1-bromotridecane added and the reaction mixture stirred at room temperature under an atmosphere of argon for 15 h. The reaction mixture was quenched with 20 mL of saturated $NH_4Cl$ and extracted with five 10 mL portions of diethyl ether. The organic layer was washed with distilled water, brine and dried ($MgSO_4$). The excess solvent was concentrated under diminished pressure to afford a crude residue. The crude residue was applied to a silica gel column (6×3 cm). Elution with 1:9 ethyl acetate-hexanes afforded 51 as a colorless solid: yield 80%; silica gel TLC $R_f$ 0.40 (1:1 ethyl ether-hexanes); unreacted 1,2,4,5-tetramethoxybenzene (2) was recovered; $^1H$ NMR ($CDCl_3$) δ 0.88 (3H, t, J=7.2 Hz), 1.25-1.37 (26H, m), 1.50-1.52 (2H, m), 2.61 (2H, t, J=8 Hz), 3.77 (6H, s), 3.84 (6H, s), 6.41 (1H, s); $^{13}C$ NMR ($CDCl_3$) δ 14.3, 22.8, 24.7, 24.8, 29.5, 29.6, 29.8, 29.8, 30.2, 30.3, 30.9, 31.3, 32.1, 56.4, 60.7, 61.1, 96.8, 131.3, 141.3 and 149.0. mass spectrum (APCI), m/z 423.3474 (M+H)+ ($C_{26}H_{47}O_4$ requires m/z 423.3474).

b. 3-hexadecyl-2,5-dimethoxycyclohexa-2,5-diene-1,4-dione (52)

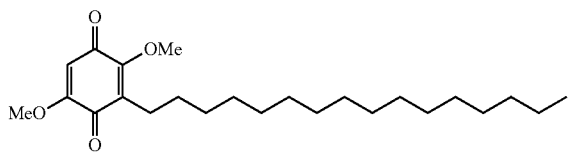

To a solution containing 0.10 g (0.23 mmol) of 3-hexadecyl-1,2,4,5-tetramethoxybenzene 51 in 2.6 mL of acetonitrile was added 2.6 mL (0.28 g, 0.52 mmol) of 7 (1.82 mL):3 (0.78 mL) solution of cerium (IV) ammonium nitrate in acetonitrile:water dropwise at −7° C. (salt-ice bath) over 30 min. The reaction was allowed to stir at room temperature for 3 h and diluted with 10 mL of diethylether. The organic layer was washed with distilled water, brine and dried ($MgSO_4$). The excess solvent was concentrated under reduced pressure to afford a crude of quinone 52. The crude residue was applied to a silica gel column (7×2 cm). Elution with 1:4 ethyl acetate-hexanes gave 52 as a yellow-orange solid: yield 60 mg (65%); silica gel TLC $R_f$ 0.68 (1:4 ethyl acetate-hexanes); $^1H$ NMR ($CDCl_3$) δ 0.88 (3H, t, J=7.2 Hz), 1.25-1.32 (26H, m), 1.38-1.42 (2H, m), 2.43 (2H, t, J=8 Hz), 3.81 (3H, s), 4.05 (3H, s), 5.73 (1H, s); $^{13}C$ NMR ($CDCl_3$) δ 14.1, 22.7, 23.1, 28.6, 29.3, 29.4, 29.5, 29.6, 29.7, 31.2, 31.9, 38.1, 56.3 61.3, 105.4, 130.7, 155.9, 158.7, 182.4 and 183.6. mass spectrum (MALDI), m/z 393.48 (M+H)+ ($C_{24}H_{41}O_4$ requires m/z 393.48).

Example 34: Preparation of 3-hexadecyl-2,5-bis(tert-butyl 4-aminobutanoate)-2,5-diene-1,4-dione (54)

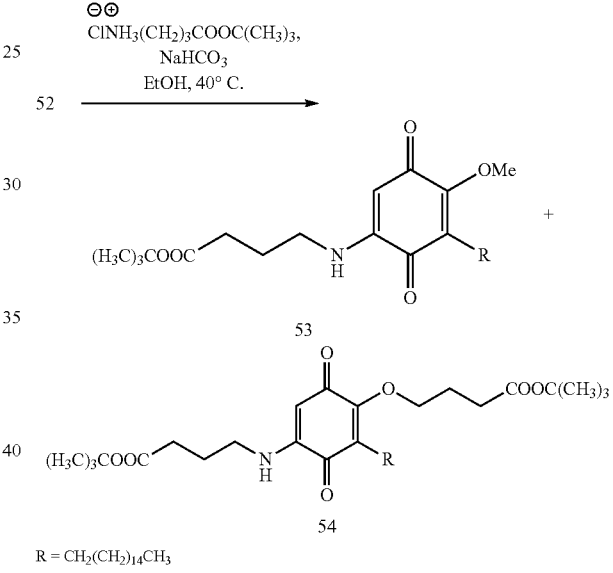

R = $CH_2(CH_2)_{14}CH_3$

To a solution of 25 mg (0.068 mmol) of 3-hexadecyl-2,5-dimethoxycyclohexa-2,5-diene-1,4-dione 52 and 1.0 g (13 mmol) of sodium bicarbonate in 9.7 mL of ethanol was added 12.3 mg (0.063 mmol) of γ-aminobutyric acid tert-butyl ester hydrochloride salt. The reaction mixture was stirred for 27 hours at room temperature. The reaction mixture was then diluted with 5 mL of water and extracted with seven 2 mL portions of dichloromethane. The organic layer was washed with water, brine and dried ($Na_2SO_4$). The excess solvent was concentrated under diminished pressure to afford a crude residue. The residue was purified by flash column chromatography on a silica gel column (24×2 cm). Elution with 1:5 ethyl acetate-hexane gave 54 as a bright red amorphous solids: yield—12 mg (54) 30%; silica gel TLC $R_f$ 0.35 (1:2 ethyl acetate-hexanes); $^1H$ NMR ($CDCl_3$) (54) δ 0.87 (3H, t, J=7.2 Hz), 1.24-1.37 (28H, m), 1.44 (18H, s), 1.87-1.94 (4H, m), 2.32 (4H, q, J=7.6 Hz), 2.46 (2H, t, J=8.8 Hz), 3.17 (2H, q, J=6.4 Hz), 3.52 (2H, q, J=6.4 Hz), 5.25 (1H, s), 6.60-6.65 (2H, m); $^{13}C$ NMR ($CDCl_3$) (54) δ14.1, 22.7, 23.6, 24.1, 25.8, 28.1, 29.3, 29.6, 29.6, 29.7, 30.6, 31.9, 32.5, 32.6, 32.8, 41.8, 43.8, 80.7, 80.8, 92.1, 107.8, 146.6, 150.5, 171.8, 171.9, 179.0, 179.5; mass spectrum (APCI), m/z 647.4999 (M+H)$^+$ (C$_{38}$H$_{67}$N$_2$O$_6$ requires m/z 647.4999).

It is noted that compound 53 is also a compound of the invention.

Example 35: Preparation of 3-hexadecyl-2,5-bis (butyl 4-aminobutanoate)-2,5-diene-1,4-dione (56)

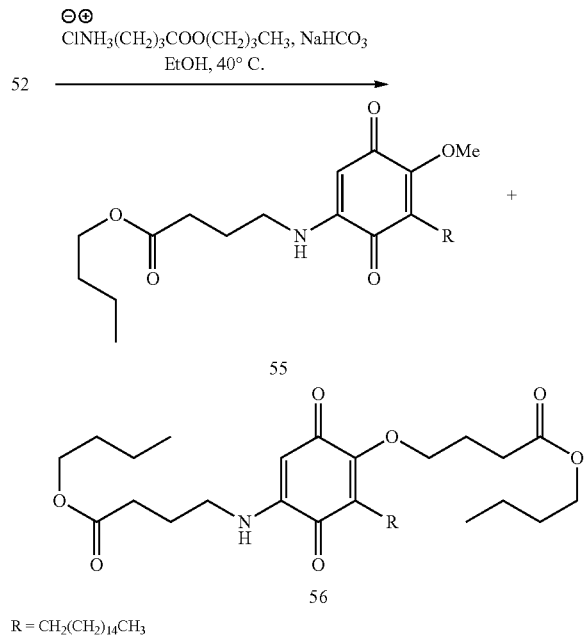

R = CH$_2$(CH$_2$)$_{14}$CH$_3$

To a solution of 25 mg (0.063 mmol) of 3-hexadecyl-2,5-dimethoxycyclohexa-2,5-diene-1,4-dione 52 and 1.0 g (13 mmol) of sodium bicarbonate in 9.7 mL of ethanol was added 12.2 mg (0.063 mmol) of γ-aminobutyric acid n-butyl ester hydrochloride salt. The reaction mixture was stirred for 27 h at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 56 as a bright red amorphous solids: yield—15 mg (56) 37%; silica gel TLC R$_f$ 0.30 (1:2 ethyl acetate-hexanes); $^1$H NMR (CDCl$_3$) δ 0.87 (3H, t, J=7.2 Hz), 0.93 (6H, t, J=7.6 Hz), 1.25-1.32 (26H, m), 1.38 (2H, q, J=7.2 Hz), 1.56 (4H, m), 1.61 (4H, t, J=7.2 Hz), 1.97 (4H, m), 2.40 (4H, q, J=9.6 Hz), 2.44 (2H, t, J=8.8 Hz), 3.18 (2H, q, J=6.4 Hz), 3.52 (2H, q, J=6.4 Hz), 4.09 (4H, t, J=6.8 Hz) 5.25 (1H, s), 6.60-6.65 (2H, m); $^{13}$C NMR (CDCl$_3$) 13.7, 14.1, 19.1, 22.7, 23.5, 24.1, 25.7, 29.3, 29.6, 29.6, 29.7, 30.6, 30.6, 30.6, 31.3, 31.5, 31.9, 41.8, 43.8, 64.6, 64.6, 92.21, 107.9, 146.5, 150.4, 172.6, 172.7, 179.1 and 179.6; mass spectrum (APCI), m/z 647.49999 (M+H)$^+$ (C$_{38}$H$_{67}$N$_2$O$_6$ requires m/z 647.4999).

It is noted that compound 55 is also a compound of the invention.

Example 36: Preparation of 3-hexadecyl-2,5-bis (hexyl 4-aminobutanoate)-2,5-diene-1,4-dione (58)

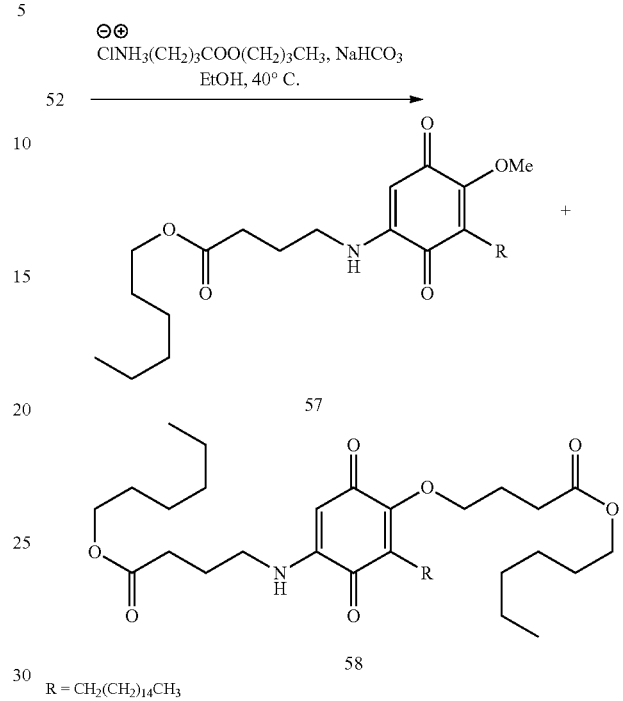

R = CH$_2$(CH$_2$)$_{14}$CH$_3$

To a solution of 25 mg (0.063 mmol) of 3-hexadecyl-2,5-dimethoxycyclohexa-2,5-diene-1,4-dione 52 and 1.0 g (13 mmol) of sodium bicarbonate in 9.7 mL of ethanol was added 14.1 mg (0.063 mmol) of γ-aminobutyric acid n-hexyl ester hydrochloride salt. The reaction mixture was stirred for 27 h at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 58 as a bright red amorphous solids: yield—10 mg (58) 22%; silica gel TLC R$_f$ 0.30 (1:2 ethyl acetate-hexanes); $^1$H NMR (CDCl$_3$) δ 0.87 (9H, m), 1.25-1.38 (36H, m), 1.61 (4H, m), 1.97 (4H, m), 2.40 (8H, q, J=9.6 Hz), 2.46 (2H, t, J=8.8 Hz), 3.18 (2H, q, J=6.4 Hz), 3.52 (2H, q, J=6.4 Hz), 4.07 (4H, t, J=6.8 Hz) 5.25 (1H, s), 6.60-6.65 (2H, m); $^{13}$C NMR (CDCl$_3$) 13.7, 14.1, 19.1, 22.7, 23.5, 24.1, 25.7, 29.3, 29.6, 29.6, 29.7, 30.6, 30.6, 30.6, 31.3, 31.5, 31.9, 41.8, 43.8, 64.6, 64.6, 92.21, 107.9, 146.5, 150.4, 172.6, 172.7, 179.1 and 179.6; mass spectrum (APCI), m/z 703.5625 (M+H)$^+$ (C$_{42}$H$_{75}$N$_2$O$_6$ requires m/z 703.5625).

It is noted that compound 57 is also a compound of the invention.

Example 37: Preparation of 2-hexadecyl-3,6-dimethoxy-5-methylcyclohexa-2,5-diene-1,4-dione (60)

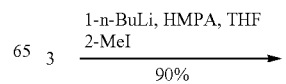

b. 2-hexadecyl-3,6-dimethoxy-5-methylcyclohexa-2,5-diene-1,4-dione (60)

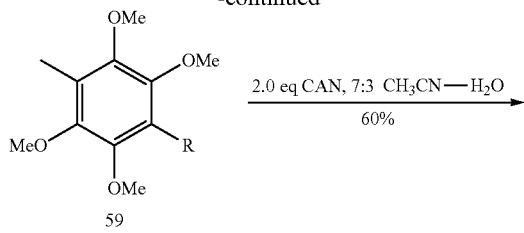

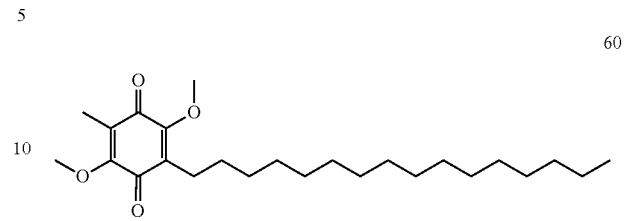

60

To a solution containing 0.10 g (0.23 mmol) of 3-hexadecyl-1,2,4,5-tetramethoxybenzene 59 in 2.6 mL of acetonitrile was added 2.6 mL (0.28 g, 0.52 mmol) of 7 (1.82 mL):3 (0.78 mL) solution of cerium (IV) ammonium nitrate in acetonitrile:water dropwise at −7° C. (salt-ice bath) over 30 min. The reaction was allowed to stir at room temperature for 3 h and diluted with 10 mL of diethylether. The organic layer was washed with distilled water, brine and dried (MgSO$_4$). The excess solvent was concentrated under reduced pressure to afford a crude of quinone 60. The crude residue was applied to a silica gel column (7×2 cm). Elution with 1:4 ethyl acetate-hexanes gave 60 as a yellow-orange solid: yield 55 mg (60%); silica gel TLC R$_f$ 0.72 (1:4 ethyl acetate-hexanes); $^1$H NMR (CDCl$_3$) δ 0.88 (3H, t, J=7.2 Hz), 1.24-1.28 (26H, m), 1.38-1.42 (2H, m), 1.90 (3H, s), 2.43 (2H, t, J=8 Hz), 3.97 (6H, s); $^{13}$C NMR (CDCl$_3$) δ 8.4, 14.1, 22.7, 23.0, 28.9, 29.3, 29.4, 29.5, 29.5, 29.6, 29.6, 29.7, 29.7, 31.9, 61.0, 61.1, 126.4, 130.9, 155.4, 184.0 and 184.5. mass spectrum (MALDI), m/z 407.31 (M+H)$^+$ (C$_{25}$H$_{43}$O$_4$ requires m/z 407.31).

Example 38: Preparation of 2-hexadecyl-3,6-bis-(tert-butyl 4-aminobutanoate)-5-methylcyclohexa-2,5-diene-1,4-dione. (62)

a.
1-hexadecyl-2,3,5,6-tetramethoxy-4-methylbenzene (59)

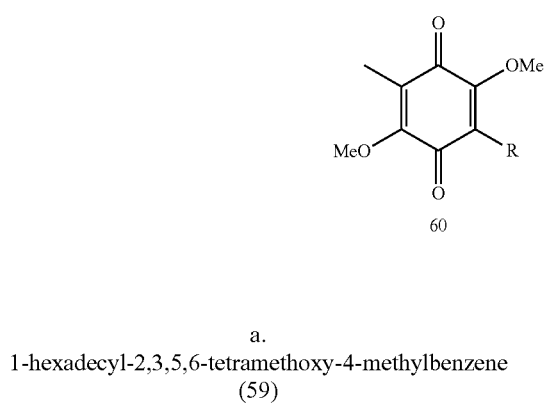

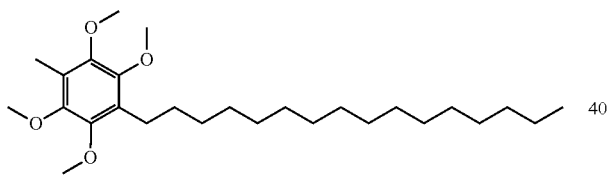

To a solution containing 0.3 g (1.6 mmol) of 1,2,4,5-tetramethoxy-3-tridecylbenzene 3 and 30 μL (0.2 mmol) tetramethylethylenediamine in 8 mL dry THF was added 1 mL (2.5 M in Hexanes, 3.0 mmol) of n-butyllithium dropwise at −78° C. over 5 min. The reaction mixture is warmed to 0° C. over 2 h, 1 mL (15 mmol) of purified methyliodide added and the reaction mixture stirred at room temperature under an atmosphere of argon for 15 h. The reaction mixture was quenched with 20 mL of saturated NH$_4$Cl and extracted with five 10 mL portions of diethyl ether. The organic layer was washed with distilled water, brine and dried (MgSO$_4$). The excess solvent was concentrated under diminished pressure to afford a crude residue. The crude residue was applied to a silica gel column (6×3 cm). Elution with 1:9 ethyl acetate-hexanes afforded 59 as a colorless solid: yield 0.15 g (48%); silica gel TLC R$_f$ 0.65 (1:1 ethyl ether-hexanes); unreacted 1,2,4,5-tetramethoxy-3-tridecylbenzene (3) was recovered; $^1$H NMR (CDCl$_3$) δ 0.87 (3H, t, J=6.8 Hz), 1.24-1.28 (26H, m), 1.47-1.58 (2H, m), 2.14 (3H, s) 2.61 (2H, dd, J=8.8 and 6.9 Hz), 3.76 (6H, s), 3.80 (6H, s); $^{13}$C NMR (CDCl$_3$) δ 9.02, 14.1, 22.7, 24.5, 29.3, 29.5, 29.6, 29.6, 29.7, 30.1, 31.1, 31.9, 60.1, 60.6, 122.9, 127.8, 147.5.

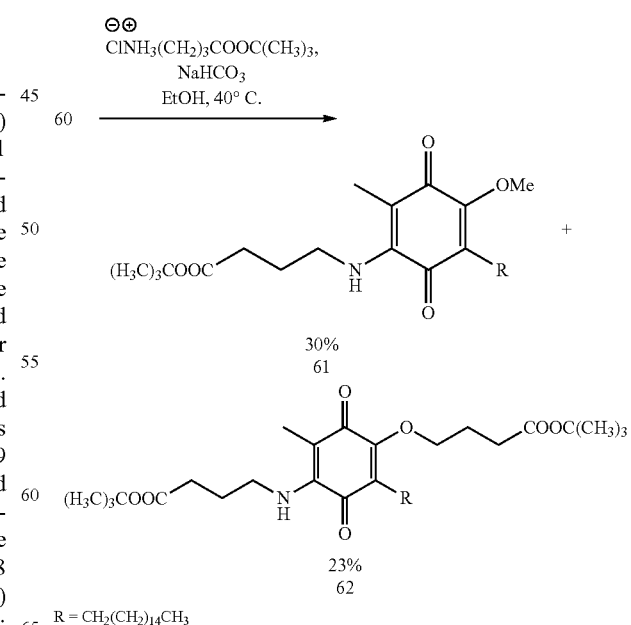

30%
61

23%
62

R = CH$_2$(CH$_2$)$_{14}$CH$_3$

To a solution of 25 mg (0.061 mmol) of 2-hexadecyl-3,6-dimethoxy-5-methylcyclohexa-2,5-diene-1,4-dione 60 and 1.0 g (13 mmol) of sodium bicarbonate in 9.7 mL of ethanol was added 12 mg (0.061 mmol) of γ-aminobutyric acid tert-butyl ester hydrochloride salt. The reaction mixture was stirred for 27 h at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 62 as a bright red amorphous solids: yield—12 mg (62) 30%; silica gel TLC R$_f$ 0.40 (1:2 ethyl acetate-hexanes); $^1$H NMR (CDCl$_3$) (62) δ 0.86 (3H, t, J=7.2 Hz), 1.23-1.37 (28H, m), 1.42 (18H, s), 1.87-1.94 (4H, m), 2.01 (3H, s), 2.29 (4H, m), 2.46 (2H, t, J=8.8 Hz), 3.45 (2H, q, J=6.4 Hz), 3.54 (2H, q, J=6.4 Hz), 6.60-6.65 (2H, m); $^{13}$C NMR (CDCl$_3$) δ14.1, 22.7, 23.6, 24.1, 25.8, 28.1, 29.3, 29.6, 29.6, 29.7, 30.6, 31.9, 32.5, 32.6, 32.8, 41.8, 43.8, 80.7, 80.8, 92.1, 107.8, 146.6, 150.5, 171.8, 171.9, 179.0, 179.5; mass spectrum (APCI), m/z 661.5156 (M+H)$^+$ (C$_{39}$H$_{69}$N$_2$O$_6$ requires m/z 661.5156).

It is noted that compound 61 is also a compound of the invention.

Example 39: Preparation of 2-hexadecyl-3,6-bis-(butyl 4-aminobutanoate)-5-methylcyclohexa-2,5-diene-1,4-dione (64)

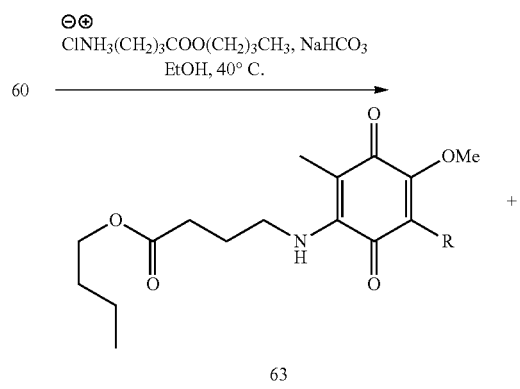

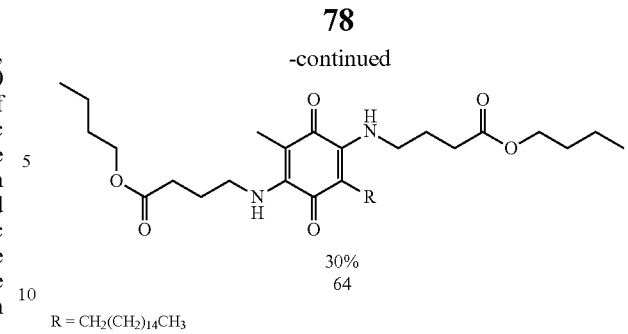

R = CH$_2$(CH$_2$)$_{14}$CH$_3$

To a solution of 25 mg (0.061 mmol) of 2-hexadecyl-3,6-dimethoxy-5-methylcyclohexa-2,5-diene-1,4-dione 60 and 1.0 g (13 mmol) of sodium bicarbonate in 9.7 mL of ethanol was added 12.2 mg (0.063 mmol) of γ-aminobutyric acid n-butyl ester hydrochloride salt. The reaction mixture was stirred for 27 h at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 64 as a bright red amorphous solids: yield—14 mg (64) 35%; silica gel TLC R$_f$ 0.35 (1:2 ethyl acetate-hexanes); $^1$H NMR (CDCl$_3$) δ 0.87 (3H, t, J=7.2 Hz), 0.93 (6H, t, J=7.6 Hz), 1.25-1.32 (26H, m), 1.38 (2H, q, J=7.2 Hz), 1.58 (8H, m), 1.95 (4H, t, J=7.2 Hz), 2.02 (3H, s), 2.40 (6H, m), 3.48 (2H, q, J=6.4 Hz), 3.57 (2H, q, J=6.4 Hz), 4.08 (4H, t, J=6.8 Hz), 6.60-6.65 (2H, m); $^{13}$C NMR (CDCl$_3$) 13.7, 14.1, 19.1, 22.7, 23.5, 24.1, 25.7, 29.3, 29.6, 29.6, 29.7, 30.6, 30.6, 30.6, 31.3, 31.5, 31.9, 41.8, 43.8, 64.6, 64.6, 92.21, 107.9, 146.5, 150.4, 172.6, 172.7, 179.1 and 179.6; mass spectrum (APCI), m/z 661.5156 (M+H)$^+$ (C$_{39}$H$_{69}$N$_2$O$_6$ requires m/z 661.5156).

It is noted that compound 63 is also a compound of the invention.

Example 40: Preparation of 2-hexadecyl-3,6-bis-(hexyl 4-aminobutanoate)-5-methylcyclohexa-2,5-diene-1,4-dione. (66)

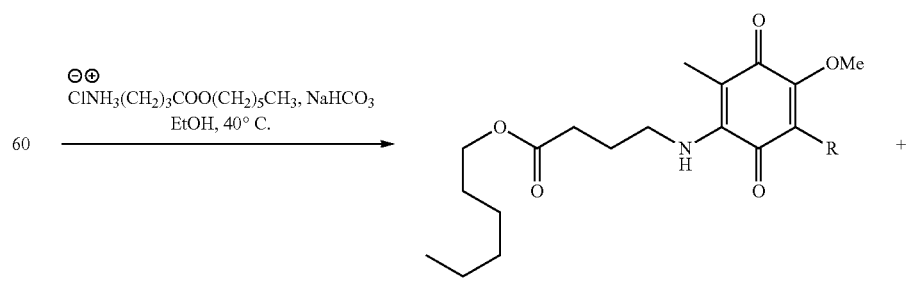

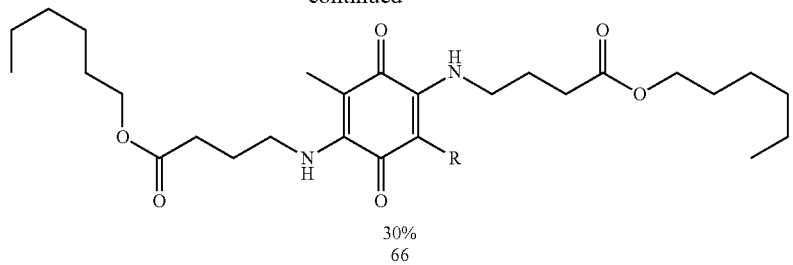

30%
66

R = CH$_2$(CH$_2$)$_{14}$CH$_3$

To a solution of 25 mg (0.061 mmol) of 3-hexadecyl-2,5-dimethoxycyclohexa-2,5-diene-1,4-dione 60 and 1.0 g (13 mmol) of sodium bicarbonate in 9.7 mL of ethanol was added 13.6 mg (0.061 mmol) of γ-aminobutyric acid n-hexyl ester hydrochloride salt. The reaction mixture was stirred for 27 h at room temperature. The reaction mixture was then diluted with 5 mL of water and extracted with seven 2 mL portions of dichloromethane. The organic layer was washed with water, brine and dried (Na$_2$SO$_4$). The excess solvent was concentrated under diminished pressure to afford a crude residue. The residue was purified by flash column chromatography on a silica gel column (24×2 cm). Elution with 1:5 ethyl acetate-hexane gave 66 as a bright red amorphous solids: yield—15 mg (66) 34%; silica gel TLC R$_f$ 0.36 (1:2 ethyl acetate-hexanes); $^1$H NMR (CDCl$_3$) δ 0.87 (9H, m), 1.25-1.38 (36H, m), 1.61 (8H, m), 1.95 (4H, m), 2.02 (3H, s), 2.40 (6H, q, J=9.6 Hz), 3.49 (2H, q, J=6.4 Hz), 3.57 (2H, q, J=6.4 Hz), 4.07 (4H, t, J=6.8 Hz), 6.60-6.65 (2H, m); $^{13}$C NMR (CDCl$_3$) 10.3, 14.0, 14.1, 22.5, 22.7, 24.11, 22.5, 25.7, 26.0, 28.5, 29.3, 29.5, 29.6, 29.7, 30.6, 31.3, 31.3, 31.3, 31.9, 43.8, 44.0, 64.9, 101.5, 106.9, 146.1, 1467.0, 172.6, 172.7, 180.2 and 180.6; mass spectrum (APCI), m/z 717.5782 (M+H)$^+$ (C$_{43}$H$_{77}$N$_2$O$_6$ requires m/z 718.5782).

It is noted that compound 65 is also a compound of the invention.

The biological activity of representative compounds of the invention can be evaluated using known assays or using the assays described in Example 41. Data was generated for representative compounds of the invention in several of the assays described in Example 41. The data is provided in Tables 1-5 and FIGS. 1-9.

Example 41

Reactive Oxygen Species (ROS).

Intracellular ROS production was measured in FRDA lymphocyte cells (GM15850, Coriell Cell Repositories, Camden, N.J.) using the oxidant sensitive fluorescent probe 2,7-dichlorodihydrofluorescein diacetate (DCFH-DA) (Molecular Probes) as described previously (Khdour et al. (2011) Pharm. Res. 28, 2896-2909). One mL of FRDA lymphocyte cells or leukemic CEM cells (5×10$^5$ cells) were plated in a 24-well plate, treated with the test compounds and incubated at 37° C. for 16 h in a humidified atmosphere containing 5% CO$_2$ in air. Cells were treated with 5 mM diethyl maleate (DEM) for 80 min or 60 min respectively, collected by centrifugation at 300×g for 3 min and then washed with phosphate buffered saline (PBS) (Life Technologies). Cells were resuspended in PBS containing 20 mM glucose and incubated at 37° C. in the dark for 25 min with 10 µM DCFH-DA. Cells were collected by centrifugation at 300×g for 3 min and then washed with PBS. The samples were analyzed immediately by flow cytometry (C6 Accuri, BD Biosciences, San Jose, Calif.), using a 488 nm excitation laser and the FL1-H channel 530±15 nm emission filter. The generation of ROS, mainly peroxides, was detected as a result of the oxidation of DCFH. In each analysis, 10,000 events were recorded after cell debris was electronically gated out. Results obtained were verified by running duplicates and repeating experiments in three independent runs. Results were expressed as percentage of ROS scavenging activity.

Assessment of Mitochondrial Membrane Potential (Δ$_{\psi m}$).

Mitochondrial membrane potential was measured using two different fluorescent dyes, TMRM and JC-1. Δ$_{\psi m}$ was determined as previously described by staining FRDA lymphocyte cells with TMRM (Molecular Probes, Eugene, Oreg.) and analyzing fluorescence emission by flow cytometry in detection channel 2 (FL2-H) (Khdour et al. (2011) Pharmaceut. Res. 28, 2896-2909). Briefly, FRDA lymphocytes were pre-treated with or without the test compounds for 16 h. The cells were treated with 5 mM DEM for 140 min, collected by centrifugation at 300×g for 3 min and then washed twice with phosphate buffered saline. The cells were resuspended in PBS containing 20% glucose and incubated at 37° C. in the dark for 15 min with 250 nM TMRM. Cells were collected by centrifugation at 300×g for 3 min and were then washed with phosphate buffered saline. The samples were analyzed immediately by flow cytometry using a 488 nM excitation laser and the FL2-H channel. The results obtained were verified in three independent experiments. FCCP, a mitochondrial uncoupler was used to produce a negative control to dissipate Δ$_{\psi m}$. In each analysis, 10,000 events were recorded. We qualitatively examined the mitochondrial membrane potential using JC-1 dye in primary FRDA fibroblasts GM04078 (Coriell Institute) after treatment with 1 mM BSO, in presence and absence of tested compounds (5 µM). JC-1 is a cationic dye that is accumulated in mitochondria following membrane potential. In polarized mitochondria, it accumulates in aggregated form and appears as red punctate staining whereas in cells having depolarized mitochondria, JC-1 diffuses throughout the cell and appears as green diffused monomeric staining. Briefly, FRDA fibroblasts (2×10$^5$ cells/mL) were seeded in cover slips (Corning, N.Y., USA) in 6-well plates. The plates were incubated at 37° C. overnight in a humidified atmosphere of 5% CO2 in air to allow attachment of the cells to the cover slips. The following day, cells were treated with tested compounds and incubated for an additional 12 h before treatment with 1 mM BSO. Δ$_{\psi m}$ was assessed after 24 h using JC-1 Mitochondrial Membrane Potential Detection Kit (Biotium, Inc) following the manufacturer instruction. Glass cover slips were rinsed with phosphate-buffered saline and mounted onto slides, and images were recorded and analyzed with a Zeiss AxioCam MRm and AxioVision 3.1 software (Carl Zeiss Goettingen, Germany) on a Zeiss Axiovert 200 M inverted microscope, equipped with a 40× oil immersion objective.

Lipid Peroxidation Assay.

Cis-Parinaric Acid Oxidation to Measure Lipid Peroxidation

Several methods for assaying lipid peroxidation in vitro have been developed (Kuypers et al. (1987) *Biochim Biophys Acta.* 25, 266-274; Pap et al. (1999) *FEBS Lett.* 453, 278-282; Drummen et al. (2002) *Free RadicBiol Med.* 33, 473-490). Almost all of these methods are based on inhibition of free radical-induced oxidation reactions. A widely used fluorescence assay for lipid peroxidation uses lipid soluble cis-parinaric acid as a probe. cis-parinaric acid loses its fluorescence ($\lambda_{exc/em}$: 320/432 nm) upon interaction with peroxyl radicals and retains its fluorescence in the presence of radical quenchers. cis-parinaric acid is, however, air sensitive, photolabile and absorbs light in the UV region of the spectrum (at ~320 nm). However, this region of the spectrum is where most compounds have also been found to absorb and emit light. In practical terms, the results obtained using cis-parinaric as a probe for lipid peroxidation are confounded due to the overlapping of the compounds emission spectra with the cis-parinaric emission spectrum.

$C_{11}$-BODIPY$^{581/591}$ Oxidation to Measure Lipid Peroxidation

To overcome the problem of spectral overlap using cis-parinaric acid, a fluorescence assay for lipid peroxidation using a lipophilic probe belonging to the BODIPY class of fluorescent dyes was used $C_{11}$-BODIPY$^{581/591}$ (4,4-difluoro-5(4-phenyl-1,3-butadienyl)-4-bora-3a, 4a-diaza-s-indacene-3-propionic acid) fluorescent shifts from red to green upon oxidation. $C_{11}$-BODIPY$^{581/591}$ (Molecular Probes, Eugene, Oreg., USA) stock solution concentrations were determined by measuring the absorption of $C_{11}$-BODIPY$^{581/591}$ at 582 nm using a molar extinction coefficient of 140,000 mol$^{-1}$ cm$^{-1}$ (R. P. Haugland, (1999) Handbook of Fluorescent Probes and Research Chemicals, Molecular Probes, Inc., Eugene, Oreg.). The lipid peroxidation inducer 2,2'-Azobis (2-amidino-propane dihydrochloride) (AAPH) and the antioxidant compound α-tocopherol (α-TOH) were obtained from Sigma (St. Louis, Mo., USA). Phospholipid bilayers were prepared from 1-stearoyl-2-oleoyl-phosphatidylcholine (SOPC) and 1,2-dilinoleoyl-phosphatidylcholine (DLPC) and were purchased from Avanti® polar lipids, Inc., (Alabaster, Ala., USA).

Preparation of Liposomes

Phosphotidylcholine (PC) liposomes were prepared as described before (Guey-Shuang et al. (1982) *Lipids.* 17, 403-413). Briefly, DLPC (25 mg) were dissolved in chloroform and the solvent was removed by nitrogen evaporation (~2 hours) to give a thin film of PC in a round bottom flask. The lipid film was hydrated with 50 mL of 10 mM Tris-HCl (pH 7.4), 100 mM KCl, shaken and sonicated for 15 seconds. The liposomes obtained were filtered several times through 0.2 μM membrane filter.

Measurement of $C_{11}$-BODIPY$^{581/591}$ Oxidation $C_{11}$-BODIPY$^{581/591}$ was incorporated into liposomes and oxidized by peroxyl radicals derived from the decomposition of AAPH in the presence and absence of compounds. Liposomes (1 mg/mL), suspended in 10 mM Tris-HCl (pH 7.4), 100 mM KCl, were transferred to a quartz 1 mL cuvette and placed in a Varian Cary Eclipse fluorometer (Varian, Cary, N.C.) equipped with a thermostatted cuvette holder at 40° C. Liposomes were pre-incubated for 10 min with 200 nM $C_{11}$-BODIPY$^{581/591}$ to allow their incorporation into the lipid phase of the liposomes. After the addition of AAPH (10 mM) the decay of the red fluorescence was followed at $\lambda$ exc=570 nm, $\lambda$ em=600 nm. Relative fluorescence units were normalized to 100% intensity. Results obtained were verified by repeating experiments N=3 independent experiments.

Measurement of $C_{11}$-BODIPY$^{581/591}$ Oxidation in Cell Culture

A quantitative FACS analysis of lipid peroxidation of FRDA lymphocytes, which had been treated with diethyl maleate following incubation in the presence and absence of the test compounds, was measured as described (Khdour et al. (2011) *Pharmaceut. Res.* 28, 2896-2909). Briefly, FRDA lymphocytes (5×10$^5$ cell/mL) were treated with the test compounds at final concentrations of 5 and 10 μM and incubated at 37° C. for 16 h in a humidified atmosphere containing 5% $CO_2$ in air. Cells were treated with 1 μM $C_{11}$-BODIPY$^{581/591}$ in phenol red-free RPMI-1640 media and incubated at 37° C. in the dark for 30 min. Oxidative stress was induced with 5 mM DEM in phenol red-free RPMI-1640 media for 2 h. Treated cells were collected by centrifugation at 300×g for 3 min and then washed with phosphate buffered saline. Cells were resuspended in phosphate buffered saline and analyzed by FACS (FACS Calibur flow cytometer, Becton Dickinson) to monitor the change in intensity of the $C_{11}$-BODIPY$^{581/591}$-green (oxidized) fluorescence signal. In each analysis, 10,000 events were recorded. Results obtained were verified by running duplicates and repeating experiments in three independent experiments. Results are expressed as % scavenging activity.

Mitochondrial Complex I and NADH Oxidase Activity

Beef heart mitochondria were obtained by a large-scale procedure (Smith et al. (1967) *Methods Enzymol.* 10, 81-86). Inverted submitochondrial particles (SMP) were prepared by the method of Matsuno-Yagi and Hatefi (Matsuno-Yagi et al. (1985) *J. Biol. Chem.* 260, 14424-14427) and stored in a buffer containing 0.25 M sucrose and 10 mM Tris-HCl, pH 7.4, at −80° C. Inhibitory effects of verticipyrone analogues on bovine heart mitochondrial complex I (NADH oxidase and NADH: ubiquinone oxidoreductase) were evaluated by modification of a method described Previously (Hamada et al. (2004) *Biochemistry.* 43, 3651-3658). Stock solutions (2 mg/mL in ethanol) of verticipyrone analogues were prepared and kept in the dark at −80° C. Maximal ethanol concentration never exceeded 2% and had no influence on the control enzymatic activity. The enzymatic activities were assayed at 30° C. and monitored spectrophotometrically with a Molecular Devices SPECTRA Max-M5 (340 nm, e 6.22 mM-$^1$ cm-$^1$). NADH oxidase activity was determined in a reaction medium (2.5 mL) containing 50 mM Hepes, pH 7.5, containing 5 mM MgCl$_2$. The final amount of mitochondrial protein was 30 μg. The reaction was initiated by adding 50 μM NADH after the pre-equilibration of SMP with inhibitor for 5 min. The initial rates were calculated from the linear portion of the traces. The inhibition of NADH-$Q_1$ oxidoreductase (Complex I) activity was also determined under the same experimental conditions except that the reaction medium (2.5 mL) contained 0.25 M sucrose, 1 mM MgCl2, 2 μM Antimycin A, 2 mM KCN, 50 μM ubiquinone $Q_1$ and 50 mM phosphate buffer, pH 7.4. $IC_{50}$ values were taken as the final compound concentrations in the assay cuvette that yielded 50% inhibition of the enzymatic activity.

Cytotoxicity Assay.

Compound 4 and geldanamycin were tested for their cytotoxicity in human breast cancer cell line BT474 and FRDA lymphocytes using the vital mitochondrial function assay WST-1 Kit (Roche Diagnostics). BT474 cells (2000 cell/well) and FRDA lymphocytes (5000 cell/well) (100 μl) were seeded in 96-well plates and incubated for 48 h. Compound 40 or geldanamycin at varying concentrations were added and the plates were returned to the incubator for 48 h. Cell viability was determined using a WST-1 Kit (Roche Diagnostics) following the manufacturer's instructions. WST-1 reagent (10 μL) was added to each well, containing 200 μL media and further incubation for 2 h (BT474) and 4 h (FRDA lymphocytes). Color intensity was measured at 450 nm using a SpectraMax M5 microplate reader (Molecular Devices, Sunnyvale, Calif., USA). Results are expressed as percentage of viable cells relative to untreated control after subtracting background. Data are expressed as means±S.E.M. (n=3).

Cytoprotection (Trypan Blue Exclusion Assay).

Cell viability was determined by trypan blue exclusion assay in Friedreich's ataxia lymphoblast cell line GM15850 (Coriell Institute, New Jersey). This technique was used to assess the cytoprotective effects of the tested compounds in cultured cells treated with DEM to induce cell death by GSH depletion. The viability of DEM-treated FRDA cells was determined by their ability to exclude the dye trypan blue. Viable cells exclude trypan blue, whereas non-viable cells take up the dye and stain blue. Briefly, FRDA lymphocytes were grown in RPMI 1640 medium (Gibco) supplemented with 15% fetal calf serum, 2 mM glutamine (HyClone) and 1% penicillin-streptomycin mix (Cellgro). Cells were seeded at a density of $5 \times 10^5$ cells/mL and treated with different concentrations of the indicated compounds. Cells were incubated at 37° C. in a humidified atmosphere of 5% CO2 in air for 17 h. After pre-incubation, the cells were treated with 5 mM DEM. Cell viability was determined by staining cells with 0.4% trypan blue using a hemacytometer. At least 500 cells were counted in each experimental group. At the time of assay, <20% of DEM treated cells were viable (trypan blue negative), whereas in non DEM-treated control, >90% cells were viable. Cell viability was expressed as the percentage of control. Data are expressed as means±S.E.M. (n=3).

Neuroprotection.

The cytotoxic effect of Aβ 1-42 oligomers (2.5 μM) on differentiated SH-SY5Y cells was evaluated in presence and absence of the test compounds. Sequential treatment of the human SH-SY5Y neuroblastoma cell line with retinoic acid and brain-derived neurotrophic factor (BDNF) generates nearly pure populations of human neuron-like cells, thus providing a model for the study of neuronal differentiation and neuroprotection as previously described, with some modifications (Encinas et al. (2000) *J. Neurochem.* 75, 991-1003). Briefly, human derived neuroblastoma SH-SY5Y cells (CRL-2266, ATCC, Manassas, Va.) were plated in a 6-well plate collagen treated at a density of $5 \times 10^5$ cells/well in complete 1:1 DMEM-F12 (phenol-red free) (10% FBS) and cells were incubated at 37° C. in a humidified atmosphere of 5% $CO_2$ in air for 48 h. Differentiation was initiated with 10 μM all-trans retinoic acid in 1:1 DMEM-F12 (1% FBS) culture media for 5 days. This treatment was replaced on day three to replenish retinoic acid in the culture media. Differentiation was continued for three more days by replacing the media with serum free media ($N_2$ media, Life Technologies) supplemented with BDNF (eBioscience, San Diego, Calif.) (25 ng/mL), this treatment was replaced daily to replenish BDNF in culture media. Wells were treated overnight with the test compounds (0.5, 2.5 and 5 μM) before treatment with oligomeric Aβ 1-42 (2.5 μM). The plates were incubated at 37° C. in an atmosphere having 95% humidity and 5% $CO_2$ for 48 h and then cell viability was measured using a WST-1 Kit (Roche Diagnostics). One hundred μL of WST-1 reagent was added to each well, containing 1 mL medium and further incubated for 3 h. Color intensity was measured with a 96-well plate at 450 nm using a SpectraMax M5 microplate reader (Molecular Devices, Sunnyvale, Calif.). Results are expressed as percentage of viable cells relative to untreated control after subtracting background. Data are expressed as means±S.E.M. (n=3).

Aβ 1-42 Preparation.

Synthetic human Aβ 1-42 was purchased from AnaSpec (San Jose, Calif.). The peptide was dissolved in cold 100% hexafluoro-2-propanol (HFIP) (Sigma) at 1 mM concentration, and then incubated at room temperature (25° C.) for 1 h. The HFIP was evaporated under a nitrogen flow and residual HFIP was removed under diminished pressure using a Speed Vac. The resulting untangled (monomers) Aβ 1-42 film was stored at −20° C. until further manipulation. Immediately prior to use, the HFIP-treated monomers were carefully resuspended to 5 mM in anhydrous dimethylsulfoxide by pipette mixing followed by bath sonication for 10 min. To prepare the oligomeric form by using a standard method (Lambert et al. (1998) *Proc. Nat. Acad. Sci.* USA. 95, 6448-6453; Stine et al. (2003) *J. Biol. Chem.* 278, 11612-11622), the 5 mM peptide aliquot was subsequently diluted to 100 μM with cold Ham's F12 phenol-free medium without glutamine (Life Technologies), immediately vortexed for 30 s, and incubated at 4° C. for 24 h. The preparation was centrifuged at 15,000×g for 10 min at 4° C. to remove insoluble aggregates and pre-formed fibrillar material, and the supernatant containing soluble oligomers was transferred to clean tubes and stored at 4° C. The final concentration of the oligomeric Aβ 1-42 in the supernatant fraction was ~60 μM after removing insoluble material. To obtain fibrils, the peptide was resuspended in 10 mM HCl at a final concentration of 100 μM and incubated at 37° C. for 24 h. Aβ 1-42 peptide content was determined by the method of bicinchoninic acid assay (micro-BCA kit, Pierce) using BSA as reference.

Dot Blot Analysis.

The oligomeric state of amyloid beta preparations was confirmed by dot blot analysis using amyloid oligomer-specific polyclonal antibody A11 (AHB0052, Invitrogen) (Kayed et al. (2003) *Science* 300, 486-489). Briefly, two microliters of the Aβ 1-42 oligomeric preparation were spotted onto nitrocellulose membrane (Bio-Rad Laboratories) and allowed to air dry for one hour. The membrane was blocked in 10% non-fat dry milk in Tris-buffer saline (TBST) containing 0.01% Tween 20 at 4° C. for 1 h. After three 5-min TBST washes, the membranes were probed with conformation specific primary anti-oligomer antibody A11 (Invitrogen: 1:2000) for 1 hour at room temperature in 5% non-fat dry milk in Tris-buffer saline (TBST) containing 0.01% Tween 20. Following three 5-min washes with TBST, the blots were incubated with horseradish peroxidase-linked secondary anti-rabbit antibody IgGs (1:10,000, Sigma, in 5% non-fat dry milk in TBST) at room temperature for 1 hr. The blots were washed three times for 5 min with TBST, rinsed with deionized $H_2O$, and developed with enhanced chemiluminescence (ECL) (BioRad Chemi-Doc) using West Pico Chemiluminescent Substrate (Pierce Biotechnology). Aβ 1-40 fibrils was used as negative control for A11 immunoreactivity.

Hsp90 Client Protein Immunodetection Assay.

The classic method of following the cellular activity of Hsp90 inhibitors is through the proteasome-dependent degradation of Hsp90 client proteins. One such client protein-substrate, the human epidermal receptor 2 (Her2), is a cell surface tyrosine kinase that mediates signal transduction pathways responsible for cell growth and proliferation. Another hallmark of Hsp90 inhibition is the induction of a heat shock response, which was evaluated by determining the Hsp70 protein levels by immunohistochemistry. Hsp70 is a major inducible cellular protein expressed in stress conditions, and has been shown to exert neuroprotective functions. A microtiter cell-based assay that sensitively detects cellular levels of Her2 and Hsp70 in BT474 cells human breast ductal carcinoma tumor cell line, (HTB-20, ATCC, Manassas, Va.) overexpressing Her2 was used to evaluate the test compounds for inhibition of Hsp90 as described before (Huezo et al. (2003) *Chem. Biol.* 10, 629-634; Ahn et al. (2011) *Assay Drug Dev Technol.* 9, 236-246). Briefly, BT474 cells were grown in 1:1 DMEM-F12 medium containing 10% fetal bovine serum, 2 mM glutamine and 1% penicillin-streptomycin. Cells were seeded (3000 cells per well) in 100 μL of growth media in 96-well plates (black clear-bottom microtiter plates, Corning), and allowed to attach at 37° C. for 48 h in a humidified atmosphere of 5% CO2 in air. Compound 40 or geldanamycin was added to the wells at varying concentrations, and the plates were incubated again for 24 h. Growth media was removed and cells were washed twice with ice-cold Tris buffer saline containing 0.1% Tween 20 (TBST). Methanol (50 μL) (−20° C.) was added and the plates were placed at 4° C. for 10 min to permeabilize and fix the cells. Methanol was removed by washing with TBST (two 100-μL portions). The plates were further incubated with 100 μL SuperBlock (Pierce Biotechnology, Rockford, Ill.) for 1 h at room temperature. The plates were incubated with the primary antibody (anti-Her2 or anti-Hsp70, Santa Cruz Biotechnology, CA) overnight at 4° C. at a dilution of 1:200 in 100 μL of SuperBlock. The plates were washed again and incubated at room temperature for 2 h in the presence of horseradish peroxidase-conjugated secondary IgG (Sigma) dissolved in TBS containing 5% bovine serum albumin (BSA) and 0.1% Tween 20 (100 μL, 1:1000 in SuperBlock). Unreacted antibody was removed by washing with TBST (three 200-μL portions), and the chemiluminescent reagent was added (100 μL) (Pierce Biotechnology, Rockford, Ill.). The plates were read immediately on a luminometer (Clarity™ luminescence microplate reader). Readings from wells containing only control IgG and the corresponding horseradish peroxidase-linked secondary antibody were set as background and subtracted from all measured values. The average chemiluminescence signals obtained were expressed as a percentage of Her2 reduction or Hsp70 induction in comparison to vehicle (DMSO). Values were calculated from three independent experiments performed in triplicate.

Results

Inhibition of ROS and Lipid Peroxidation.

The ability of the synthesized analogues to quench ROS and lipid peroxidation was evaluated in FRDA lymphocytes or leukemic CEM cells. These cells were placed under oxidative stress by depleting them of glutathione (GSH) using diethyl maleate (DEM). Depletion of glutathione by treatment FRDA lymphocytes or leukemic CEM cells with DEM has been used to induce oxidative stress in cellular systems by generation of ROS. Intracellular ROS production was measured using the oxidant sensitive fluorescent probe 2,7-dichlorodihydrofluorescein diacetate (DCFH-DA) (Molecular Probes). The results in (Table 1, and FIGS. 1, 2) show that analogues 7 and 40 were very effective in suppressing ROS than natural product 8.

The extent of lipid peroxidation was quantified using a fatty acid sensitive fluorescent reporter $C_{11}$-BODIPY$^{581/591}$ (Molecular Probes). Upon oxidation of the phenylbutadiene moiety of the fluorophore, the red emitting form of the dye (595 nm) is converted into a green emitting form (520 nm). Increased $C_{11}$-BODIPY$^{581/591}$-green (oxidized) fluorescence, a measure of peroxyl radical production, was determined by flow cytometric analysis, which is expressed as % scavenging activity. The results in Table 2 show that analogue 30 was very effective in suppressing lipid peroxidation at 5 and 10 μM concentrations (97 and 100% suppression of lipid peroxidation), while the natural product 8 was much less active (24% suppression at 10 μM concentration). Methoxyquinones 7, 18 and 20 also exhibited concentration-dependent suppression of lipid peroxidation, affording 86, 98 and 70% suppression, respectively, at 10 μM concentration. Compound 40 was very effective in suppressing lipid peroxidation at 5 and 10 μM concentrations (72 and 83% suppression, respectively), while hydroxyquinone 19 was much less potent (38% suppression at 10 μM concentration).

Preservation of Mitochondrial Membrane Potential ($\Delta_{\psi m}$).

Figure 3:
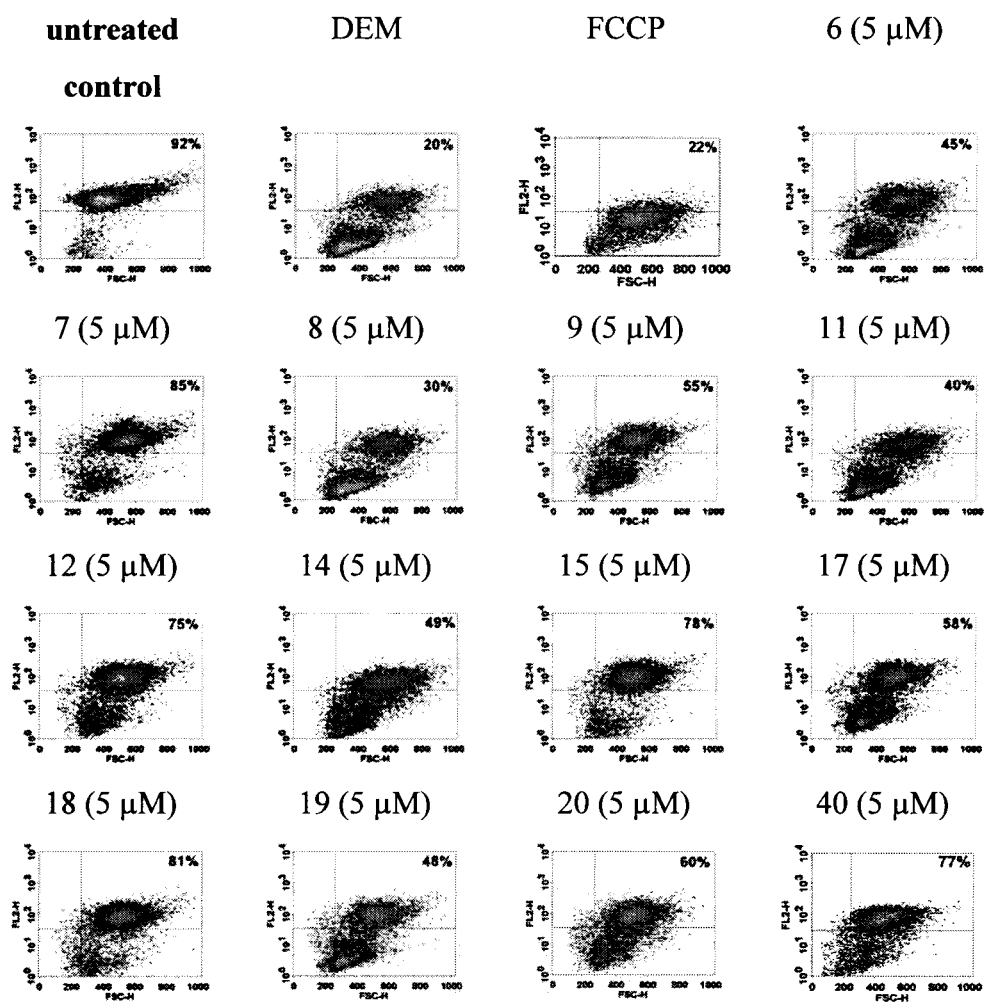
FIG. 3. Effect of nitrogen-containing 1,4-benzoquinone derivatives on mitochondrial membrane potential of cultured FRDA cells. Representative flow cytometric two dimensional color density dot plot analyses of mitochondrial membrane potential $\Delta_{\psi m}$ in FRDA lymphocytes stained with TMRM and analyzed using the FL2-H channel as described in Experimental Section. The cells were washed twice in phosphate buffered saline, and suspended in phosphate buffered saline containing 20 mM glucose. The percentage of cells with intact $\Delta_{\psi m}$ is indicated in the top right quadrant of captions. In each analysis, 10,000 events were recorded. Data are expressed as means±SEM of three independent experiments run in duplicate. The bar graph shows the percentage of cells with intact $\Delta_{\psi m}$ calculated using Cell-Quest software.
Figure 3:
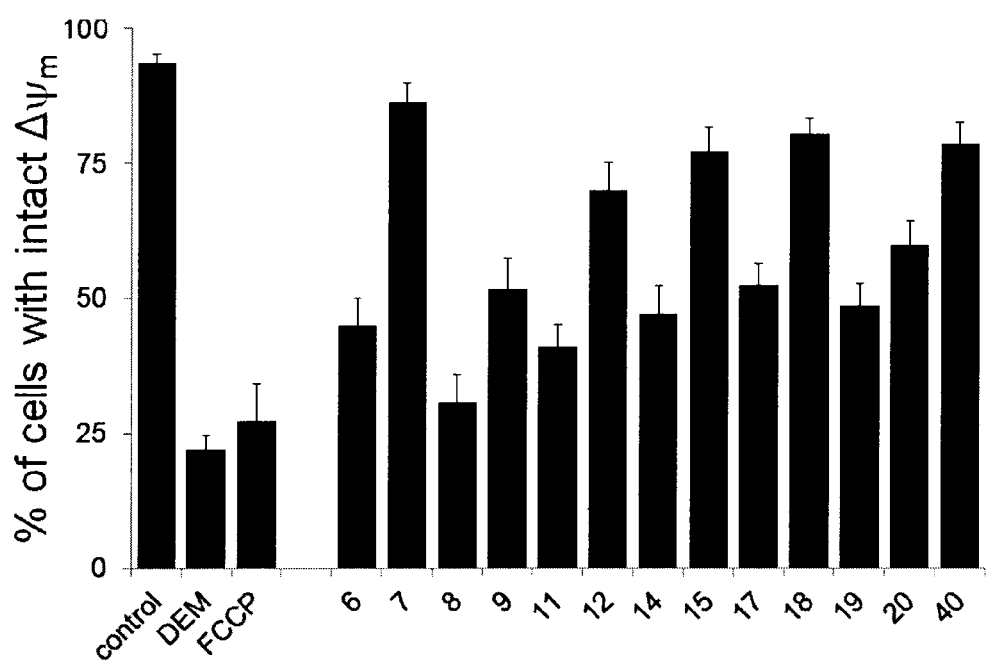
Figure 4:
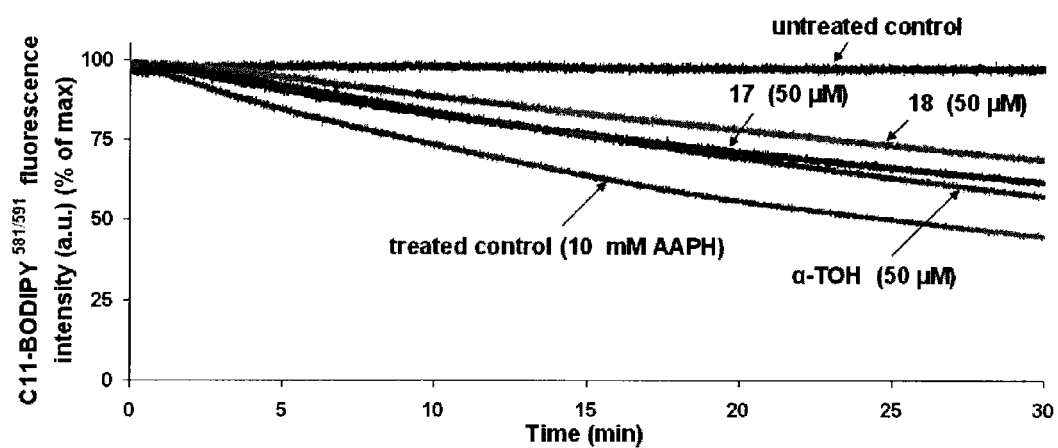
FIG. 4. Effect of nitrogen-containing 3-alkyl-1,4-benzoquinone derivatives on lipid peroxidation induced by peroxyl radicals generated from thermal decomposition of AAPH in phospholipid liposomes in phosphate buffer at 40° C. Compound 18 showed significant protection against lipid peroxidation as compared with tocopherol by measuring their ability to preserve the fluorescence of $C_{11}$-BODIPY$^{581/591}$ in presence of 10 mM AAPH. Relative fluorescence units are normalized to 100% intensity.
Figure 5:
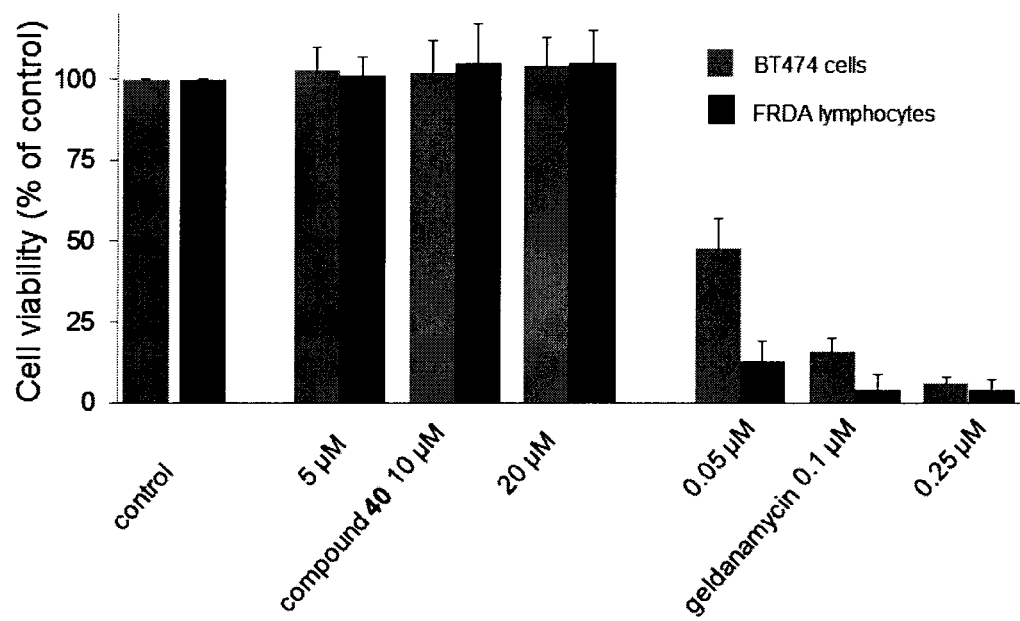
FIG. 5. Effect of compound 40 and geldanamycin on cell viability was compared to vehicle (DMSO) after treatment with varying concentrations for 48 h in BT474 cell line and FRDA lymphocytes, respectively. Each measurement is an average of three independent experiments run in quartet.
Figure 6:
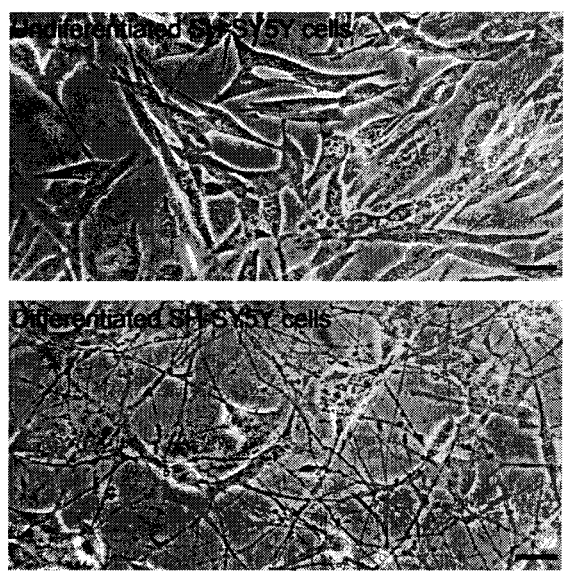
FIG. 6. Phase-contrast microscopy of SH-SY5Y cells, showing the morphological change in SH-SY5Y cells differentiated from mitotic into postmitotic (neuron-like) cells displaying morphological and biochemical features of mature neurons. Top panel, neuroblastoma cells before differentiation. Bottom panel, SH-SY5Y cells after sequential treatment for 5 days with retinoic acid (10 µM) followed by differentiation with brain derived neurotrophic factor (BDNF: 25 ng/ml) for three days; at this time point most cells are postmitotic and exhibit long neurite formation.
Figure 7:
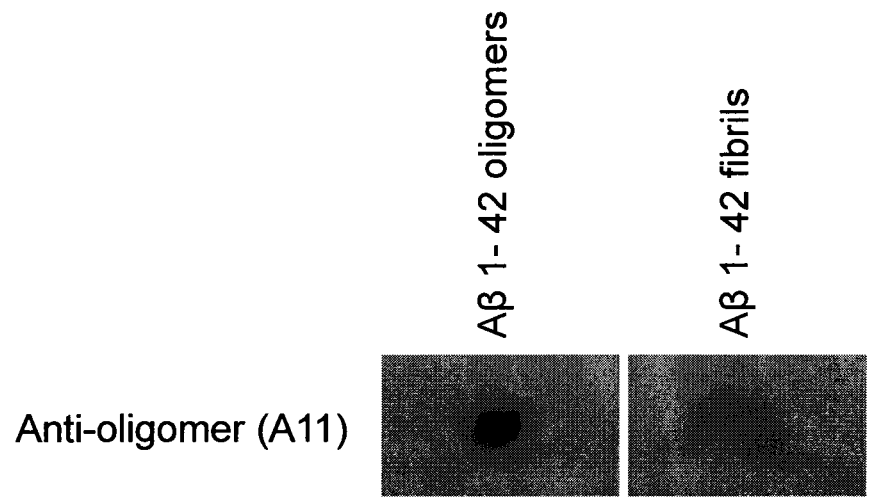
FIG. 7. The Aβ 1-42 oligomer formation during the peptide aggregation experiments was assessed by dot-blot analysis using rabbit polyclonal A11 anti-oligomer antibody (Invitrogen), which recognizes oligomers but not monomers or fibrils. Peptides were spotted onto nitrocellulose membrane and incubated with the antibody. Signals were detected by enhanced chemiluminescence (ECL).
Figure 8:
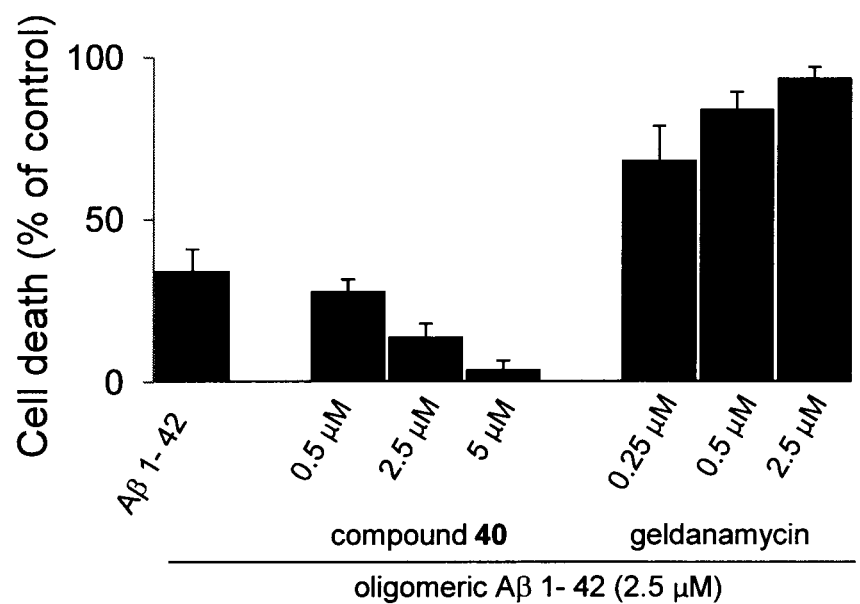
FIG. 8. Effect of nitrogen-containing 1,4-benzoquinone 40 and geldanamycin on Aβ 1-42 induced neurotoxicity in differentiated SH-SY5Y cells.
Figure 9:
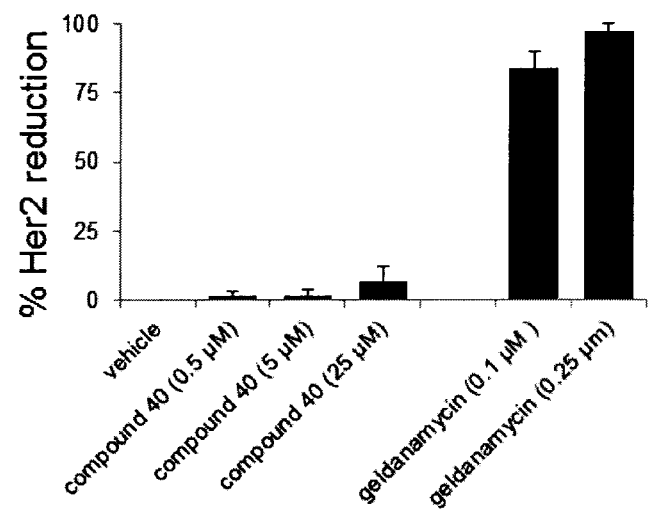
FIG. 9. A cell-based immunodetection assay was used to monitor Hsp90 client protein, Her2 protein degradation (A), and the induction of a heat shock response Hsp70 protein levels (B) in Her2-overexpressing BT474 cell line. The effects of 40 and geldanamycin were compared to vehicle (DMSO) after treatment with varying concentrations of the compounds for 24 h. Each measurement is an average of three independent experiments run in quartet.
Figure 9:
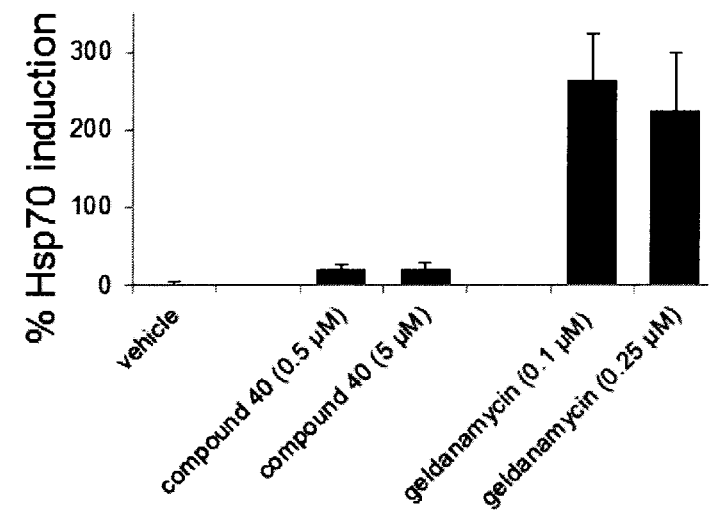

The ability of the test compounds to preserve mitochondrial membrane potential under conditions of oxidative stress was studied. Assessment of $\Delta_{\psi m}$ is an important indicator of cellular function during stress-induced cell death. Changes in mitochondrial membrane potential ($\Delta_{\psi m}$) were measured using two different fluorescent dyes, tetramethylrhodamine methyl ester (TMRM) and 5,5',6,6'-tetrachloro-1,1',3,3'-tetraethylbenzimidazolocarbocyanine iodide (JC-1). TMRM is a potentiometric, cell-permeable fluorescent indicator that accumulates in the highly negatively charged interior of mitochondria inner membrane in a Nernstian manner. The fluorescence signal of TMRM can be directly co-related to $\Delta_{\psi m}$ across the inner mitochondrial membrane. Therefore the accumulation of dye into mitochondria and the intensity of signal is a direct function of mitochondrial potential. Loss of mitochondrial membrane potential is indicated by a reduction in TMRM red fluorescence. The detection of mitochondrial depolarization using TMRM was accomplished by flow cytometry. FIG. 3 illustrates representative two-dimensional density dot plots of TMRM-stained lymphocyte cells showing the percentage of cells with intact $\Delta_{\psi m}$ (TMRM fluorescence in top right quadrant) vs. the percentage of cells with reduced $\Delta_{\psi m}$ (TMRM fluorescence in bottom left and right quadrants). The results show that DEM treatment decreased the percentage of cells with TMRM fluorescence in the top right quadrant, indicating that DEM treatment caused depolarization of $\Delta_{\psi m}$. Compound 7 preserved mitochondrial membrane potential as compared to the natural product 8. The methoxy hydroquinone esters 15, 18 and the cyclic analogue 40 prevented the loss of $\Delta_{\psi m}$, consistent with the cytoprotection results.

These data (FIG. 3) indicate that compound 7 and 40 are able to prevent oxidative-stress induced collapse of $\Delta_{\psi m}$, an event indicating mitochondrial function disruption that occurs prior to cell death. The results show that compound 7 and 40 are able to prevent ROS-induced damage of intracellular lipids, and are able to maintain mitochondrial function and confer cytoprotection in FRDA lymphocytes despite severe oxidative stress.

Mitochondrial Complex I and NADH Oxidase Activity.

Data for representative compounds is shown in Tables 4 and 5.

Cytoprotection.

The synthesized analogues were tested for their ability to confer cytoprotection to cultured cells as shown in Table 3.

Cell viability was determined by trypan blue exclusion assay in Friedreich's ataxia lymphoblast cell line GM15850 (Coriell Institute). This technique was used to assess the cytoprotective effects of the compounds in cultured cells treated with diethyl maleate (DEM) to induce cell death by glutathione (GSH) depletion. The viability of DEM-treated FRDA cells was determined by their ability to exclude the dye trypan blue. Viable cells exclude trypan blue, whereas non-viable cells take up the dye and stain blue. As outlined in Table 1, compound 7 was the most efficient, exhibiting 80% cytoprotection at 0.5 µM concentration. Benzoquinone analogue 9 afforded greater cyoprotection to FRDA lymphocytes at 5 µM concentration than did the tert-butyl ester 6 (74 vs 50%). The natural product 8 afforded the least protection when tested at this concentration.

As shown below, the methoxyquinones 7, 9, 12, 15, 18, 20, 30 and 26 offered greater cytoprotection when compared to their corresponding hydroxyquinones 6, 8, 11, 14, 17, 19, 29 and 25. The N-methylated compound 30 exhibited similar activity to unmethylated 7 at a concentration of 2.5 µM. The alkyl esters 15 and 18 also exhibited similar activities at tested concentrations. The cyclic analogue 40 offered concentration-dependent cytoprotection, affording 83% protection at 2.5 µM concentration.

The ability of 40 to protect differentiated SH-SY5Y cells (FIG. 6) against Aβ-induced cell death was also studied. Compound 40 decreased Aβ 1-42 induced cytotoxicity in a concentration dependent manner as shown (FIG. 8), while geldanamycin actually increased cytotoxicity at comparable concentrations. In addition, compound 40 itself exhibited no cytotoxicity (FIG. 9) and did not inhibit Hsp90, as judged by its lack of effect on the client proteins Her2 and Hsp70 (FIG. 10) the cellular locus of geldanamycin action.

TABLE 1

Suppression of ROS Production in Cultured CEM leukemia Cells Pretreated with DEM.

| Compound | Scavenging activity (%) 5 µM |
|---|---|
| untreated control | 100 |
| treated control | 0 |
| 43 | 35 ± 6 |
| 44 | 0 |
| 46 | 50 ± 5 |
| 47 | 25 ± 11 |
| 49 | 16 ± 8 |
| 50 | 14 ± 1 |

TABLE 2

Suppression of lipid peroxidation by 3-alkyl-1,4-benzoquinone derivatives of N-(3-carboxylpropyl)-5-amino-2-hydroxy-3-tridecyl-1,4-benzoquinone (8) antioxidants in cultured FRDA lymphocytes treated with diethyl maleate (DEM)[a]

| Compound | Scavenging activity (%) | | |
|---|---|---|---|
| | 1 µM | 5 µM | 10 µM |
| untreated control[b] | | 100 | 100 |
| treated control[c] | | 0 | 0 |
| 6 | | 26 ± 6.7 | 37 ± 1.4 |
| 7 | | 72 ± 1.8 | 86 ± 1.8 |
| 8 | | 8.0 ± 6.6 | 24 ± 7.4 |
| 9 | | 41 ± 7.2 | 51 ± 5.0 |
| 17 | | 9 ± 2.5 | 40 ± 9.9 |
| 18 | | 81 ± 1.6 | 98 ± 1.2 |
| 19 | 2 ± 0.3 | 27 ± 4.5 | 38 ± 6.0 |

TABLE 2-continued

Suppression of lipid peroxidation by 3-alkyl-1,4-benzoquinone derivatives of N-(3-carboxylpropyl)-5-amino-2-hydroxy-3-tridecyl-1,4-benzoquinone (8) antioxidants in cultured FRDA lymphocytes treated with diethyl maleate (DEM)[a]

| Compound | Scavenging activity (%) | | |
|---|---|---|---|
| | 1 µM | 5 µM | 10 µM |
| 20 | 14 ± 1.3 | 61 ± 7.5 | 70 ± 5.8 |
| 30 | | 97 ± 2.1 | 100 ± 1.60 |
| 40 | 29 ± 4.7 | 72 ± 6.3 | 83 ± 2.1 |
| 43 | | 61 ± 4 | 75 ± 2 |
| 44 | | 8 ± 3 | 13 ± 3 |
| 46 | | 60 ± 1 | 70 ± 3 |
| 47 | | 7 ± 1 | 19 ± 2 |
| 49 | | 8 ± 3 | 13 ± 3 |
| 50 | | 18 ± 1 | 23 ± 4 |

[a]Values have been calculated as [(100 − % mean)/(100 − % mean of the untreated control)] × 100.
[b]No DEM treatment.
[c]DEM treatment.

TABLE 3

Cytoprotection of cultured FRDA lymphocytes from the effects of oxidative stress[a]

| Compounds | Concentration of test compounds | | | | |
|---|---|---|---|---|---|
| | 5 µM | 2.5 µM | 1 µM | 0.5 µM | 0.1 µM |
| 6 | 50 ± 2.9 | | | | |
| 7 | 93 ± 4.0 | 84 ± 5.0 | 80 ± 4.0 | 80 ± 2.0 | |
| 8 | 36 ± 7.3 | | | | |
| 9 | 74 ± 5.5 | | | | |
| 11 | 48 ± 5.8 | | | | |
| 12 | 71 ± 6.4 | | | | |
| 14 | 58 ± 9.0 | | | | |
| 15 | 82 ± 2.9 | | | | |
| 17 | 49 ± 9.9 | | | | |
| 18 | 90 ± 2.0 | | | | |
| 19 | 65 ± 5.2 | 43 ± 4.4 | | 22 ± 2.6 | 18 ± 2.1 |
| 20 | 80 ± 4.0 | 66 ± 6.3 | | 50 ± 5.2 | 20 ± 3.2 |
| 25 | | 24 ± 3.0 | | 18 ± 4.0 | 21 ± 3.0 |
| 26 | | 90 ± 3.0 | | 66 ± 3.0 | 53 ± 9.0 |
| 29 | | 74 ± 4.0 | 21 ± 6.0 | | |
| 30 | | 82 ± 5.0 | 64 ± 15 | | |
| 40 | 92 ± 3.5 | 83 ± 5.4 | | 69 ± 2.3 | 36 ± 4.3 |
| 43 | 91 ± 6 | | 67 ± 5 | | |
| 44 | 98 ± 6 | | 15 ± 2 | | |
| 46 | 95 ± 3 | | 63 ± 4 | | |
| 47 | 17 ± 3 | | 9 ± 2 | | |
| 49 | 87 ± 4 | | 16 ± 4 | | |
| 50 | 91 ± 3 | | 11 ± 2 | | |

[a]The viability of untreated cells was defined as 100%; cells treated with DEM alone had 18 ± 10% viability.

TABLE 4

Complex I inhibition

| Compound | Complex I inhibition | |
|---|---|---|
| | $IC_{50}$ (µM) | $I_{max}$ (%) |
| 6 | 10 ± 0.6 | 64 ± 13 |
| 7 | 540 ± 17 | >85 ± 2.3 |
| 8 | 2.0 ± 0.1 | 84 ± 1.3 |
| 9 | 1.9 ± 0.1 | 98 ± 2.8 |
| 11 | 1.7 ± 0.1 | 70 ± 0.31 |
| 12 | 34 ± 2.5 | ≥53 ± 1.5 |
| 14 | 11 ± 0.6 | 58 ± 4.0 |
| 15 | 98 ± 8 | ≥60 ± 4.7 |
| 17 | 2.0 ± 0.4 | 51 ± 1.4 |
| 18 | 513 ± 38 | >85 ± 3.2 |

TABLE 4-continued

Complex I inhibition

| Compound | IC$_{50}$ (μM) | I$_{max}$ (%) |
|---|---|---|
| 19 | 20 ± 1.7 | 77 ± 6.2 |
| 20 | 482 ± 24 | >85 ± 3.6 |
| 23 | 3.4 ± 0.1 | 78 ± 0.8 |
| 24 | 1.9 ± 0.1 | 90 ± 0.7 |
| 25 | 1.5 ± 0.1 | 90 ± 3.4 |
| 26 | 1.6 ± 0.03 | 90 ± 1.1 |

TABLE 5

NADH oxidase activity (complexes I, III and IV)

NADH oxidase activity (Complex I, III, IV) %

| Compound | 10 μM | 5 μM | 1 μM |
|---|---|---|---|
| 7 | | 77 ± 4.0 | 84 ± 1.0 |
| 8 | | 62 ± 3.0 | 77 ± 4.0 |
| 12 | | 48 ± 3.0 | 67 ± 6.0 |
| 18 | | 27 ± 3.0 | 54 ± 5.0 |
| 19 | | 39 ± 1.0 | 67 ± 6.0 |
| 20 | | 47 ± 3.0 | 74 ± 16 |
| 23 | 18 ± 0.5 | 36 ± 1.0 | 82 ± 2.4 |
| 24 | 17 ± 0.4 | 33 ± 0.9 | 81 ± 1.5 |
| 25 | 5.0 ± 0.1 | 6.6 ± 0.1 | 18 ± 0.5 |
| 26 | 15 ± 0.4 | 34 ± 0.6 | 70 ± 2.1 |
| 40 | 70 ± 1 | 85 ± 1 | 95 ± 3 |
| 43 | 80 ± 1 | 85 ± 1 | 87 ± 2 |
| 44 | 84 ± 3 | 92 ± 3 | 95 ± 2 |
| 46 | 68 ± 1 | 84 ± 4 | 86 ± 2 |
| 47 | 69 ± 2 | 68 ± 1 | 77 ± 1 |
| 49 | 74 ± 2 | 83 ± 2 | 74 ± 2 |
| 50 | 70 ± 3 | 78 ± 6 | 85 ± 1 |

Example 42

The following illustrate representative pharmaceutical dosage forms, containing a compound of formula I ('Compound X'), for therapeutic or prophylactic use in humans.

| | mg/tablet |
|---|---|
| (i) Tablet 1 | |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |
| (iii) Capsule | mg/capsule |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |
| | mg/ml |
| (iv) Injection 1 (1 mg/ml) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula Ib:

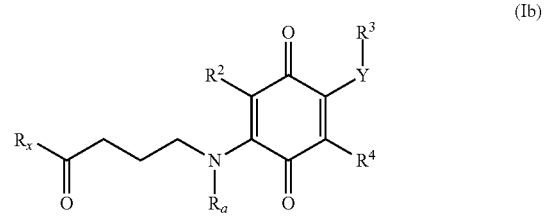

(Ib)

wherein:
R$^2$ is H, cyano, nitro, halo, aryloxy, —OC$_1$-C$_{20}$alkyl, —OC$_2$-C$_{20}$alkenyl, —OC$_2$-C$_{20}$alkynyl, —NR$_b$R$_c$, —C(=O)NR$_b$R$_c$, or —C(=O)OR$_d$;

Y and R$^3$ taken together are H, cyano, nitro, halo, aryloxy, —OC$_1$-C$_{20}$alkyl, —NR$_a$(C$_1$-C$_{20}$alkyl), —NR$_a$(aryl), —C$_1$-C$_{20}$alkyl, —C$_2$-C$_{20}$alkenyl, or —C$_2$-C$_{20}$alkynyl;

R$^4$ is a C$_1$-C$_{20}$alkyl, C$_2$-C$_{20}$alkenyl, or C$_2$-C$_{20}$alkynyl;

R$_a$ is H, C$_1$-C$_{20}$alkyl, C$_2$-C$_{20}$alkenyl, C$_2$-C$_{20}$alkynyl, or C$_1$-C$_{20}$alkanoyl;

R$_x$ is C$_1$-C$_{16}$alkyl, C$_2$-C$_{16}$alkenyl, C$_2$-C$_{16}$alkynyl, aryl, —OC$_1$-C$_{16}$alkyl, —OC$_2$-C$_{16}$alkenyl, —OC$_2$-

C$_{16}$alkynyl, aryloxy, —N(H)C$_1$-C$_{16}$alkyl, —N(H)C$_2$-C$_{16}$alkenyl, —N(H)C$_2$-C$_{16}$alkynyl, or —N(H)aryl;
or a salt thereof.
2. A compound selected from:
7
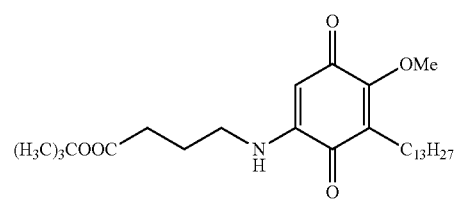
9
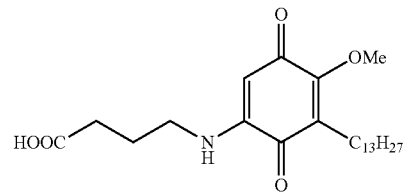
11
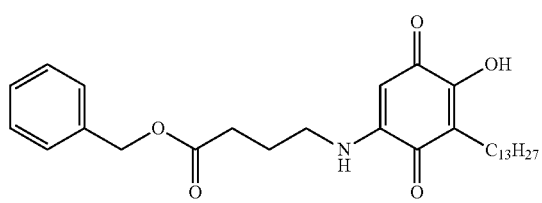
14
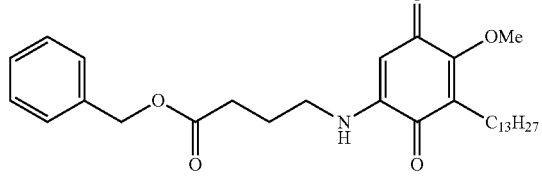
15
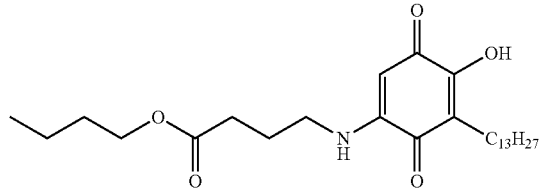
17
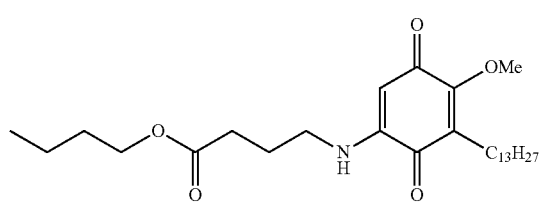
18
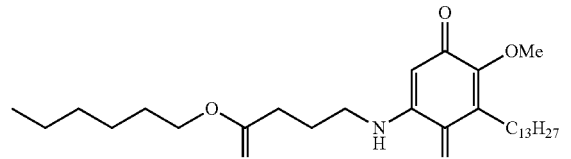
19
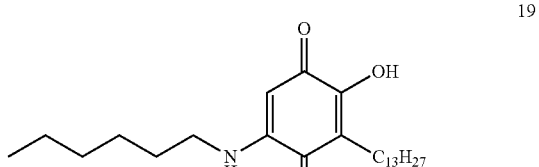
20
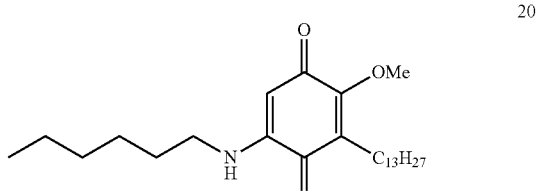
23
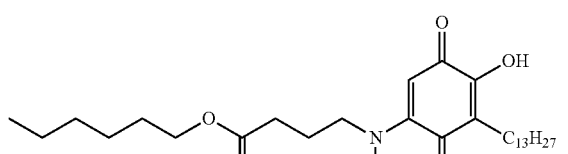
24
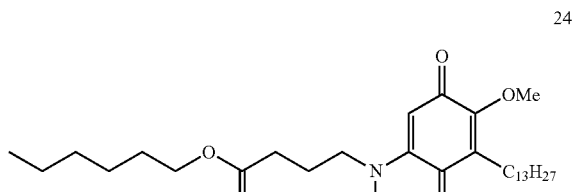
25
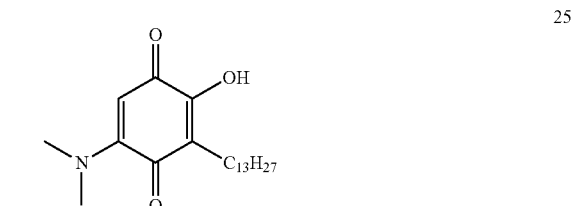
29
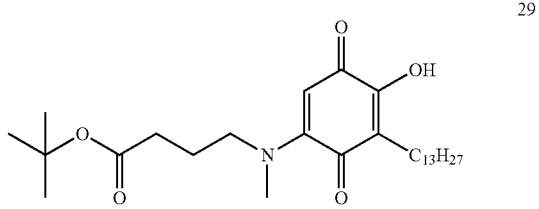
30
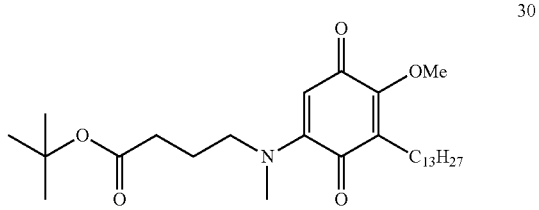
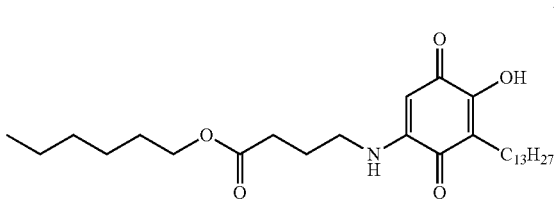

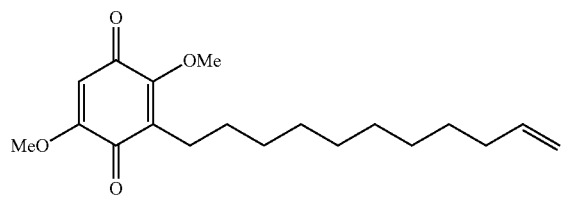
35
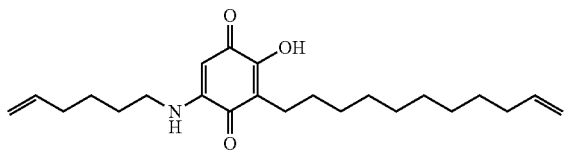
37
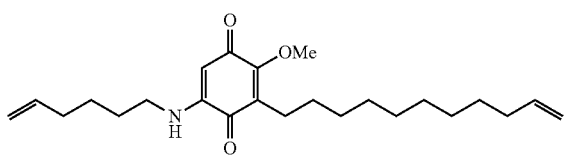
38
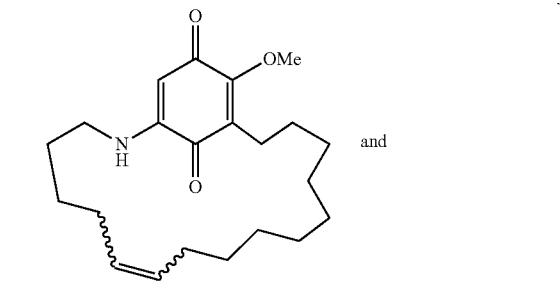
and
39
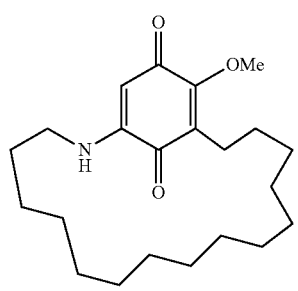
and salts thereof.
3. A compound selected from:
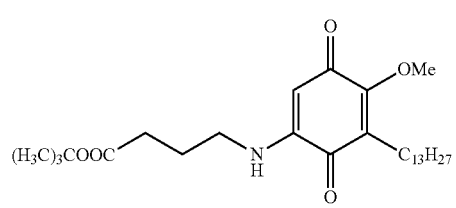
7
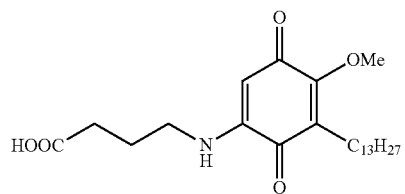
9
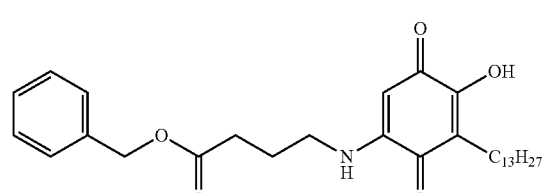
11
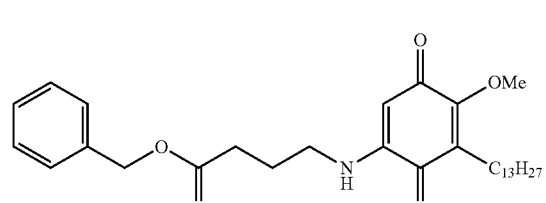
12
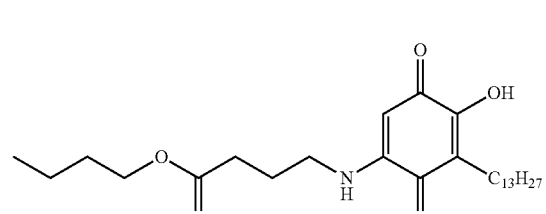
14
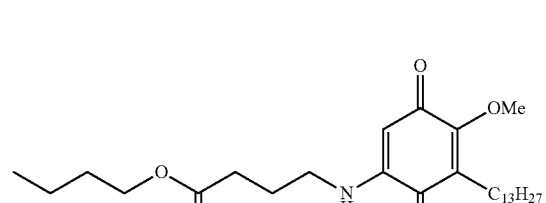
15
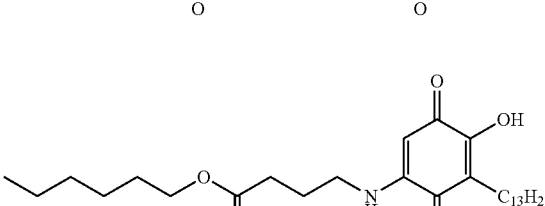
17
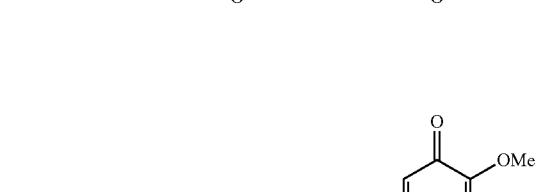
18

19
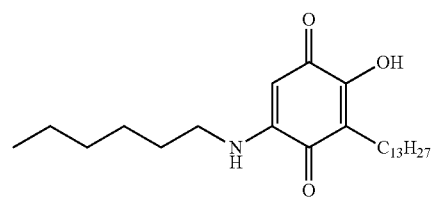
20
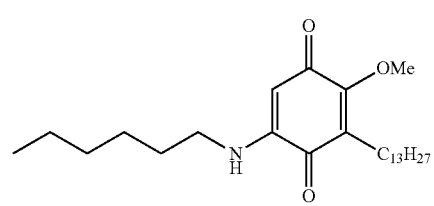
23
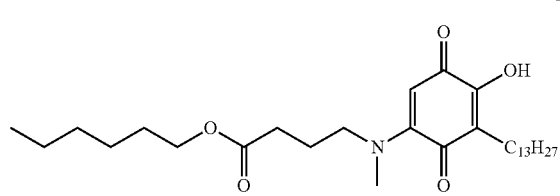
24
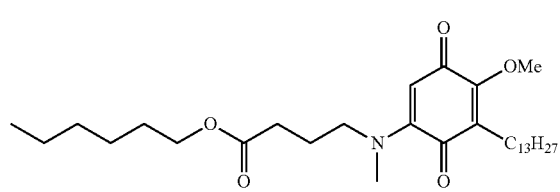
25
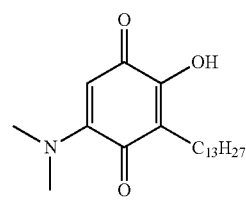
29
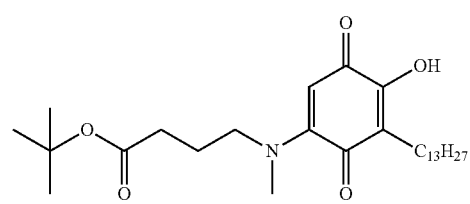
30
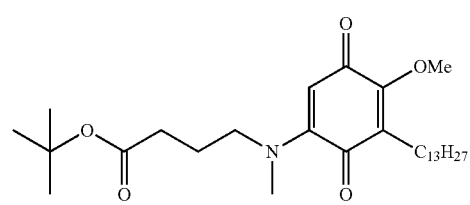
35
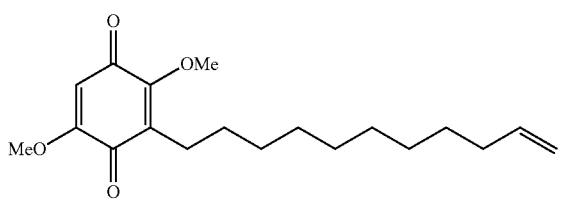
37
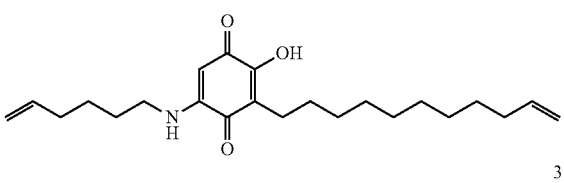
38
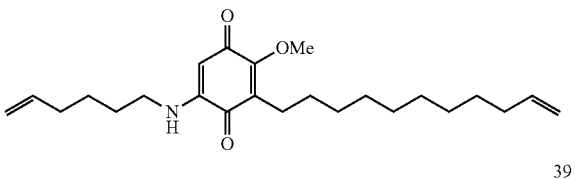
39
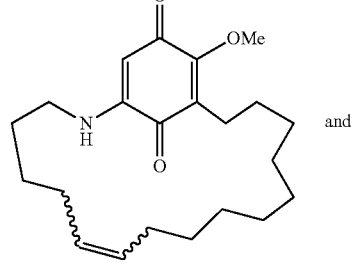
40
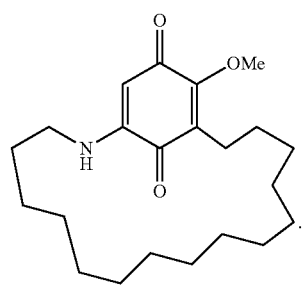
4. A compound of formula I:
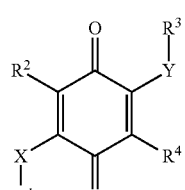
(I)
wherein:
X is NR$_a$ or —C(=O)N(R$_a$)—;
R$_a$ is H or methyl;
R$^1$ is a C$_1$-C$_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^1$ can be optionally substituted with one or more groups independently selected from halo, aryl, and oxo (=O);

$R^2$ is H or methyl;

Y and $R^3$ taken together are methoxy, 3-(tert-butoxycarbonyl)prop-1-yloxy, N-(3-(butoxycarbonyl)prop-1-yl)amino, N-(3-(hexyloxycarbonyl)prop-1-yl)amino, 3-(butoxycarbonyl)prop-1-yloxy, or 3-(hexyloxycarbonyl)prop-1-yloxy; and $R^4$ is tridecyl, hexadecyl, or 10-undecen-1-yl;

or a salt thereof;

provided the compound is not:

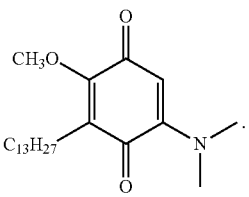

5. The compound of claim 4 wherein X is $NR_a$.

6. The compound of claim 4 wherein $R_a$ is H.

7. The compound of claim 4 wherein $R^1$ is a $C_1$-$C_{20}$ straight or branched, saturated or unsaturated carbon chain, wherein one or more carbon atoms can optionally be replaced with —O—; wherein $R^1$ can be optionally substituted with one or more groups independently selected from aryl and oxo (=O).

8. A compound of formula I:

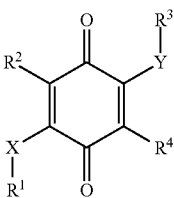

(I)

wherein:

X is $NR_a$, or —C(=O)N($R_a$)—;

$R^1$ is a $C_1$-$C_{20}$ straight or branched, saturated or unsaturated carbon chain, wherein one or more carbon atoms can optionally be replaced with —O—, —NH—, a divalent phenyl group, or a divalent $C_3$-$C_6$cycloalkyl group; wherein $R^1$ can be optionally substituted with one or more groups independently selected from halo, aryl, and oxo (=O);

$R^2$ is H,

Y is O, $R^3$ is aryl, or a $C_1$-$C_{20}$ straight or branched, saturated or unsaturated carbon chain other than methyl;

$R^4$ is a $C_1$-$C_{20}$ straight or branched, saturated or unsaturated carbon chain, wherein one or more carbon atoms can optionally be replaced with a divalent phenyl group, or a divalent $C_3$-$C_6$cycloalkyl group; wherein $R^4$ can be further optionally substituted with one or more groups independently selected from halo, oxo (=O), carboxy, $C_1$-$C_3$alkyl, $C_1$-$C_3$alkoxy, nitro, —$SO_3H$, or tetrazolyl; or $R^1$ and $R^4$ taken together form a $C_3$-$C_{18}$ straight or branched, saturated or unsaturated carbon chain that can be optionally substituted with one or more groups independently selected from halo and oxo (=O); and $R_a$ is H;

or a salt thereof.

* * * * *

UNITED STATES PATENT AND TRADEMARK OFFICE
CERTIFICATE OF CORRECTION

| | | |
|---|---|---|
| PATENT NO. | : 9,957,214 B2 | Page 1 of 1 |
| APPLICATION NO. | : 14/434725 | |
| DATED | : May 1, 2018 | |
| INVENTOR(S) | : Manikandadas Mathilakathu Madathil, Omar Khdour and Sidney Hecht | |

It is certified that error appears in the above-identified patent and that said Letters Patent is hereby corrected as shown below:

In the Claims

Column 91, Lines 33-40, Claim 2, please delete the following compound:

"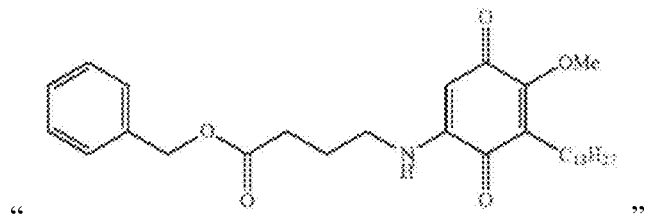"

And insert:

-- 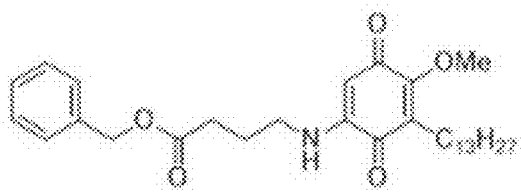

12

-- therefor.

Signed and Sealed this
Third Day of July, 2018

Andrei Iancu
*Director of the United States Patent and Trademark Office*